US007462695B2

(12) United States Patent
Dunse et al.

(10) Patent No.: US 7,462,695 B2
(45) Date of Patent: Dec. 9, 2008

(54) INSECT CHYMOTRYPSIN AND INHIBITORS THEREOF

(75) Inventors: Kerry Michelle Dunse, East Brunswick (AU); Robyn Louise Heath, Clifton Hill (AU); Marilyn Anne Anderson, Keilor (AU)

(73) Assignee: Hexima Limited, Melbourne (AU)

( * ) Notice: Subject to any disclaimer, the term of this patent is extended or adjusted under 35 U.S.C. 154(b) by 112 days.

(21) Appl. No.: 10/554,237

(22) PCT Filed: Apr. 23, 2004

(86) PCT No.: PCT/AU2004/000524

§ 371 (c)(1),
(2), (4) Date: Aug. 4, 2006

(87) PCT Pub. No.: WO2004/094630

PCT Pub. Date: Nov. 4, 2004

(65) Prior Publication Data

US 2007/0219147 A1    Sep. 20, 2007

Related U.S. Application Data

(60) Provisional application No. 60/465,054, filed on Apr. 23, 2003.

(51) Int. Cl.
*C07K 14/81* (2006.01)
*C07K 14/415* (2006.01)
*C12N 15/15* (2006.01)
*C12N 15/29* (2006.01)
*C12N 15/79* (2006.01)

(52) U.S. Cl. .................. 530/370; 435/69.2; 435/252.3; 435/320.1

(58) Field of Classification Search .................. None
See application file for complete search history.

(56) References Cited

U.S. PATENT DOCUMENTS

| 4,945,050 A | 7/1990 | Sanford et al. |
| 5,122,466 A | 6/1992 | Stomp et al. |

FOREIGN PATENT DOCUMENTS

DE    3135541 A    3/1983

(Continued)

OTHER PUBLICATIONS

Altschul et al., *Nucl. Acids Res.* 25:3389-3402 (1997).

(Continued)

*Primary Examiner*—William W Moore
(74) *Attorney, Agent, or Firm*—Greenlee, Winner and Sullivan, P.C.

(57) ABSTRACT

The present invention relates generally to a novel chymotrypsin that exhibits resistance to a plant serine proteinase inhibitor. More particularly, the present invention provides a chymotrypsin which is up-regulated in the gut of *Helicoverpa armigera* and *Helicoverpa punctigera* insect larvae when fed the serine proteinase inhibitors of *Nicotiana alata*. The novel chymotrypsin represents, therefore, a target for the identification of antagonists including inhibitors which are proposed to be useful in the control of *Helicoverpa* spp. populations that have become resistant to serine proteinase inhibitors produced in plants. The antagonists of the chymotrypsin may be topically applied to the plants or, when in proteinaceous form, may be produced by genetic means in plant cells. The antagonists may act at the level of gene expression or protein activity.

18 Claims, 36 Drawing Sheets

FOREIGN PATENT DOCUMENTS

| | | |
|---|---|---|
| WO | WO 84/03564 | 9/1984 |
| WO | WO 94/13810 | 6/1994 |
| WO | WO 97/02048 | 1/1997 |

OTHER PUBLICATIONS

Antcheva et al., *Protein Sci*. 10:2280-2290 (2001).
Atkinson et al., *The Plant Cell* 5:203-213 (1993).
Ausubel et al., "Current Protocols in Molecular Biology," John Wiley & Sons Inc., Chapter 15 (1994-1998).
Balandin et al., *Plant Mol. Biol*. 27:1197-1204 (1995).
Beuning and Christeller, *Plant Physiol 102*:1061 (1993).
Bevan, *Nucl. Acids Research 12*:8711-8721 (1984).
Bonner and Laskey, *Eur. J. Biochem. 46*:83 (1974).
Botos et al., *J. Mol. Biol*. 298:895-901 (2000).
Bown, et al., *Insect Biochem. Molec. Biol*. 27:625-638 (1997).
Bradford, *Anal Biochem* 72:248-254 (1976).
Broadway and Duffey, *J. Insect Physiol*. 32(8):673-680 (1986a).
Broadway and Duffey, *J. Insect Physiol*. 32(10):827-833 (1986b).
Broadway and Villani, *Entomol. Expo. Appl.* 76:303-312 (1995).
Broadway, *Arch. Insect Biochem. Physiol*. 32(1): 39-53 (1996).
Broadway, *J. Insect. Physiol*. 41: 107-116 (1995).
Broadway, *J. Insect. Physiol*. 43(9): 855-874 (1997).
Burgess et al., *Entomol. Exp. App. 61*: 123-130 (1991).
Choi et al., *Biochem. et Biophys. Acta 1492*: 211-215 (2000).
Christeller et al., *Insect Biochem. Molecul. Biol. 22*: 735-746 (1992).
Cleveland et al., *Plant Mol. Biol. 8*: 199-207 (1987).
Combet et al., *TIBS. 25*: 147-150 (2000).
Cordero et al., *The Plant Journal 6(2)*: 141-150 (1994).
Cripps et al., *J. Cell. Biol. 126*: 689-699 (1994).
De Leo et al., *Plant Physiol. 118*: 997-1004 (1998).
EMBL [Online] "Tomato leaf wound-induced proteinase inhibitor I Mrna, complete cds." XP002395902, retrieved from EBI accession No. EM_PRO:LEWIPI, Database accession No. K03290 (abstract) (1986).
EMBL [Online] "*Zea may* MPI gene" XP002395903, retrieved from EBI accession No. EM_PRO:ZMMPI, Database accession No. X78988 (abstract) (1994).
EMBL [Online] "*Nicotiana tabacum* mRNA for pre-pro-proteinase inhibitor I (PI-Ia gene)" XP002395904, retrieved from EBI accession No. EM_PRO:NTPII4PI, Database accession No. Z12619 (abstract) (1992).
EMBL [Online] "*S. tuberosum* proteinase inhibitor I." XP002395905, retrieved from EBI accession No. EM_PRO:STPROINI, Database accession No. Z12611 (abstract) (1992).
Erickson et al., *Science 249*: 527-533 (1990).
Fang et al., *Plant Cell 1*: 141-150 (1989).
Gatehouse et al., In: *Plant Genetic Manipulation for Crop Protection*, Biotech. In Agriculture No. 7, Eds. Gatehouse, Hilder & Boulter, International U.K., pp. 155-181 (1992).
Gatehouse et al., *J. Insect Physiol.* 45(6): 545-558 (1999).
Gatehouse et al., *Insect Biochem. Molecul. Biol.* 27(11): 929-944 (1997).
Graham et al., *J. Biol. Chem. 260*: 6555-6560 (1985).
Greenblatt et al., *J. Mol. Biol. 205*: 201 (1989).
Greer, *Proteins 7*: 317-34 (1990).
Hajdukiewicz et al., *Plant Mol. Biol. 25*: 989-994 (1994).
Harsulkar et al., *Plant Physiol. 121*: 497-506 (1999).
Heath et al., *European Journal of Biochemistry 230*(1): 250-257 (1995).
Heath et al., J. Insect Physiol. 43(9): 833-842 (1997).
Hediger et al., *Insect Mol. Biol. 10*: 113-119 (2001).

Hjelmeland et al., *Comparative Biochemistry and Physiology B 71*: 557-562 (1982).
Hodgson, Bio/Technology 9: 19-21 (1991).
Hsu et al., *Plant. Sci. 143*: 63-70 (1999).
Inoue et al., Gene 96: 23-28 (1990).
Johnson, R. et al., Proceedings of the National Academy of Sciences of USA, National Academy of Science, Washington, DC, US, 86:24, pp. 9871-9875 (1989).
Johnston et al., *Insect Biochem. 2*(4)1: 389-397 (1991).
Johnston et al., *Insect Biochem. Molec. Biol. 25*(3): 375-383 (1995).
Jongsma et al., *Proc. Natl. Acad. Sci. USA 92*(17): 8041-8045 (1995a).
Keil et al., *EMBO J. 8*: 1323-1330 (1989).
Lee et al., *Insect. Biochem. Molec. Biol. 25*(1): 49-61 (1995b).
Lee et al., *Insect. Biochem. Molec. Biol. 25*(1): 63-71 (1995a).
Lee et al., *Nature Structural Biology 6*(6): 526-530 (1999).
Legavre et al., In: 5th International Congress of Plant Molecular Biology, Singapore 15:3 Supp., Kluwer Academic Publishers (1997).
Lidholm et al., *Genetics 134*: 859-868 (1993).
Linthorst et al., *Plant Mol. Biol. 21*: 985-992 (1993).
Lozovskaya et al., *Genetics 142*: 173-177 (1996).
Markwick et al., *J. Economic Entomology 91* (6): 1265-76 (1998).
Markwick et al., *J. Economic Entomology 88*(1): 33-39 (1995).
Marmur et al., *J. Mol. Biol. 5*: 109-118 (1962).
Mazumdar-Leighton and Broadway, *Insect Biochem. Mol. Biol. 31*: 645-657 (2001a).
Mazumdar-Leighton and Broadway, *Insect Biochem. Mol. Biol. 31*: 633-644 (2001b).
Miller et al., *Plant Cell 11*: 1499-1508 (1999).
Miller et al., *Plant Mol. Biol. 42*: 329-333 (2000).
Moura et al., *Plant Physiol. 126*: 289-298 (2001).
Nielson et al., *Biochemistry 34*: 14304-14311 (1995).
Nielson et al., *J. Mol. Biol. 242*: 231-243 (1994).
Patankar et al., *Insect Biochem. & Mol. Biol. 31*: 453-464 (2001).
Pathirana et al., *Plant J. 12*(2): 293-304 (1997).
Paulillo et al., *J. Econ. Entomol. 93*(3): 892-896 (2000).
Peloquin et al., *J. Cot. Sci. 5*: 114-120 (2001).
Pesole, *Trends Genet 15*(9): 378 (1999).
Peterson et al., *Insect Biochem. Mol. Biol. 25*(7): 765-774 (1995).
Pujade-Renaud et al., *Plant Physiol. Biochem. 35*(2): 85-93 (1997).
Richardson et al., *FEBS Letters 52*(1): 161 (1975).
Ryan, *Annu. Rev. Phytopathol. 28*: 425-449 (1990).
Sakal et al., *International Journal of Peptide and Protein Research 34*: 498-505 (1989).
Samac et al., *Plant Cell 3*: 1063-1072 (1991).
Schoenbeck et al., *Molec. Plant-Microbe Interact 12*(10) 882-893 (1999).
Seemuller et al., *Hoppe Seyler's Z. Physiol. Chem 358*: 1105-1117 (1977).
Stewart and Hsu, *Planta 137*: 113-117 (1977).
Summerton et al., *Antisense and Nucleic Acid Drug Development 7*: 187-195 (1997).
Taylor et al., *Plant Mol. Biol. 23*: 1005-1014 (1993).
Teakle et al., *Journal of Invertebrate Pathology 46*: 166-173 (1985).
Terra et al., *Comp. Biochem. Physiol. 109B*: 1-61 (1994).
Umbek et al., Biotechnology 5: 263-266 (1987).
Valaitis et al., *Insect Biochemistry and Molecular Biology 29*: 405-415 (1999).
Volpicella et al., *Eur. J. Biochem. 270*: 10-19 (2003).
Wells, *Methods Enzymol. 202*: 390-411 (1991).
Wu et al., *Molecular Breeding 3*: 371-380 (1997).
Xu et al., *J. Econ. Entomol. 87*(2): 334-338 (1994).
Beuning, L. L., et al., "Evolution of the proteinase inhibitor I family and apparent lack of hypervariability in the proteinase contact loop," *J Mol Evol* 39:644-654 (1994).

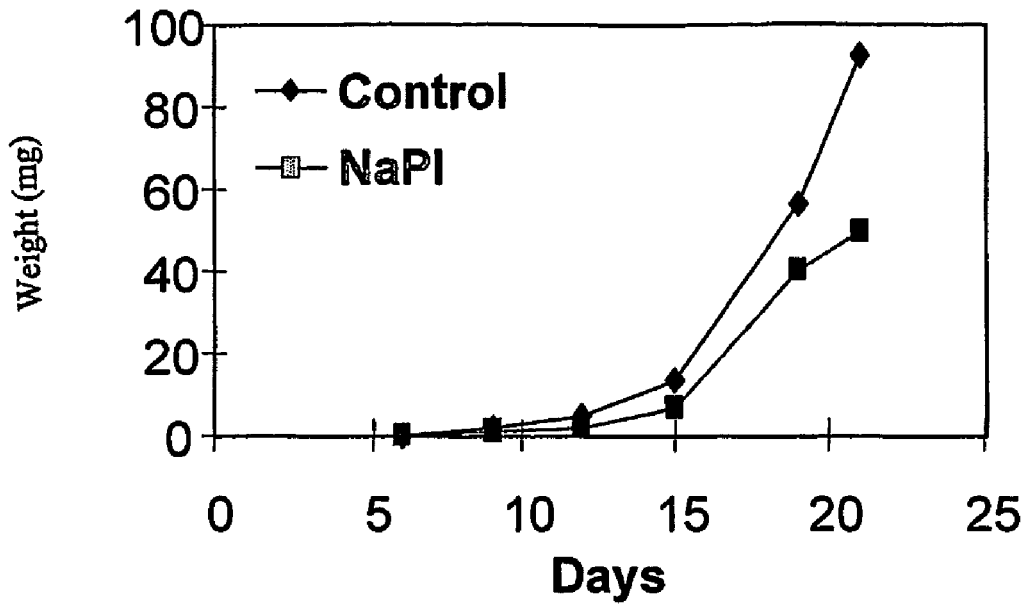
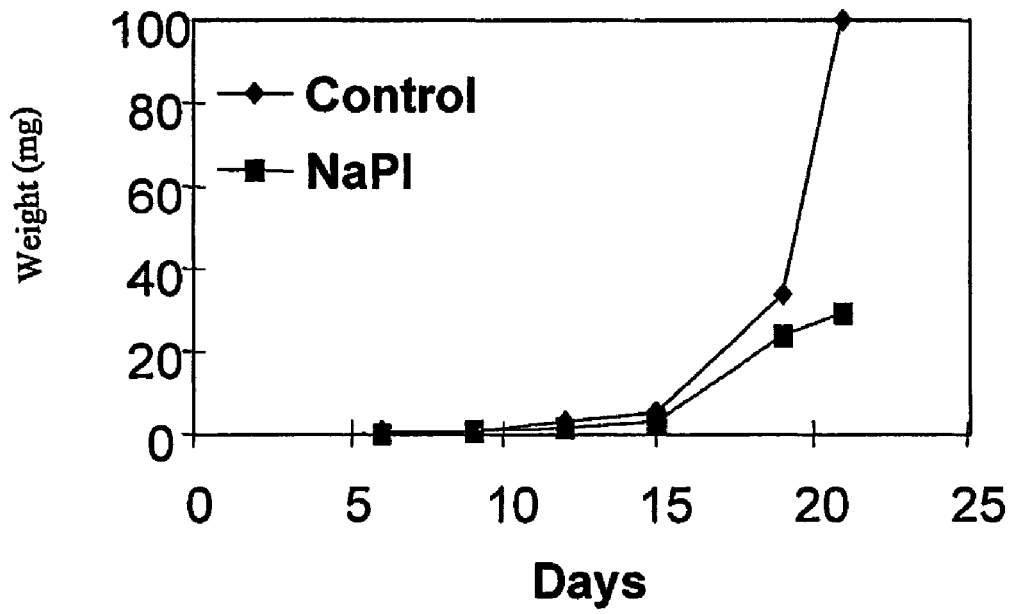
Figure 2A

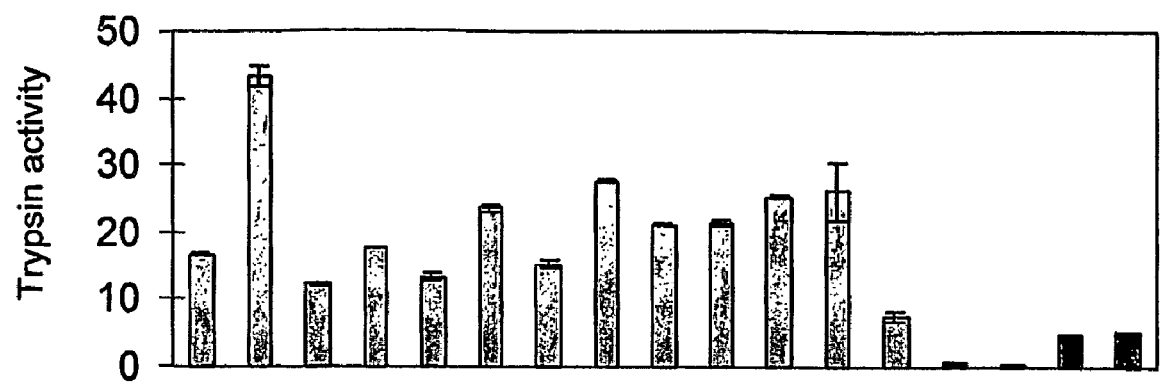
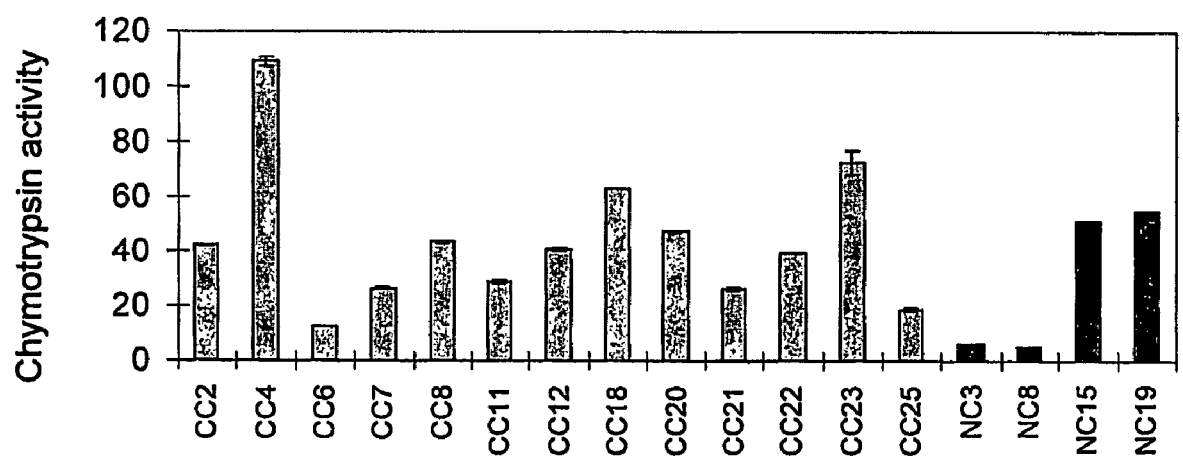
Figure 2C

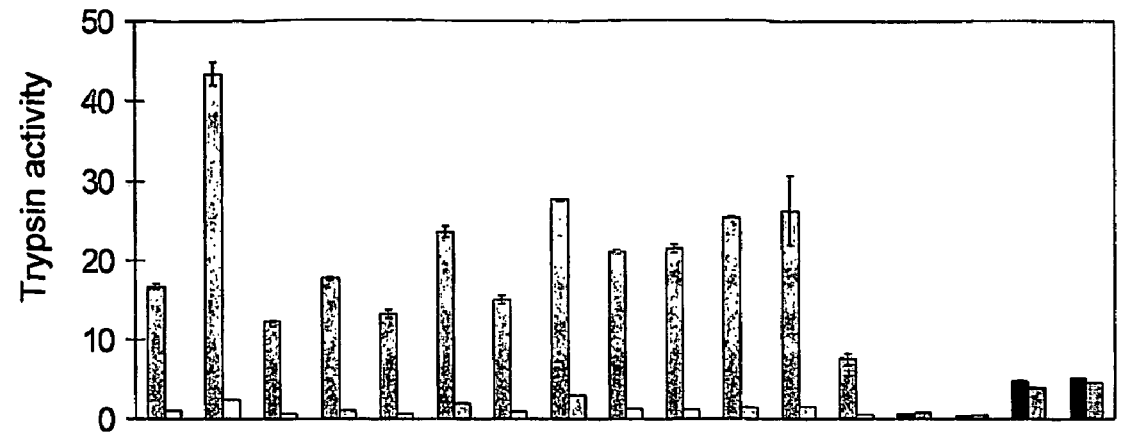
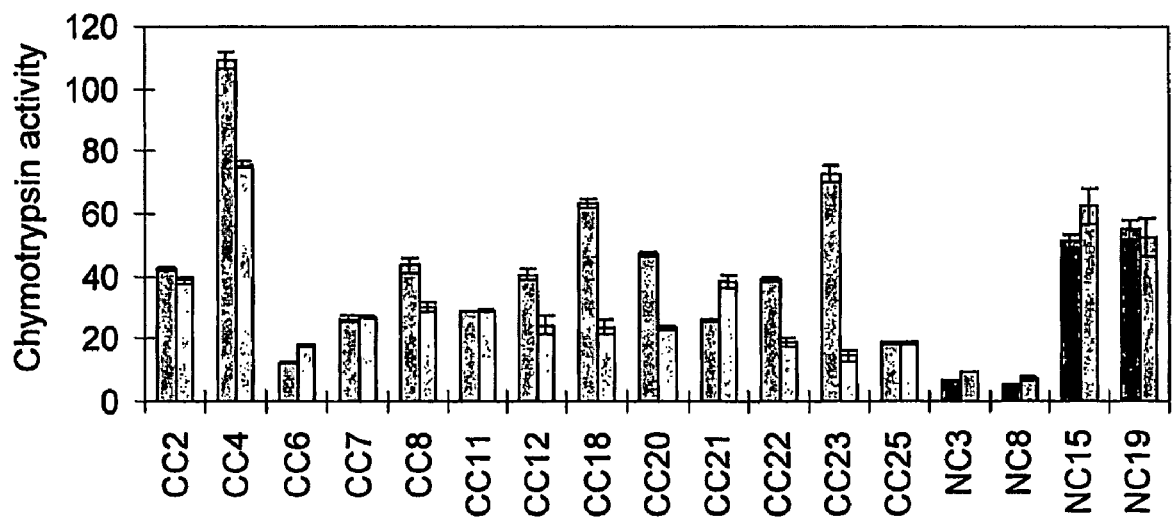
Figure 2F

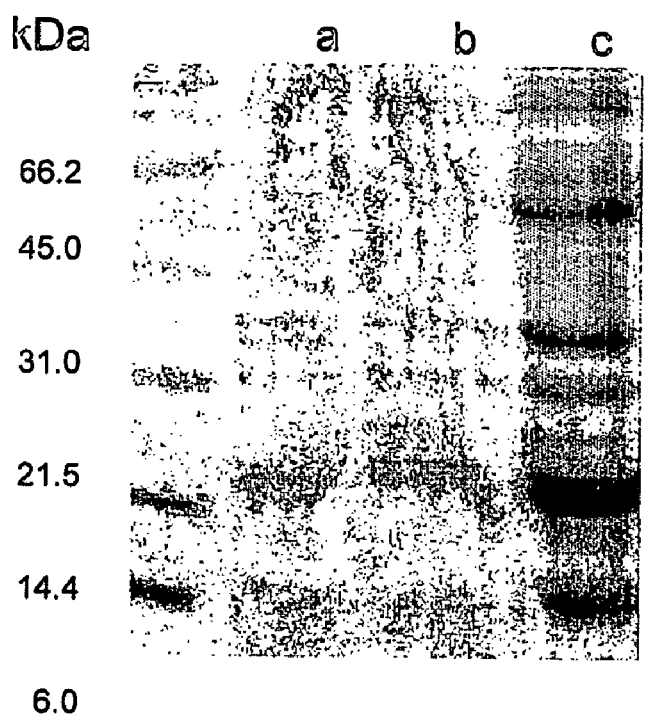
Figure 4A
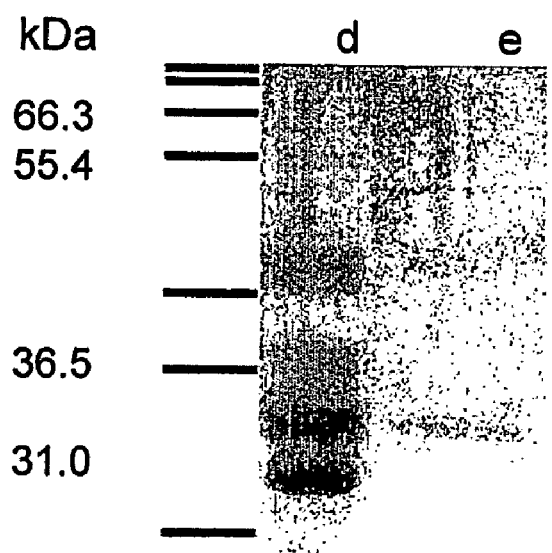
Figure 4B
21.5
HpCHY1    IVGGSTSSLGATPYQ
Figure 4C

```
CAA72966  MKLLAVTLLAFAAVVSARNIDLEDVIDLEDITAYDYHTKIGIPLAEKIRA
CAA72959  ---LAVTLLAFAAVVSARNIDLEDVIDLEDITAYDYHTKIGIPLAEKIRA
CAA72960  MKLLAVTLLAFAAIVSARNIDLEDVIDLEDITAYDYHTKIGIPLAEKIRA
CAA72958  ------------------INHEAVVDLEDITAYGYHTKVGIPLAEEIRI
CAA72952  MKLFLGVCLTLAVAVSAVEIATPD----ADSPVFGYHAKFGIAEAARIKS
CAA72951  --------------------------------------------------

FwY79→  FwG1→
CAA72966  AEEEAERNPSRIVGGSTSSLGAF PYQAGL LATFASGQGVCGGSLLNNRRV
CAA72959  AEEEAERNPSRIVGGSTSSLGAFPYQAGLLATFASGQGVCGGSLLNNRRV
CAA72960  AEEEAERNPSRIVGGSISSLGAF PYQAGL LATFASGQGVCGGSLLNNRRV
CAA72958  AELEASRNPSRIVGGS SASLGQ FPYQAGLLINLPLGQSVCGGSLLNQRRV
CAA72952  AEEVQSFNGQRIVGGSITNIANV PYQAGL VITIFIFQSVCGASLISHNRL
CAA72951  -----------------------------------------HNKWV

CAA72966  LTAAHCWFDGRNQARSFTVVLGSVRLFSGGTRLNTASVVMHGSWNPNLIR
CAA72959  LTAAHCWFDGRNQARSFTVVLGSVRLFSGGTRLNTASVVMHGSWNPNLIR
CAA72960  LTAAHCWFDGRNQARSFTVVLGSVRLFSGGTRLNTASVVMHGSWNPNLIR
CAA72958  LTAAHCWFDGRNQANSLTVILGSINLYFGGTRLNSNSVVMHGSWNPNLIR
CAA72952  VTAAHCKSDGVLTANSFTVVLGSNTLFFGGTRINTNDVVMHPNWNPNTAA
CAA72951  LTAAHCLANRITFVVRFGLTNLTRPEILVESANKYIHPDYDEIRAG-VQT

CAA72966  NDIAMINLPSNVATSGNIAP--IALPSGNELNNNFNGATAVASGFGLARD
CAA72959  NDIAMINLPSNVATSGNIAP--IALPSGNELNNNFNGATAVASGFGLARD
CAA72960  NDIAIINLPSNVATSGNIAP--IALPSGNELNNNFNGATAVASGFGLAND
CAA72958  NDIAIINLPSNVGTSNNIAP--IALPSGNELNNQFAGFTATASGFGRTRD
CAA72952  NDIAVLRISS-VSFSNVIQP--IALPSGDELNNLFVGANALASGFGRTSD
CAA72951  ADLALVGLDHHIEYSANVQPSRLMSSAQKNINYE--GIQMIVSGFGRTDD

FwY72→
CAA72966  GGSVDGN---LRHVNLPVITNAVCTVSFP-GIIQSS-NICTSG--ANGRS
CAA72959  GGSVDGN---LRHVNLPVITNAVCTVSFP-GIIQSS-NICTSG--ANGRG
CAA72960  GGSVDGN---LRHVNLPVITNAVCTVSFP-GIIQSS-NICTSG--ANGRS
CAA72958  GGSVSPT---LNHVNLPVITNNVCWQSFP-LYIQSS-NICTSG--ANGRS
CAA72952  SGSIGTN-QQLSSVTIPVITNAQCAAVYGSGFVHAS-NICTSG--AGGKG
CAA72951  LWNGGAASEILL WVYQRGV SNEECLRWYPTSQVIKEETICAGYWDNPSQS

←RvG4
CAA72966  TCQGDSGGPLVVTSN-NRRILIGVTSFGSARGCQVGS PAAFAR VTSFISW
CAA72959  TCQGDSGGPLVVTSN-NRRILIGVTPFGSARGCQVGS PAAFAR VTSFISW
CAA72960  TCQGDSGGPLVVTSN-NRRILIGVTSFGSARGCQVGS PAAFAR VTSFISW
CAA72958  TCQGDSGGPLVVTSN-NRRILIGVTSFGSDRGCQVGS PAAFAR VTSFISW
CAA72952  TCNGDSGGPLAVDSN-NRKILIGVTSYGAQAGCAAGF PAAFAR VTSFVDW
CAA72951  SCQGDSGGPLTIIDADGERTQVGIVSFGSTAGCNSPFPSGYVRPGHYH DW

←RvY72
CAA72966  INQRL---------------------------------------------
CAA72959  INQRL---------------------------------------------
CAA72960  INNLL---------------------------------------------
CAA72958  INQRL---------------------------------------------
CAA72952  VQSQ----------------------------------------------
CAA72951  FTEV TGINFDWDSDAIIPGSSESSSSESSEPSSESSESSSEEDGANPSSS

CAA72966  ----------------------------
CAA72959  ----------------------------
CAA72960  ----------------------------
CAA72958  ----------------------------
CAA72952  ----------------------------
CAA72951  EEDGSNPSSEEDAGSPPSEEEEAPEKVRVVEY
```

Figure 7

| Primer Name | Sequence 5'-3' |
|---|---|
| FWG1 | TCC CTT ACC AGG C(GCT) GTC [SEQ ID NO:38] |
| RVG4 | TCT GGC GAA GGC AGC AGG [SEQ ID NO:39] |
| Y79Fw | CTG CTA GCC TCG GAC AAT TC [SEQ ID NO:40] |
| Y72Fw | CTG GAG TGC AGA CTG CTG AC [SEQ ID NO:41] |
| Y72Rv | GGA TGA TGG CGT CGC TGT CC [SEQ ID NO:42] |

Figure 8

```
HpF1Apcr    PYQAGLVITIFIFQSVCGASLIPHNRLVTAAHCKSDGVLTANSFTVVLGS  50
HpF1Bpcr    PYQAGLVITIFIFQSVCGASLISHNRLVTAAHCKFDGVMTANSFTVVLGS  50
HpF2Apcr    PYQAGLLANFASGQGVCGGSLLNQRRVLTAAHCWFDGRNQARSFTVVLGS  50
HpF3pcr  ASLGQFPYQAGLLINLPLGQSVCGGSLLNQRRVLTAAHCWFDGRNQATSLTVILGS  57
HpF4pcr     --------------------------------------------------

HpF1Apcr    NTLFFGGTRINTNDVVMHPNWNPSTAANDIAVMRISS-VSFSNVIQPIAL  99
HpF1Bpcr    NTLFFGGTRINTNDVVMHPNWNPSTVANDIAVIRISS-IVFNNVIQPIAL  99
HpF2Apcr    VRLFSGGTRLDTASVVMHGSWNPNLIRNDIAMINLPSNVATSGNIAPIAL  100
HpF3pcr     INLFFGGTRLNSNSVVMHGSWNPNLIRNDIAIINLPSNVGTSGNIAPIAL  100
HpF4pcr     -------------------SGVQTADLALVGLDQEIEYSANVQPSRL  28

HpF1Apcr    PSGDELNNLFVGANALASGFGRTSDGGSIGSNQQ-VSSVTIPVITNDECA  148
HpF1Bpcr    PSGDELNNLFVGANALASGFGRTSDSGGIGTNQQ-LSSVTIPVITNAECA  148
HpF2Apcr    PSGNELNNNFNGATATASGFGLARDGGSVDGN---LRHVNLPVITNAVCT  147
HpF3pcr     PSGNELNNQFAGFTATASGFGLTRDGGNVSPT---LNHVNLPVITNNVCW  147
HpF4pcr     MSSAQKNINYEGIQMIVSGFGRTDDLWNGGAASEILLWVYQRGVSNEECL  78

HpF1Apcr    AVYGS-AFVHSSNICTSGAGG--KGTCNGDSGGPLAIDSNN-EKILIGVT  194
HpF1Bpcr    AVYGP-AFVHDTNICTSGAGG--KGTCNGDSGGPLAVDSND-KKILIGVT  194
HpF2Apcr    VSFP--GIIQSSNICTSGANG--RSTCQGDSGGP---------------  177
HpF3pcr     QSFP--LYIQSTNICTSGANG--RGTCQGDSGGPLVVTSNN-RRILIGVT  192
HpF4pcr     RWYPTSQVIKEQTICAGYWDNPSQSSCQGDSGGPLTIIDADGERTQVGIV  128

HpF1Apcr    SYGAQAGCAAGLPAAFARK---------------------  213
HpF1Bpcr    SYGAADGCAAGFPAASPER---------------------  213
HpF2Apcr    ----------------------------------------
HpF3pcr     SFGSDRGCQVGAPAAFAR----------------------  210
HpF4pcr     SFGSTAGCNSPFPSGYVRPGHYHDWFTEVTGINFDWDSDAII  120
```

Figure 9

```
HpCh1AI    ----------  ---AVSA---  -VEIGTPDAD  SPVFGYHAKF  GIPEAARIKS   33
HpCh1BI    MKLFLGVCLA  LAVAVSA---  -VEIGTPEAG  SPVFGYHAKF  GIAEAARIKS   46
HpCh2A     MKLLAVTLLA  FAAVVSARNI  DLEDVIDLED  ITAYDYHTKI  GIPLAEEIRA   50
HpCh2B     MKLLAVTLLA  FAAVVSARNI  DLEDVIDLED  ITAYDYHTKI  GIPLAEKIRA   50
HpCh3A     ----------  ----------  ----------  ----------  ----------
HpCh4I     MAAAYLLGLL  FVLGYVQGGL  LNADPAIIED  LRDA------  ----------   34
HpCh4II    MAAAYLLGLL  FVLGYVQGGL  LNADPAIIED  LRDA------  ----------   34
                ↓↓                               ⊙
HpCh1AI    AEEVQSFNGQ  RIVGGSITDI  ANVPYQAGLV  ITIFIF-QSV  CGASLISHNR   82
HpCh1BI    AEEVQSFNGQ  RIVGGSITNI  ANVPYQAGLV  ITIFIF-QSV  CGASLISHNR   95
HpCh2A     AEEEAERDPS  RIVGGSTSSL  GAFPYQAGLL  ANFASG-QGV  CGGSLLNQRR   99
HpCh2B     AEEEAERNPS  RIVGGSTSSL  GAFPYQAGLL  ASFASG-QGV  CGGSLLNVRR   99
HpCh3A     ----------  -IVGGSSASL  GQFPYQAGLL  INLPLG-QSV  CGGSLLNQRR   38
HpCh4I     --EFSSG--S  RIVAGWPAVE  GQIPYQGSLR  MVSAIGGVSS  CGCSLIHNKW   80
HpCh4II    --EFSSF--S  RIVAGWPAVE  GQIPYQGSLR  MVSAIGGVSS  CGCSLIHNKW   80
                ▼●
HpCh1AI    LVTAAHCKSD  GVLTANSFTV  VLGSNTLFFG  GTRINTNDVV  MHPNWNPS--  130
HpCh1BI    LVTAAHCKFD  GVMTANSFTV  VLGSNTLFFG  GTRINTNDVV  MHPNWNPS--  143
HpCh2A     VLTAAHCWFD  GRNQARSFTV  VLGSVRLFSG  GTRLDTASVV  MHGSWNPN--  147
HpCh2B     VLTAAHCWFD  GRNQARSFTV  VLGSVRLYSG  GTRLNTASVV  MHGSWNPN--  147
HpCh3A     VLTAAHCWFD  GRNQATSLTV  ILGSINLFFG  GTRLNSNSVV  MQGSWNPN--   86
HpCh4I     VLTAAHCLAN  ----RITFVV  RFGLTNLTRP  EILVESTNKY  IHPEYDEIRA  126
HpCh4II    VLTAAHCLAN  ----RITFVV  RFGLTNLTRP  EILVESTNKY  IHPEYDEIRA  126
                ▼
HpCh1AI    -TAANDIAVM  RISS-VSFSN  VIQPIALPSG  DELNNLFVGA  NALASGFGRT  178
HpCh1BI    -TVANDIAVI  RISS-IVYNN  VIQPIALPSG  DELDNLFVGA  NALASGFGRT  191
HpCh2A     -LIRNDIAMI  NLPSNVATSG  NIAPIALPSG  NELNNNFNGA  TATASGFGLA  196
HpCh2B     -LVRNDIAMI  NLPSNVATSG  NIAPIALPSG  NELNNQFAGA  TATASGFGLA  196
HpCh3A     -LIRNDIAII  NLPSNVGTSG  NIAPIALPSG  NELNNQFAGF  TATASGFGLT  135
HpCh4I     GVQTADLALV  GLDHEIEYSA  NVQPSRLMSS  AQKNINYEGI  QMIVSGFGRT  176
HpCh4II    GVQTADLALV  GLDQEIEYSA  NVQPSRLMSS  AQKNINYEGI  QMIVSGFGRT  176
                                       ●                      ●
HpCh1AI    SDGGSIGSNQ  Q-VSSVTIPV  ITNDECAAVY  GS-AFVHSSN  ICTSGAGG--  224
HpCh1BI    SDSGGIGTNQ  Q-LSSVTIPV  ITNAECAAVY  GP-AFVHDTN  ICTSGAGG--  237
HpCh2A     RDGGSVDGN-  --LRHVNLPV  ITNAVCTVSF  P--GIIQSSN  ICTSGANG--  239
HpCh2B     RDGGVIDGN-  --LRHVNLPV  ITNAVCSQSF  P--GLIQASN  VCTSGANG--  239
HpCh3A     RDGGNVSPT-  --LNHVNLPV  ITNNVCWQSF  P--LYIQSTN  ICTSGANG--  178
HpCh4I     DDLWNGGAAS  EILLWVYQRG  VSNEECLRWY  PTSQVIKEQT  ICAGYWDNPS  226
HpCh4II    DDLWNGGAAS  EILLWVYQRG  VSNEECLRWY  PTSQVIKEQT  ICAGYWDNPS  226
             ¥ ● ▼                     §         ●           #
HpCh1AI    KGTCNGDSGG  PLAVDSNNEK  IL-IGVTSYG  AQAGCAVG--  ---LPAAFAR  268
HpCh1BI    KGTCNGDSGG  PLAVDSNDKK  IL-IGVTSYG  AADGCAAG--  ---FPAAFAR  281
HpCh2A     RSTCQGDSGG  PLVVNSNNRR  IL-IGVTSFG  SARGCQVG--  ---SPAAFAR  283
HpCh2B     RSTCQGDSGG  PLVVNSNNRR  IL-IGVTSFG  SARGCQVG--  ---SPAAFAR  283
HpCh3A     RGTCQGDSGG  PLVVTSNNRR  IL-IGVTSFG  SDRGCQVG--  ---APAAFAR  222
HpCh4I     QSSCQGDSGG  PLTIIDADGE  RTQSRYCELR  --IHCWNA--  -AHSPQGYVR  272
HpCh4II    QSSCQGDSGG  PLTIIDADGE  RTQVGIVSSD  PLLDATVHSP  RVTSPGHYHD  276

HpCh1AI    VTSFVSWVQS  Q---------  ----------  ----------  ----------  279
HpCh1BI    VTSFVSWVQS  Q---------  ----------  ----------  ----------  292
HpCh2A     VTSFISWINQ  RL--------  ----------  ----------  ----------  295
HpCh2B     VSSYISWINQ  RL--------  ----------  ----------  ----------  295
HpCh3A     VTSYISWINQ  RL--------  ----------  ----------  ----------  234
HpCh4I     PGHYHDWFTE  VTGINFDWDS  DAIIP-----  ----------  ----------  297
HpCh4II    GHRGDRHQLR  LGQRRHYPDS  SESSLRAAIL  PLESSRAFIR  RNQSSFRGGL  326
```

Figure 10A

```
HpCh1AI  ----------  ----------  ----------  ---------- 279
HpCh1BI  ----------  ----------  ----------  ---------- 292
HpCh2A   ----------  ----------  ----------  ---------- 295
HpCh2B   ----------  ----------  ----------  ---------- 295
HpCh3A   ----------  ----------  ----------  ---------- 234
HpCh4I   ----------  ----------  ----------  ---------- 297
HpCh4II  CQPPRFPTRT  VPTHLPRRTL  AAPPSEEEEA  PEKVRVVEY  365
```

Figure 10B

```
                                              F1           F2
                                           ┌────┐       ┌────┐
                                           │    │       │    │
[SEQ ID NO:55]   Rech1a         IVGGSLS SVG  QIP YQAGL VI  DLAGG QAV~C GGSLISA
[SEQ ID NO:56]   Rech1b         IVGGSTSSVG QFPYQAGLLA SFAGGQAV~C G
[SEQ ID NO:57]   Family1a       IVGGSITDIA NVPYQAGLVI TIFIFQSV~C GASLISHN
[SEQ ID NO:58]   Family1b       IVGGSITNIA NVPYQAGLVI TIFIFQSV~C GASLISHN
[SEQ ID NO:59]   Family2a       IVGGSTSSLG AFPYQAGLLA SFASGQGV~C GGSLLNVR
[SEQ ID NO:60]   Family2b       IVGGSTSSLG AFPYQAGLLA NFASGQGV~C GGSLLNQR
[SEQ ID NO:61]   Family3        IVGGSSASLG QFPYQAGLSL IY~SGQSV~C GGSLLNQRR
[SEQ ID NO:62]   Family4        IVAGWPAVEG QIPYQGSLRM VSAIGGVSSC GCSLIHN
```

Figure 11A

| N-terminal sequence of resistant chymotrypsin (Rech 1a) |||
|---|---|---|
| F1        F2<br>IVGGSLSSVG QIPYQAGLVDLAGGQAVCGGSLISA [SEQ ID NO:9] |||
| Primer Name | Oligonucleotide sequence 5'-3' ||
| Fw2ResChy = F1 | TC(AGCT) GT(AGCT) GG(AGCT) CA(AG) AT(ACT) CC [SEQ ID NO:10] ||
| FwResChym = F2 | GT(AGCT) AT(ACT) GA(CT) CT(AGCT) GC(AGCT) GG(AGCT) GG [SEQ ID NO:11] ||

Figure 11B

```
HpCHF5  GTTCACCTCGAGGATTCTATTGATCTGGAAGATATTACCGCTTGGGGATA  50
         V  H  L  E  D  S  I  D  L  E  D  I  T  A  W  G  Y
        -40                                               -24
HpCHF5  CCTCACCAAATTCGGTATTCCAGAAGCTGAGAAAATCCGCAACGCTGAAG  100
         L  T  K  F  G  I  P  E  A  E  K  I  R  N  A  E
                                                       -8
HpCHF5  AAGCTAGCTCTGCTAGCAGGATCGTCGGTGGTTCATTGTCCAGTGTCGGA  150
         E  A  S  S  A  S  R  I  V  G  G  S  L  S  S  V  G
                               -1 +1                      +10
HpCHF5  CAGATCCCTTACCAGGCTGGTCTCGTCATTGACTTAGCAGGTGGCCAGGC  200
         Q  I  P  Y  Q  A  G  L  V  I  D  L  A  G  G  Q  A

HpCHF5  TGTCTGCGGAGGCTCCCTGATCAGCGCTTCCCGCGTACTGACCGCTGCTC  250
         V  C  G  G  S  L  I  S  A  S  R  V  L  T  A  A

HpCHF5  ACTGCTGGTTCGACGGCCAAAACCAGGCCTGGAGATTCACCGTTGTTCTT  300
         H  C  W  F  D  G  Q  N  Q  A  W  R  F  T  V  V  L
         #
HpCHF5  GGTTCCACCACCTTGTTCTCTGGCGGTACCAGAATCCCTACATCCAATGT  350
         G  S  T  T  L  F  S  G  G  T  R  I  P  T  S  N  V

HpCHF5  TGTTATGCACGGAAGCTGGACTCCTAGCCTTATCCGTAACGATGTTGCCG  400
         V  M  H  G  S  W  T  P  S  L  I  R  N  D  V  A
                                                       #
HpCHF5  TAATCAGATTGGGCACCAACGTAGCAACCTCAAACACCATTGCCATCATC  450
         V  I  R  L  G  T  N  V  A  T  S  N  T  I  A  I  I

HpCHF5  GCTCTACCCAGCGGCAGCCAGATCAACGAGAACTTCGCCGGTGAAACCGC  500
         A  L  P  S  G  S  Q  I  N  E  N  F  A  G  E  T  A

HpCHF5  CCTCGCCTCCGGCTTCGGTCTCACCAGTGACACCGGCAGCATCTCCAGCA  550
         L  A  S  G  F  G  L  T  S  D  T  G  S  I  S  S

HpCHF5  ACCAGGCTCTGAGCCACGTCAACCTGCCAGTGATCACCAACGCTGTGTGC  600
         N  Q  A  L  S  H  V  N  L  P  V  I  T  N  A  V  C

HpCHF5  AGAAATTCATTCCCCCTGCTGATCCAGGACTCTAACATTTGCACCAGCGG  650
         R  N  S  F  P  L  L  I  Q  D  S  N  I  C  T  S  G

HpCHF5  TGCCAACGGCAGGAGCACTTGCCGCGGTGACTCCGGCGGTCCTCTCGTCG  700
         A  N  G  R  S  T  C  R  G  D  S  G  G  P  L  V
                     §                       #
HpCHF5  TCACCAGGAACAACAGACCACTCTTGATCGGTATCACCTCTTTCGGATCT  750
         V  T  R  N  N  R  P  L  L  I  G  I  T  S  F  G  S

HpCHF5  GCCCGCGGTTGCCAAGTTGGATCTCCCGCTGCCTTCGCCAGAGTCACCTC  800
         A  R  G  C  Q  V  G  S  P  A  A  F  A  R  V  T  S

HpCHF5  TTACATCAGCTGGATCAACGGCCAGCTCTAAAATATCGAACATTTTGCCA  850
         Y  I  S  W  I  N  G  Q  L  *

HpCHF5  TATCTACAGAGATATTTTGAAATACGTTAATTTAAATAAATATTTTATTT  900
HpCHF5  ATTCAAAAAAAAAAAAAAAAA                              921
```

Figure 12

```
HpCh1AI    IVGGSITDIANVPYQAGLVITIFI-FQSVCGASLISHNRLVTAAHCKSDG  49
HpCh1BI    IVGGSITNIANVPYQAGLVITIFI-FQSVCGASLISHNRLVTAAHCKFDG  49
HpCh2A     IVGGSTSSLGAFPYQAGLEANFAS-GQGVCGGSLLNQRRVLTAAHCWFDG  49
HpCh2B     IVGGSTSSLGAFPYQAGLLASFAS-GQGVCGGSLNVRRVLTAAHCWFDG   49
HpCh3      IVGGSSASLGQFPYQAGLSLIYS--GQSVCGGSLLNQRRVLTAAHCWFDG  48
HpCh4I     IVAGWPAVEGQIPYQGSLRMVSAIGGVSSGGCSLIHNKWVLTAAHCLAN-  49
HpCh5      IVGGSLSSVGQIPYQAGLVIDLAG-GQAVCGGSLISASRVLTAAHCWFDG  49
TrypsinIV  IVGGYTCEENSLPYQVSLNSGSH-----FCGGSLISEQWVVSAAHCY---  42

HpCh1AI    VLTANSFTVVLGSNTLFFGG-TRINTNDVVMHPNWNPS---TAANDIAVM  95
HpCh1BI    VMTANSFTVVLGSNTLFFGG-TRINTNDVVMHPNWNPS---TVANDIAVI  95
HpCh2A     RNQARSFTVVLGSVRLFSGG-TRLDTASVVMHGSWNPN---LIRNDIAMI  95
HpCh2B     RNQARSFTVVLGSVRLYSGG-TRLNTASVVMHGSWNPN---LVRNDIAMI  95
HpCh3      RNQATSLTVILGSINLFFGG-TRLNSNSVVMHGSWNPN---LIRNDIAII  94
HpCh4I     ---RITFVVRFGLTNLTRPE-ILVESTNKYIHPEYDEIRAGVQTADLALV  95
HpCh5      QNQAWRFTVVLGSTTLFSGG-TRIPTSNVVMHGSWTPS---LIRNDVAVI  95
TrypsinIV  -KTRIQVRLGEHNIKVLEGNEQFINAAKIIRHPKYNRD---TLDNDIMLI  88

HpCh1AI    RISS-VSFSNVIQPIALPSGDELNNLFVGANALAFGFGRISDGGSIGSNQ  144
HpCh1BI    RISS-IVYNNVIQPIALPSGDELDNLFVGANALASGFGRISDSGGIGTNQ  144
HpCh2A     NLPSNVATSGNIAPIALPSGNELNNNFNGATATASGFGLARDGGSVDGN-  144
HpCh2B     NLPSNVATSGNIAPIALPSGNELNNQFAGATATASGFGLARDGGVIDGN-  144
HpCh3      NLPSNVGTSGNIAPIALPSGNELNNQFAGFTATASGFGLIRDGGNVSPT-  143
HpCh4I     GLDHEIEYSANVQPSRLMSSAQKNINYEGIQMIVSGFGRIDDLWNGGAAS  145
HpCh5      RLGINVATSNTIAIIALPSGSQINENFACETALASGFGLTSDTGSISSNQ  145
TrypsinIV  KLSSPAVINARVSTISLPIAP----PAAGTECLISGWGNTLSFGADYPD-  133

HpCh1AI    Q-VSSVTIPVITNDECAAVYG-SAFVHSSNICT--SGAGGKGTCNGDSGG  190
HpCh1BI    Q-LSSVTIPVITNAECAAVYG-PAFVHDTNICT--SGAGGKGTCNGDSGG  190
HpCh2A     --LRHVNLPVITNAVCTVSF--PGIIQSSNICT--SGANGRSTCQGDSGG  188
HpCh2B     --LRHVNLPVITNAVCSQSF--PGLIQASNVCT--SGANGRSTCQGDSGG  188
HpCh3      --LNHVNLPVITNNVCWQSF--PLYIQSTNICT--SGANGRGTCQGDSGG  187
HpCh4AI    EILLWVYQRGVSNEECLRWYPTSQVIKEQTICAGYWDNPSQSSCQGDSGG  195
HpCh5      A-LSHVNLPVITNAVCRNSF--PLLIQDSNICT--SGANGRSTCRGDSGG  190
TrypsinIV  E-LKCLDAPVLTQAECKASY--PGKITNSMFCVG-FLEGGKDSCQRDSGG  179
                                                       ↑↑
HpCh1AI    PLAIDSNN--EKILIGVTSYGAQAGCAAGLPAAFARVTSFVSWVQSQ---  235
HpCh1BI    PLAVDSND--KKILIGVTSYGAADGCAAGFPAAFARVTSFVSWVQSQ---  235
HpCh2A     PLVVNSNN--RRILIGVTSFGSARGCQVGSPAAFARVTSEISWINQRL--  234
HpCh2B     PLVVNSNN--RRILIGVTSFGSARGCQVGSPAAFARVSSYISWINQRL--  234
HpCh3      PLVVTSNN--RRILIGVTSFGSDRGCQVGAPAAFARVTSYISWINQRL--  233
HpCh4I     PLTIIDADGERTQSRYCELRIHCWNATAHSPQGYVRPGHYHDWFTEVTGI  245
HpCh5      PLVVTRNN--RPLLIGITSFGSARGCQVGSPAAFARVTSYISWINGQL--  236
TrypsinIV  PVVCNG------QLQGVVSWGHGCAWKN-RPGVYTKVYNYVDWIKDTIAA  222

HpCh1AI    ------------ 235
HpCh1BI    ------------ 235
HpCh2A     ------------ 234
HpCh2B     ------------ 234
HpCh3      ------------ 233
HpCh4I     NFDWDSDAIIP  256
HpCh5      ------------ 236
TrypsinIV  NS---------- 224
```

Figure 13

| | | | | | |
|---|---|---|---|---|---|
| [SEQ ID NO:71] | DH04_H02 ARMIGERA | VHLEDSIDLE | DITAWGYLTK | FGIPEAEKIR | NAEEASSASR |
| [SEQ ID NO:72] | RECH1A PUNCTIGERA | .......... | .......... | .......... | .......... |
| | DH04_H02 ARMIGERA | IVGGSLSSLG | QIPYQAGLVI | DLSGGQAVCG | GSLISASRVL |
| | RECH1A PUNCTIGERA | .......... | .......... | ..A....... | .......... |
| | DH04_H02 ARMIGERA | TAAHCWFDGQ | NQAWRFTVVL | GSTTLFSGGT | RIATSNVVMH |
| | RECH1A PUNCTIGERA | .......... | .......... | .......... | ..P....... |
| | DH04_H02 ARMIGERA | GSWTPSLIRN | DVAVIRLGTN | VGTSNTIAII | ALPSGSQINE |
| | RECH1A PUNCTIGERA | .......... | .......... | .......... | .......... |
| | DH04_H02 ARMIGERA | NFAGETALAS | GFGLTSDSGS | ISSNQALSHV | NLPVITNAVC |
| | RECH1A PUNCTIGERA | .......... | .......T.. | .......... | .......... |
| | DH04_H02 ARMIGERA | RSSFPLLIQD | SNICTSGANG | RSTCRGDSGG | PLVVTRNSRP |
| | RECH1A PUNCTIGERA | .N........ | .......... | .......... | .......N.. |
| | DH04_H02 ARMIGERA | LLIGITSFGS | ARGCQVGSPA | AFARVTSYIS | WINGQ |
| | RECH1A PUNCTIGERA | .......... | .......... | .......... | ..... |

Figure 14

```
                    20         30          40         50         60
                    |          |           |          |          |
BOV CHB   IVNGEDAVPGSWPWQVSLQDSTG--FHFCGGSLISEDWVVTAAHCGVTT-
BOV CHA   .....E..........K..-...........N.N..............
HpCh2A    ..G.STSSLGAF.Y.AG.LANFASGQGV.....LNQRRVL.....WEDGR
HpCh5     .....L...V.QI.....VIDL.G..A........SAS..........Q
                              LOOP 35                     LOOP 60

70         80          90        100
                    |          |           |          |
BOV CHB   ---SDVVVAGEFDQGSSSEKIQKLKIAKVFKNSKYNSLTINNDITLLKL
BOV CHA   --......LET.DT.V...G.....P.FSI.VR........
HpCh2A    NQARSFT..L.SVRLFSGGTRLDTASVVMHGSWNPNLIR--N.IAMIN.
HpCh5     ..WR.....T T........NIP.SN.......S.....V.V.R.
          LOOP 60                                 LOOP 96

110        120         130       140        150
                    |          |           |         |          |
BOV CHB   ATPAQFSETVSAVCLPSADED--FPAGMLCATTGWGKTKY.NA LK-TPD
BOV CHA   S.A.S..Q...........SD.--.A..TT.V.....L.R..TN.AN..
HpCh2A    PSNVATSGNIAPIALPSGNELNNNFNGATATAS.F.LARDG-GSVDGN
HpCh5     GT.....NT..I......SQI.E..A.E..L......TS.T.-.ISS.Q
                                                       LOOP 142

160        170         180       190        200
                    |          |           |         |          |
BOV CHB   KLQQATLPIVSNTDCRKYWGSRVTD-VMICAGA-SGVSSCMGDSGGPLVC
BOV CHA   R..S..LL...N.K....TKIK.-A.......-........
HpCh2A    -LRHVNLPVIT.AV.IVSF.PGIIQSSNI.TSGAN.RT.Q......V
HpCh5     A.S...........RN...LL..D...............
                              LOOP172                   S1A 210        220         230       240
                    |          |           |         |
BOV CHB   QKNGAWTLAGIVSWGSST-CSTSTPAVYARVTALMPWVQETLAAN
BOV CHA   K.......V........... .....G......VN...Q.....
HpCh2B    NS.NRRI.I.VT.F..ARG.QVGS.AAF...TSYIS.INQR.---
HpCh5     TR...P...............................GQ.---
                              S1B              S1C
```

Figure 15

| | | | |
|---|---|---|---|
| [SEQ ID NO:77] | StPOTIB | 1:MESKFAHLIVEFLLALSFETLMARKESDGPEVDELLKEFECNGKQFWPELIGVPTK | 56 |
| [SEQ ID NO:78] | X67950 | 1:MESKFAHLIVEFLLALSFETLMARKESDGPEVDELLKEFECNGKQFWPELIGVPTK | 56 |
| [SEQ ID NO:79] | P01052 | 1:.......................KEFECDGKLQWPELIGVPTK | 20 |
| [SEQ ID NO:80] | M17108 | 1:MESKFAHLIVEFLLALSFETLMARKESDGPEVHELLKEFECNGKQRWPELIGVPTK | 56 |
| [SEQ ID NO:81] | StPOTIA | 1:MESKFAHLIVEFLLALSFETLMARKEGDGSEVIKLLKESESWCGKQFWPELIGVPTK | 60 |
| [SEQ ID NO:82] | K03290 | 1:MESKFAHLIVEFLLALSFETLMARKEIDGPEVIELLKEFDSNLMCEGKQMWPELIGVPTK | 60 |
| [SEQ ID NO:83] | Z12619 | 1:MVKFAHVVAFLLLASLIQPLTARDLEINVLQIFDVSQSGCPGVTKERWPELECTDAK | 56 |
| [SEQ ID NO:84] | X78988 | 1:.......................MSSTECGGGG..GGAKTSWPEWGLSVE | 26 |
| [SEQ ID NO:85] | EILXCH | 1:.......................TEFG...SELKSFPEWGKTVD | 19 |

| | | | |
|---|---|---|---|
| [SEQ ID NO:77] | StPOTIB | 57:LAKEIIEKENSLINNVQILLNGSPVTMDYRCNRVRLFDNILG.SVVQIPRVA | 107 |
| [SEQ ID NO:78] | X67950 | 57:LAKEIIEKENSLINNVQILLNGSPVAMDYRCNRVRLFDNILG.SVVQIPRVA | 107 |
| [SEQ ID NO:79] | P01052 | 21:LAKGIIEKEQNSLITNVHILLNGSPVTMDERCNRVRLFDBILG.SVVQFPRVA | 71 |
| [SEQ ID NO:80] | M17108 | 57:LAKEIIEKENPSINDVPILTNVYRSNRVRLFDNILG.DVVQIPRVM.:106 |
| [SEQ ID NO:81] | StPOTIA | 61:LAKEIIEKENPSITNDPILINGTPVPADERCNRVRLFDNILG.DVVQIPRVA | 111 |
| [SEQ ID NO:82] | K03290 | 61:LAKEIIEKENPSITNDPILISGSPTEDDLCDRVCNRVRLFDNILG.FVVQPVVT | 111 |
| [SEQ ID NO:83] | Z12619 | 57:FAMQIQKENPKITNVQTELNGGPVTEDIRCNRVRLFVNYLD.FLVQTPQHG | 107 |
| [SEQ ID NO:84] | X78988 | 27:DAKVILKDKP.DADLVMLPVGSVVTADYRPNRVRHFVDI...VAQTPHIG | 73 |
| [SEQ ID NO:85] | EILXCH | 20:QAREYFTLHYP.QYDVYFLPEGSPVTEDLRYNRVRVFYNPGTNVVNHMPHVG | 70 |

Figure 24

```
ggatccATGAAACTCTTGGCTGTGACTCTATTGGCTTTCGCCGCGGTCGTCTCCGCGAGG          60
      M  K  L  A  V  T  L  L  A  F  A  A  V  V  S  A  R ggatccATGAAACTCTTGGCTGTGACTCTATTGGCtttcg
FwBacRECH2 Primer-------------------->
                        TTGGCTTTCGCCGCGGTCGTCTCCGCGAGG
                        FwBacRECH2 Primer-------------

Aacgg A tcccaccatcaccatcaccatGTTCACCTCGAGGATTCTATTGATCTGGAAGAT         120
  N  G  S  H  H  H  H  H  H  V  H  L  E  D  S  I  D  L  E  D
Aacgg G tccc
---------->

ATTACCGCTTGGGGATACCTCACCAAATTCGGTATTCCAGAAGCTGAGAAAATCCGCAAC         180
 I  T  A  W  G  Y  L  T  K  F  G  I  P  E  A  E  K  I  R  N

GCTGAAGAAGCTAGCTCTGCTAGCAGGATCGTCGGTGGTTCATTGTCCAGTGTCGGACAG         240
 A  E  E  A  S  S  A  S  R  I  V  G  G  S  L  S  S  V  G  Q

ATCCCTTACCAGGCTGGTCTCGTCATTGACTTAGCAGGTGGCCAGGCTGTCTGCGGAGGC         300
 I  P  Y  Q  A  G  L  V  I  D  L  A  G  G  Q  A  V  C  G  G

TCCCTGATCAGCGCTTCCCGCGTACTGACCGCTGCTCACTGCTGGTTCGACGGCCAAAAC         360
 S  L  I  S  A  S  R  V  L  T  A  A  H  C  W  F  D  G  Q  N

CAGGCCTGGAGATTCACCGTTGTTCTTGGTTCCACCACCTTGTTCTCTGGCGGTACCAGA         420
 Q  A  W  R  F  T  V  V  L  G  S  T  T  L  F  S  G  G  T  R

ATCCCTACATCCAATGTTGTTATGCACGGAAGCTGGACTCCTAGCCTTATCCGTAACGAT         480
 I  P  T  S  N  V  V  M  H  G  S  W  T  P  S  L  I  R  N  D

GTTGCCGTAATCAGATTGGGCACCAACGTAGCAACCTCAAACACCATTGCCATCATCGCT         540
 V  A  V  I  R  L  G  T  N  V  A  T  S  N  T  I  A  I  I  A

CTACCCAGCGGCAGCCAGATCAACGAGAACTTCGCCGGTGAAACCGCCCTCGCCTCCGGC         600
 L  P  S  G  S  Q  I  N  E  N  F  A  G  E  T  A  L  A  S  G

TTCGGTCTCACCAGTGACACCGGCAGCATCTCCAGCAACCAGGCTCTGAGCCACGTCAAC         660
 F  G  L  T  S  D  T  G  S  I  S  S  N  Q  A  L  S  H  V  N

CTGCCAGTGATCACCAACGCTGTGTGCAGAAATTCATTCCCCCTGCTGATCCAGGACTCT         720
 L  P  V  I  T  N  A  V  C  R  N  S  F  P  L  L  I  Q  D  S

AACATTTGCACCAGCGGTGCCAACGGCAGGAGCACTTGCCGCGGTGACTCCGGCGGTCCT         780
 N  I  C  T  S  G  A  N  G  R  S  T  C  R  G  D  S  G  G  P

CTCGTCGTCACCAGGAACAACAGACCACTCTTGATCGGTATCACCTCTTTCGGATCTGCC         840
 L  V  V  T  R  N  N  R  P  L  L  I  G  I  T  S  F  G  S  A

CGCGGTTGCCAAGTTGGATCTCCCGCTGCCTTCGCCAGAGTCACCTCTTACATCAGCTGG         900
 R  G  C  Q  V  G  S  P  A  A  F  A  R  V  T  S  Y  I  S  W

GATCAACGGCCAGCTCTAAaagctt                                           925
 I  N  G  Q  L  *  K  L GATCAACGGCCAGCTCTAAaagctt
<-----------RvRECH Primer
```

Figure 28

SEQUENCE LISTING

<160> NUMBER OF SEQ ID NOS: 93

<210> SEQ ID NO 1
<211> LENGTH: 5
<212> TYPE: PRT
<213> ORGANISM: artificial sequence
<220> FEATURE:
<223> OTHER INFORMATION: linker sequence

<400> SEQUENCE: 1

Glu Glu Lys Lys Asn
1               5

<210> SEQ ID NO 2
<211> LENGTH: 219
<212> TYPE: PRT
<213> ORGANISM: Helicoverpa sp

<400> SEQUENCE: 2

Ile Val Gly Gly Ser Leu Ser Ser Val Gly Gln Ile Pro Tyr Gln Ala
1               5                   10                  15

Gly Leu Val Ile Asp Leu Ala Gly Gly Gln Ala Val Cys Gly Gly Ser
            20                  25                  30

Leu Ile Ser Ala Ser Arg Val Leu Thr Ala Ala His Cys Trp Phe Asp
        35                  40                  45

Gly Gln Asn Gln Ala Trp Arg Phe Thr Val Val Leu Val Met His Gly
    50                  55                  60

Ser Trp Thr Pro Ser Leu Ile Arg Asn Asp Val Ala Val Ile Arg Leu
65                  70                  75                  80

Gly Thr Asn Val Ala Thr Ser Asn Thr Ile Ala Ile Ala Leu Pro
                85                  90                  95

Ser Gly Ser Gln Ile Asn Glu Asn Phe Ala Gly Glu Thr Ala Leu Ala
            100                 105                 110

Ser Gly Phe Gly Leu Thr Ser Asp Thr Gly Ser Ile Ser Ser Asn Gln
        115                 120                 125

Ala Leu Ser His Val Asn Leu Pro Val Ile Thr Asn Ala Val Cys Arg
    130                 135                 140

Asn Ser Phe Pro Leu Leu Ile Gln Asp Ser Asn Ile Cys Thr Ser Gly
145                 150                 155                 160

Ala Asn Gly Arg Ser Thr Cys Arg Gly Asp Ser Gly Gly Pro Leu Val
                165                 170                 175

Val Thr Arg Asn Asn Arg Pro Leu Leu Ile Gly Ile Thr Ser Phe Gly
            180                 185                 190

Ser Ala Arg Gly Cys Gln Val Gly Ser Pro Ala Ala Phe Ala Arg Val
        195                 200                 205

Thr Ser Tyr Ile Ser Trp Ile Asn Gly Gln Leu
    210                 215

<210> SEQ ID NO 3
<211> LENGTH: 40
<212> TYPE: PRT
<213> ORGANISM: Helicoverpa sp

<400> SEQUENCE: 3

Val His Leu Glu Asp Ser Ile Asp Leu Glu Asp Ile Thr Ala Trp Gly
1               5                   10                  15

Tyr Leu Thr Lys Phe Gly Ile Pro Glu Ala Glu Lys Ile Arg Asn Ala

Glu Glu Ala Ser Ser Ala Ser Arg
         35                  40

<210> SEQ ID NO 4
<211> LENGTH: 708
<212> TYPE: DNA
<213> ORGANISM: Helicoverpa sp

<400> SEQUENCE: 4

| | | | | |
|---|---|---|---|---|
| atcgtcggtg | gttcattgtc | cagtgtcgga | cagatcccctt | accaggctgg tctcgtcatt | 60 |
| gacttagcag | gtggccaggc | tgtctgcgga | ggctccctga | tcagcgcttc ccgcgtactg | 120 |
| accgctgctc | actgctggtt | cgacggccaa | accaggcct | ggagattcac cgttgttctt | 180 |
| ggttccacca | ccttgttctc | tggcggtacc | agaatcccta | catccaatgt tgttatgcac | 240 |
| ggaagctgga | ctcctagcct | tatccgtaac | gatgttgccg | taatcagatt gggcaccaac | 300 |
| gtagcaacct | caaacaccat | tgccatcatc | gctctaccca | gcggcagcca gatcaacgag | 360 |
| aacttcgccg | gtgaaaccgc | cctcgcctcc | ggcttcggtc | tcaccagtga caccggcagc | 420 |
| atctccagca | accaggctct | gagccacgtc | aacctgccag | tgatcaccaa cgctgtgtgc | 480 |
| agaaattcat | tccccctgct | gatccaggac | tctaacattt | gcaccagcgg tgccaacggc | 540 |
| aggagcactt | gccgcggtga | ctccggcggt | cctctcgtcg | tcaccaggaa caacagacca | 600 |
| ctcttgatcg | gtatcacctc | tttcggatct | gcccgcggtt | gccaagttgg atctcccgct | 660 |
| gccttcgcca | gagtcaccte | ttacatcage | tggatcaacg | gccagctc | 708 |

<210> SEQ ID NO 5
<211> LENGTH: 120
<212> TYPE: DNA
<213> ORGANISM: Helicoverpa sp

<400> SEQUENCE: 5

| | | | | |
|---|---|---|---|---|
| gttcacctcg | aggattctat | tgatctggaa | gatattaccg | cttggggata cctcaccaaa | 60 |
| ttcggtattc | cagaagctga | gaaaatccgc | aacgctgaag | aagctagctc tgctagcagg | 120 |

<210> SEQ ID NO 6
<211> LENGTH: 921
<212> TYPE: DNA
<213> ORGANISM: Helicoverpa sp

<400> SEQUENCE: 6

| | | | | |
|---|---|---|---|---|
| gttcacctcg | aggattctat | tgatctggaa | gatattaccg | cttggggata cctcaccaaa | 60 |
| ttcggtattc | cagaagctga | gaaaatccgc | aacgctgaag | aagctagctc tgctagcagg | 120 |
| atcgtcggtg | gttcattgtc | cagtgtcgga | cagatcccctt | accaggctgg tctcgtcatt | 180 |
| gacttagcag | gtggccaggc | tgtctgcgga | ggctccctga | tcagcgcttc ccgcgtactg | 240 |
| accgctgctc | actgctggtt | cgacggccaa | accaggcct | ggagattcac cgttgttctt | 300 |
| ggttccacca | ccttgttctc | tggcggtacc | agaatcccta | catccaatgt tgttatgcac | 360 |
| ggaagctgga | ctcctagcct | tatccgtaac | gatgttgccg | taatcagatt gggcaccaac | 420 |
| gtagcaacct | caaacaccat | tgccatcatc | gctctaccca | gcggcagcca gatcaacgag | 480 |
| aacttcgccg | gtgaaaccgc | cctcgcctcc | ggcttcggtc | tcaccagtga caccggcagc | 540 |
| atctccagca | accaggctct | gagccacgtc | aacctgccag | tgatcaccaa cgctgtgtgc | 600 |
| agaaattcat | tccccctgct | gatccaggac | tctaacattt | gcaccagcgg tgccaacggc | 660 |

```
aggagcactt gccgcggtga ctccggcggt cctctcgtcg tcaccaggaa caacagacca    720
ctcttgatcg gtatcacctc tttcggatct gcccgcggtt gccaagttgg atctcccgct    780
gccttcgcca gagtcacctc ttacatcagc tggatcaacg gccagctcta aaatatcgaa    840
cattttgcca tatctacaga gatattttga aatacgttaa tttaaataaa tattttattt    900
attcaaaaaa aaaaaaaaaa a                                              921

<210> SEQ ID NO 7
<211> LENGTH: 32
<212> TYPE: DNA
<213> ORGANISM: artificial sequence
<220> FEATURE:
<223> OTHER INFORMATION: BamHI oligonucleotide primer

<400> SEQUENCE: 7
gaccagccgg atccgatcgg atatgcacca ac                                  32

<210> SEQ ID NO 8
<211> LENGTH: 34
<212> TYPE: DNA
<213> ORGANISM: artificial sequence
<220> FEATURE:
<223> OTHER INFORMATION: HindIII oligonucleotide primer

<400> SEQUENCE: 8
ggagccaagc caagctttga acgcgggcaa actc                                34

<210> SEQ ID NO 9
<211> LENGTH: 36
<212> TYPE: PRT
<213> ORGANISM: artificial sequence
<220> FEATURE:
<223> OTHER INFORMATION: N-terminal sequence of resistant chymotrypsin

<400> SEQUENCE: 9

Ile Val Gly Gly Ser Leu Ser Ser Val Gly Gln Ile Pro Tyr Gln Ala
1               5                   10                  15

Gly Leu Val Ile Asp Leu Ala Gly Gly Gln Ala Val Cys Gly Gly Ser
            20                  25                  30

Leu Ile Ser Ala
        35

<210> SEQ ID NO 10
<211> LENGTH: 29
<212> TYPE: DNA
<213> ORGANISM: artificial sequence
<220> FEATURE:
<223> OTHER INFORMATION: Fw2ResChy primer

<400> SEQUENCE: 10
tcagctgtag ctggagctca agatactcc                                      29

<210> SEQ ID NO 11
<211> LENGTH: 35
<212> TYPE: DNA
<213> ORGANISM: artificial sequence
<220> FEATURE:
<223> OTHER INFORMATION: FwResChym primer

<400> SEQUENCE: 11
gtagctatac tgactctagc tgcagctgga gctgg                               35

<210> SEQ ID NO 12
```

```
<211> LENGTH: 21
<212> TYPE: DNA
<213> ORGANISM: artificial sequence
<220> FEATURE:
<223> OTHER INFORMATION: Hc35PQE-6-Fw primer

<400> SEQUENCE: 12
ttaaccatgg tgatcgacct c                                              21

<210> SEQ ID NO 13
<211> LENGTH: 23
<212> TYPE: DNA
<213> ORGANISM: artificial sequence
<220> FEATURE:
<223> OTHER INFORMATION: Hc35PQ-60-Rv primer

<400> SEQUENCE: 13
gatgagatct gagacgttgg ttg                                            23

<210> SEQ ID NO 14
<211> LENGTH: 25
<212> TYPE: DNA
<213> ORGANISM: artificial sequence
<220> FEATURE:
<223> OTHER INFORMATION: gene specific sense primer

<400> SEQUENCE: 14
cgggatccat ggagtcaaag tttgc                                          25

<210> SEQ ID NO 15
<211> LENGTH: 25
<212> TYPE: DNA
<213> ORGANISM: artificial sequence
<220> FEATURE:
<223> OTHER INFORMATION: gene specific antisense primer

<400> SEQUENCE: 15
gcgtcgacgc ttaagccacc ctagg                                          25

<210> SEQ ID NO 16
<211> LENGTH: 24
<212> TYPE: DNA
<213> ORGANISM: artificial sequence
<220> FEATURE:
<223> OTHER INFORMATION: StPOTIA sense primer

<400> SEQUENCE: 16
cgggatccaa ggaatcggaa tctg                                           24

<210> SEQ ID NO 17
<211> LENGTH: 23
<212> TYPE: DNA
<213> ORGANISM: artificial sequence
<220> FEATURE:
<223> OTHER INFORMATION: StPOTIB sense primer

<400> SEQUENCE: 17
cgggatccaa ggaatttgaa tgc                                            23

<210> SEQ ID NO 18
<211> LENGTH: 22
<212> TYPE: DNA
<213> ORGANISM: artificial sequence
<220> FEATURE:
<223> OTHER INFORMATION: StPOTIA/B antisense primer

<400> SEQUENCE: 18
```
cgagctctta agccaccta gg    22

<210> SEQ ID NO 19
<211> LENGTH: 40
<212> TYPE: DNA
<213> ORGANISM: artificial sequence
<220> FEATURE:
<223> OTHER INFORMATION: FWBacRECH1 (5'-3') primer

<400> SEQUENCE: 19
ttggctttcg ccgcggtcgt ctccgcgagg aacgggtccc    40

<210> SEQ ID NO 20
<211> LENGTH: 40
<212> TYPE: DNA
<213> ORGANISM: artificial sequence
<220> FEATURE:
<223> OTHER INFORMATION: FWBacRECH2 (5'-3') primer

<400> SEQUENCE: 20
ggatccatga aactcttggc tgtgactcta ttggctttcg    40

<210> SEQ ID NO 21
<211> LENGTH: 25
<212> TYPE: DNA
<213> ORGANISM: artificial sequence
<220> FEATURE:
<223> OTHER INFORMATION: RvRECH (3'-5') primer

<400> SEQUENCE: 21
gatcaacggc cagctctaaa agctt    25

<210> SEQ ID NO 22
<211> LENGTH: 53
<212> TYPE: PRT
<213> ORGANISM: Nicotiana alata

<400> SEQUENCE: 22

Met Ala Val His Arg Val Ser Phe Leu Ala Leu Leu Leu Phe Gly
1               5                   10                  15

Met Ser Leu Leu Val Ser Asn Val Glu His Ala Asp Ala Lys Ala Cys
            20                  25                  30

Thr Leu Asn Cys Asp Pro Arg Ile Ala Tyr Gly Val Cys Pro Arg Ser
        35                  40                  45

Glu Glu Lys Lys Asn
    50

<210> SEQ ID NO 23
<211> LENGTH: 58
<212> TYPE: PRT
<213> ORGANISM: Nicotiana alata

<400> SEQUENCE: 23

Asp Arg Ile Cys Thr Asn Cys Cys Ala Gly Thr Lys Gly Cys Lys Tyr
1               5                   10                  15

Phe Ser Asp Asp Gly Thr Phe Val Cys Glu Gly Glu Ser Asp Pro Arg
            20                  25                  30

Asn Pro Lys Ala Cys Thr Leu Asn Cys Asp Pro Arg Ile Ala Tyr Gly
        35                  40                  45

Val Cys Pro Arg Ser Glu Glu Lys Lys Asn
    50                  55

```
<210> SEQ ID NO 24
<211> LENGTH: 58
<212> TYPE: PRT
<213> ORGANISM: Nicotiana alata

<400> SEQUENCE: 24

Asp Arg

-continued

<210> SEQ ID NO 28
<211> LENGTH: 36
<212> TYPE: PRT
<213> ORGANISM: Helicoverpa sp

<400> SEQUENCE: 28

Ile Val Gly Gly Ser Leu Ser Ser Val Gly Gln Ile Pro Tyr Gln Ala
1               5                   10                  15

Gly Leu Val Ile Asp Leu Ala Gly Gly Gln Ala Val Cys Gly Gly Ser
            20                  25                  30

Leu Ile Ser Ala
        35

<210> SEQ ID NO 29
<211> LENGTH: 29
<212> TYPE: PRT
<213> ORGANISM: Helicoverpa sp

<400> SEQUENCE: 29

Ile Val Gly Gly Ser Ile Ser Ser Ile Gly Gln Ile Pro Tyr Gly Ala
1               5                   10                  15

Gly Leu Val Ile Asp Phe Ala Gly Gly Gln Ala Val Cys
            20                  25

<210> SEQ ID NO 30
<211> LENGTH: 29
<212> TYPE: PRT
<213> ORGANISM: Helicoverpa sp

<400> SEQUENCE: 30

Ile Val Gly Gly Ser Thr Ser Ser Val Gly Gln Phe Pro Tyr Gln Ala
1               5                   10                  15

Gly Leu Leu Ala Ser Phe Ala Gly Gly Gln Ala Val Cys
            20                  25

<210> SEQ ID NO 31
<211> LENGTH: 29
<212> TYPE: PRT
<213> ORGANISM: Helicoverpa sp

<400> SEQUENCE: 31

Ile Val Gly Gly Ser Val Thr Thr Leu Asp Ala Tyr Pro Thr Ile Ala
1               5                   10                  15

Gly Leu Val Tyr Asn Phe Ala Gly Gly Gln Ala Val Cys
            20                  25

<210> SEQ ID NO 32
<211> LENGTH: 295
<212> TYPE: PRT
<213> ORGANISM: Helicoverpa armigera

<400> SEQUENCE: 32

Met Lys Leu Leu Ala Val Thr Leu Leu Ala Phe Ala Ala Val Val Ser
1               5                   10                  15

Ala Arg Asn Ile Asp Leu Glu Asp Val Ile Asp Leu Glu Asp Ile Thr
            20                  25                  30

Ala Tyr Asp Tyr His Thr Lys Ile Gly Ile Pro Leu Ala Glu Lys Ile
        35                  40                  45

Arg Ala Ala Glu Glu Glu Ala Glu Arg Asn Pro Ser Arg Ile Val Gly
    50                  55                  60

```
Gly Ser Thr Ser Ser Leu Gly Ala Phe Pro Tyr Gln Ala Gly Leu Leu
65                  70                  75                  80

Ala Thr Phe Ala Ser Gly Gln Gly Val Cys Gly Gly Ser Leu Leu Asn
                85                  90                  95

Asn Arg Arg Val Leu Thr Ala Ala His Cys Trp Phe Asp Gly Arg Asn
            100                 105                 110

Gln Ala Arg Ser Phe Thr Val Val Leu Gly Ser Val Arg Leu Phe Ser
            115                 120                 125

Gly Gly Thr Arg Leu Asn Thr Ala Ser Val Val Met His Gly Ser Trp
130                 135                 140

Asn Pro Asn Leu Ile Arg Asn Asp Ile Ala Met Ile Asn Leu Pro Ser
145                 150                 155                 160

Asn Val Ala Thr Ser Gly Asn Ile Ala Pro Ile Ala Leu Pro Ser Gly
                165                 170                 175

Asn Glu Leu Asn Asn Asn Phe Asn Gly Ala Thr Ala Val Ala Ser Gly
            180                 185                 190

Phe Gly Leu Ala Arg Asp Gly Gly Ser Val Asp Gly Asn Leu Arg His
            195                 200                 205

Val Asn Leu Pro Val Ile Thr Asn Ala Val Cys Thr Val Ser Phe Pro
210                 215                 220

Gly Ile Ile Gln Ser Ser Asn Ile Cys Thr Ser Gly Ala Asn Gly Arg
225                 230                 235                 240

Ser Thr Cys Gln Gly Asp Ser Gly Gly Pro Leu Val Val Thr Ser Asn
                245                 250                 255

Asn Arg Arg Ile Leu Ile Gly Val Thr Ser Phe Gly Ser Ala Arg Gly
            260                 265                 270

Cys Gln Val Gly Ser Pro Ala Ala Phe Ala Arg Val Thr Ser Phe Ile
            275                 280                 285

Ser Trp Ile Asn Gln Arg Leu
290                 295

<210> SEQ ID NO 33
<211> LENGTH: 292
<212> TYPE: PRT
<213> ORGANISM: Helicoverpa armigera

<400> SEQUENCE: 33

Leu Ala Val Thr Leu Leu Ala Phe Ala Ala Val Val Ser Ala Arg Asn
1               5                   10                  15

Ile Asp Leu Glu Asp Val Ile Asp Leu Glu Asp Ile Thr Ala Tyr Asp
                20                  25                  30

Tyr His Thr Lys Ile Gly Ile Pro Leu Ala Glu Lys Ile Arg Ala Ala
            35                  40                  45

Glu Glu Glu Ala Glu Arg Asn Pro Ser Arg Ile Val Gly Gly Ser Thr
50                  55                  60

Ser Ser Leu Gly Ala Phe Pro Tyr Gln Ala Gly Leu Leu Ala Thr Phe
65                  70                  75                  80

Ala Ser Gly Gln Gly Val Cys Gly Gly Ser Leu Leu Asn Asn Arg Arg
                85                  90                  95

Val Leu Thr Ala Ala His Cys Trp Phe Asp Gly Arg Asn Gln Ala Arg
            100                 105                 110

Ser Phe Thr Val Val Leu Gly Ser Val Arg Leu Phe Ser Gly Gly Thr
            115                 120                 125

Arg Leu Asn Thr Ala Ser Val Val Met His Gly Ser Trp Asn Pro Asn
```

```
            130                 135                 140
Leu Ile Arg Asn Asp Ile Ala Met Ile Asn Leu Pro Ser Asn Val Ala
145                 150                 155                 160

Thr Ser Gly Asn Ile Ala Pro Ile Ala Leu Pro Ser Gly Asn Glu Leu
                165                 170                 175

Asn Asn Asn Phe Asn Gly Ala Thr Ala Val Ala Ser Gly Phe Gly Leu
            180                 185                 190

Ala Arg Asp Gly Gly Ser Val Asp Gly Asn Leu Arg His Val Asn Leu
        195                 200                 205

Pro Val Ile Thr Asn Ala Val Cys Thr Val Ser Phe Pro Gly Ile Ile
210                 215                 220

Gln Ser Ser Asn Ile Cys Thr Ser Gly Ala Asn Gly Arg Gly Thr Cys
225                 230                 235                 240

Gln Gly Asp Ser Gly Gly Pro Leu Val Val Thr Ser Asn Asn Arg Arg
                245                 250                 255

Ile Leu Ile Gly Val Thr Pro Phe Gly Ser Ala Arg Gly Cys Gln Val
            260                 265                 270

Gly Ser Pro Ala Ala Phe Ala Arg Val Thr Ser Phe Ile Ser Trp Ile
        275                 280                 285

Asn Gln Arg Leu
    290

<210> SEQ ID NO 34
<211> LENGTH: 295
<212> TYPE: PRT
<213> ORGANISM: Helicoverpa armigera

<400> SEQUENCE: 34

Met Lys Leu Leu Ala Val Thr Leu Leu Ala Phe Ala Ala Ile Val Ser
1               5                   10                  15

Ala Arg Asn Ile Asp Leu Glu Asp Val Ile Asp Leu Glu Asp Ile Thr
            20                  25                  30

Ala Tyr Asp Tyr His Thr Lys Ile Gly Ile Pro Leu Ala Glu Lys Ile
        35                  40                  45

Arg Ala Ala Glu Glu Ala Glu Arg Asn Pro Ser Arg Ile Val Gly
    50                  55                  60

Gly Ser Ile Ser Ser Leu Gly Ala Phe Pro Tyr Gln Ala Gly Leu Leu
65                  70                  75                  80

Ala Thr Phe Ala Ser Gly Gln Gly Val Cys Gly Gly Ser Leu Leu Asn
                85                  90                  95

Asn Arg Arg Val Leu Thr Ala Ala His Cys Trp Phe Asp Gly Arg Asn
            100                 105                 110

Gln Ala Arg Ser Phe Thr Val Val Leu Gly Ser Val Arg Leu Phe Ser
        115                 120                 125

Gly Gly Thr Arg Leu Asn Thr Ala Ser Val Val Met His Gly Ser Trp
    130                 135                 140

Asn Pro Asn Leu Ile Arg Asn Asp Ile Ala Ile Asn Leu Pro Ser
145                 150                 155                 160

Asn Val Ala Thr Ser Gly Asn Ile Ala Pro Ile Ala Leu Pro Ser Gly
                165                 170                 175

Asn Glu Leu Asn Asn Asn Phe Asn Gly Ala Thr Ala Val Ala Ser Gly
            180                 185                 190

Phe Gly Leu Ala Asn Asp Gly Gly Ser Val Asp Gly Asn Leu Arg His
        195                 200                 205
```

```
Val Asn Leu Pro Val Ile Thr Asn Ala Val Cys Thr Val Ser Phe Pro
    210                 215                 220

Gly Ile Ile Gln Ser Ser Asn Ile Cys Thr Ser Gly Ala Asn Gly Arg
225                 230                 235                 240

Ser Thr Cys Gln Gly Asp Ser Gly Gly Pro Leu Val Val Thr Ser Asn
                245                 250                 255

Asn Arg Arg Ile Leu Ile Gly Val Thr Ser Phe Gly Ser Ala Arg Gly
            260                 265                 270

Cys Gln Val Gly Ser Pro Ala Ala Phe Ala Arg Val Thr Ser Phe Ile
        275                 280                 285

Ser Trp Ile Asn Asn Leu Leu
    290                 295

<210> SEQ ID NO 35
<211> LENGTH: 276
<212> TYPE: PRT
<213> ORGANISM: Helicoverpa armigera

<400> SEQUENCE: 35

Ile Asn His Glu Ala Val Val Asp Leu Glu Asp Ile Thr Ala Tyr Gly
1               5                   10                  15

Tyr His Thr Lys Val Gly Ile Pro Leu Ala Glu Glu Ile Arg Ile Ala
            20                  25                  30

Glu Leu Glu Ala Ser Arg Asn Pro Ser Arg Ile Val Gly Gly Ser Ser
        35                  40                  45

Ala Ser Leu Gly Gln Phe Pro Tyr Gln Ala Gly Leu Leu Ile Asn Leu
    50                  55                  60

Pro Leu Gly Gln Ser Val Cys Gly Gly Ser Leu Leu Asn Gln Arg Arg
65                  70                  75                  80

Val Leu Thr Ala Ala His Cys Trp Phe Asp Gly Arg Asn Gln Ala Asn
                85                  90                  95

Ser Leu Thr Val Ile Leu Gly Ser Ile Asn Leu Tyr Phe Gly Gly Thr
            100                 105                 110

Arg Leu Asn Ser Asn Ser Val Val Met His Gly Ser Trp Asn Pro Asn
        115                 120                 125

Leu Ile Arg Asn Asp Ile Ala Ile Ile Asn Leu Pro Ser Asn Val Gly
    130                 135                 140

Thr Ser Asn Asn Ile Ala Pro Ile Ala Leu Pro Ser Gly Asn Glu Leu
145                 150                 155                 160

Asn Asn Gln Phe Ala Gly Phe Thr Ala Thr Ala Ser Gly Phe Gly Arg
                165                 170                 175

Thr Arg Asp Gly Gly Ser Val Ser Pro Thr Leu Asn His Val Asn Leu
            180                 185                 190

Pro Val Ile Thr Asn Asn Val Cys Trp Gln Ser Phe Pro Leu Tyr Ile
        195                 200                 205

Gln Ser Ser Asn Ile Cys Thr Ser Gly Ala Asn Gly Arg Ser Thr Cys
    210                 215                 220

Gln Gly Asp Ser Gly Gly Pro Leu Val Val Thr Ser Asn Asn Arg Arg
225                 230                 235                 240

Ile Leu Ile Gly Val Thr Ser Phe Gly Ser Asp Arg Gly Cys Gln Val
                245                 250                 255

Gly Ala Pro Ala Ala Phe Ala Arg Val Thr Ser Tyr Ile Ser Trp Ile
            260                 265                 270

Asn Gln Arg Leu
    275
```

<210> SEQ ID NO 36
<211> LENGTH: 292
<212> TYPE: PRT
<213> ORGANISM: Helicoverpa armigera

<400> SEQUENCE: 36

Met Lys Leu Phe Leu Gly Val Cys Leu Thr Leu Ala Val Ala Val Ser
1               5                   10                  15

Ala Val Glu Ile Ala Thr Pro Asp Ala Asp Ser Pro Val Phe Gly Tyr
            20                  25                  30

His Ala Lys Phe Gly Ile Ala Glu Ala Ala Arg Ile Lys Ser Ala Glu
        35                  40                  45

Glu Val Gln Ser Phe Asn Gly Gln Arg Ile Val Gly Gly Ser Ile Thr
    50                  55                  60

Asn Ile Ala Asn Val Pro Tyr Gln Ala Gly Leu Val Ile Thr Ile Phe
65                  70                  75                  80

Ile Phe Gln Ser Val Cys Gly Ala Ser Leu Ile Ser His Asn Arg Leu
                85                  90                  95

Val Thr Ala Ala His Cys Lys Ser Asp Gly Val Leu Thr Ala Asn Ser
            100                 105                 110

Phe Thr Val Val Leu Gly Ser Asn Thr Leu Phe Phe Gly Gly Thr Arg
        115                 120                 125

Ile Asn Thr Asn Asp Val Val Met His Pro Asn Trp Asn Pro Asn Thr
    130                 135                 140

Ala Ala Asn Asp Ile Ala Val Leu Arg Ile Ser Ser Val Ser Phe Ser
145                 150                 155                 160

Asn Val Ile Gln Pro Ile Ala Leu Pro Ser Gly Asp Glu Leu Asn Asn
                165                 170                 175

Leu Phe Val Gly Ala Asn Ala Leu Ala Ser Gly Phe Gly Arg Thr Ser
            180                 185                 190

Asp Ser Gly Ser Ile Gly Thr Asn Gln Gln Leu Ser Ser Val Thr Ile
        195                 200                 205

Pro Val Ile Thr Asn Ala Gln Cys Ala Ala Val Tyr Gly Ser Gly Phe
    210                 215                 220

Val His Ala Ser Asn Ile Cys Thr Ser Gly Ala Gly Gly Lys Gly Thr
225                 230                 235                 240

Cys Asn Gly Asp Ser Gly Gly Pro Leu Ala Val Asp Ser Asn Asn Arg
                245                 250                 255

Lys Ile Leu Ile Gly Val Thr Ser Tyr Gly Ala Gln Ala Gly Cys Ala
            260                 265                 270

Ala Gly Phe Pro Ala Ala Phe Ala Arg Val Thr Ser Phe Val Asp Trp
        275                 280                 285

Val Gln Ser Gln
    290

<210> SEQ ID NO 37
<211> LENGTH: 257
<212> TYPE: PRT
<213> ORGANISM: Helicoverpa armigera

<400> SEQUENCE: 37

His Asn Lys Trp Val Leu Thr Ala Ala His Cys Leu Ala Asn Arg Ile
1               5                   10                  15

Thr Phe Val Val Arg Phe Gly Leu Thr Asn Leu Thr Arg Pro Glu Ile
            20                  25                  30

```
Leu Val Glu Ser Ala Asn Lys Tyr Ile His Pro Asp Tyr Asp Glu Ile
            35                  40                  45

Arg Ala Gly Val Gln Thr Ala Asp Leu Ala Leu Val Gly Leu Asp His
        50                  55                  60

His Ile Glu Tyr Ser Ala Asn Val Gln Pro Ser Arg Leu Met Ser Ser
65                  70                  75                  80

Ala Gln Lys Asn Ile Asn Tyr Glu Gly Ile Gln Met Ile Val Ser Gly
                85                  90                  95

Phe Gly Arg Thr Asp Asp Leu Trp Asn Gly Ala Ala Ser Glu Ile
            100                 105                 110

Leu Leu Trp Val Tyr Gln Arg Gly Val Ser Asn Glu Glu Cys Leu Arg
        115                 120                 125

Trp Tyr Pro Thr Ser Gln Val Ile Lys Glu Glu Thr Ile Cys Ala Gly
    130                 135                 140

Tyr Trp Asp Asn Pro Ser Gln Ser Ser Cys Gln Gly Asp Ser Gly Gly
145                 150                 155                 160

Pro Leu Thr Ile Ile Asp Ala Asp Gly Glu Arg Thr Gln Val Gly Ile
                165                 170                 175

Val Ser Phe Gly Ser Thr Ala Gly Cys Asn Ser Pro Phe Pro Ser Gly
            180                 185                 190

Tyr Val Arg Pro Gly His Tyr His Asp Trp Phe Thr Glu Val Thr Gly
        195                 200                 205

Ile Asn Phe Asp Trp Asp Ser Asp Ala Ile Ile Pro Gly Ser Ser Glu
    210                 215                 220

Ser Glu Glu Asp Gly Ser Asn Pro Ser Ser Glu Glu Asp Ala Gly Ser
225                 230                 235                 240

Pro Pro Ser Glu Glu Glu Glu Ala Pro Glu Lys Val Arg Val Val Glu
                245                 250                 255

Tyr

<210> SEQ ID NO 38
<211> LENGTH: 19
<212> TYPE: DNA
<213> ORGANISM: artificial sequence
<220> FEATURE:
<223> OTHER INFORMATION: FWG1 primer

<400> SEQUENCE: 38
tcccttacca ggcgctgtc                                            19

<210> SEQ ID NO 39
<211> LENGTH: 18
<212> TYPE: DNA
<213> ORGANISM: artificial sequence
<220> FEATURE:
<223> OTHER INFORMATION: RVG4 primer

<400> SEQUENCE: 39
tctggcgaag gcagcagg                                             18

<210> SEQ ID NO 40
<211> LENGTH: 20
<212> TYPE: DNA
<213> ORGANISM: artificial sequence
<220> FEATURE:
<223> OTHER INFORMATION: Y79Fw primer

<400> SEQUENCE: 40
```

```
ctgctagcct cggacaattc                                              20
```

<210> SEQ ID NO 41
<211> LENGTH: 20
<212> TYPE: DNA
<213> ORGANISM: artificial sequence
<220> FEATURE:
<223> OTHER INFORMATION: Y72Fw primer

<400> SEQUENCE: 41

```
ctggagtgca gactgctgac                                              20
```

<210> SEQ ID NO 42
<211> LENGTH: 20
<212> TYPE: DNA
<213> ORGANISM: artificial sequence
<220> FEATURE:
<223> OTHER INFORMATION: Y72Rv primer

<400> SEQUENCE: 42

```
ggatgatggc gtcgctgtcc                                              20
```

<210> SEQ ID NO 43
<211> LENGTH: 213
<212> TYPE: PRT
<213> ORGANISM: Helicoverpa punctigera

<400> SEQUENCE: 43

Pro Tyr Gln Ala Gly Leu Val Ile Thr Ile Phe Ile Phe Gln Ser Val
1               5                   10                  15

Cys Gly Ala Ser Leu Ile Pro His Asn Arg Leu Val Thr Ala Ala His
            20                  25                  30

Cys Lys Ser Asp Gly Val Leu Thr Ala Asn Ser Phe Thr Val Val Leu
        35                  40                  45

Gly Ser Asn Thr Leu Phe Phe Gly Gly Thr Arg Ile Asn Thr Asn Asp
    50                  55                  60

Val Val Met His Pro Asn Trp Asn Pro Ser Thr Ala Ala Asn Asp Ile
65                  70                  75                  80

Ala Val Met Arg Ile Ser Ser Val Ser Phe Ser Asn Val Ile Gln Pro
                85                  90                  95

Ile Ala Leu Pro Ser Gly Asp Glu Leu Asn Asn Leu Phe Val Gly Ala
            100                 105                 110

Asn Ala Leu Ala Ser Gly Phe Gly Arg Thr Ser Asp Gly Gly Ser Ile
        115                 120                 125

Gly Ser Asn Gln Gln Val Ser Ser Val Thr Ile Pro Val Ile Thr Asn
    130                 135                 140

Asp Glu Cys Ala Ala Val Tyr Gly Ser Ala Phe Val His Ser Ser Asn
145                 150                 155                 160

Ile Cys Thr Ser Gly Ala Gly Gly Lys Gly Thr Cys Asn Gly Asp Ser
                165                 170                 175

Gly Gly Pro Leu Ala Ile Asp Ser Asn Asn Glu Lys Ile Leu Ile Gly
            180                 185                 190

Val Thr Ser Tyr Gly Ala Gln Ala Gly Cys Ala Ala Gly Leu Pro Ala
        195                 200                 205

Ala Phe Ala Arg Lys
    210

<210> SEQ ID NO 44
<211> LENGTH: 213

```
<212> TYPE: PRT
<213> ORGANISM: Helicoverpa punctigera

<400> SEQUENCE: 44

Pro Tyr Gln Ala G

-continued

Val Asp Gly Asn Leu Arg His Val Asn Leu Pro Val Ile Thr Asn Ala
    130                 135                 140

Val Cys Thr Val Ser Phe Pro Gly Ile Ile Gln Ser Ser Asn Ile Cys
145                 150                 155                 160

Thr Ser Gly Ala Asn Gly Arg Ser Thr Cys Gln Gly Asp Ser Gly Gly
                165                 170                 175

Pro

<210> SEQ ID NO 46
<211> LENGTH: 217
<212> TYPE: PRT
<213> ORGANISM: Helicoverpa punctigera

<400> SEQUENCE: 46

Ser Ala Ser Leu Gly Gln Phe Pro Tyr Gln Ala Gly Leu Leu Ile Asn
1               5                   10                  15

Leu Pro Leu Gly Gln Ser Val Cys Gly Gly Ser Leu Leu Asn Gln Arg
            20                  25                  30

Arg Val Leu Thr Ala Ala His Cys Trp Phe Asp Gly Arg Asn Gln Ala
        35                  40                  45

Thr Ser Leu Thr Val Ile Leu Gly Ser Ile Asn Leu Phe Phe Gly Gly
    50                  55                  60

Thr Arg Leu Asn Ser Asn Ser Val Val Met His Gly Ser Trp Asn Pro
65                  70                  75                  80

Asn Leu Ile Arg Asn Asp Ile Ala Ile Ile Asn Leu Pro Ser Asn Val
                85                  90                  95

Gly Thr Ser Gly Asn Ile Ala Pro Ile Ala Leu Pro Ser Gly Asn Glu
            100                 105                 110

Leu Asn Asn Gln Phe Ala Gly Phe Thr Ala Thr Ala Ser Gly Phe Gly
        115                 120                 125

Leu Thr Arg Asp Gly Gly Asn Val Ser Pro Thr Leu Asn His Val Asn
    130                 135                 140

Leu Pro Val Ile Thr Asn Asn Val Cys Trp Gln Ser Phe Pro Leu Tyr
145                 150                 155                 160

Ile Gln Ser Thr Asn Ile Cys Thr Ser Gly Ala Asn Gly Arg Gly Thr
                165                 170                 175

Cys Gln Gly Asp Ser Gly Gly Pro Leu Val Val Thr Ser Asn Asn Arg
            180                 185                 190

Arg Ile Leu Ile Gly Val Thr Ser Phe Gly Ser Asp Arg Gly Cys Gln
        195                 200                 205

Val Gly Ala Pro Ala Ala Phe Ala Arg
    210                 215

<210> SEQ ID NO 47
<211> LENGTH: 170
<212> TYPE: PRT
<213> ORGANISM: Helicoverpa punctigera

<400> SEQUENCE: 47

Ser Gly Val Gln Thr Ala Asp Leu Ala Leu Val Gly Leu Asp Gln Glu
1               5                   10                  15

Ile Glu Tyr Ser Ala Asn Val Gln Pro Ser Arg Leu Met Ser Ser Ala
            20                  25                  30

Gln Lys Asn Ile Asn Tyr Glu Gly Ile Gln Met Ile Val Ser Gly Phe
        35                  40                  45

Gly Arg Thr Asp Asp Leu Trp Asn Gly Gly Ala Ala Ser Glu Ile Leu

```
                50                  55                  60
Leu Trp Val Tyr Gln Arg Gly Val Ser Asn Glu Glu Cys Leu Arg Trp
 65                  70                  75                  80

Tyr Pro Thr Ser Gln Val Ile Lys Glu Gln Thr Ile Cys Ala Gly Tyr
                 85                  90                  95

Trp Asp Asn Pro Ser Gln Ser Ser Cys Gln Gly Asp Ser Gly Gly Pro
                100                 105                 110

Leu Thr Ile Ile Asp Ala Asp Gly Glu Arg Thr Gln Val Gly Ile Val
                115                 120                 125

Ser Phe Gly Ser Thr Ala Gly Cys Asn Ser Pro Phe Pro Ser Gly Tyr
                130                 135                 140

Val Arg Pro Gly His Tyr His Asp Trp Phe Thr Glu Val Thr Gly Ile
145                 150                 155                 160

Asn Phe Asp Trp Asp Ser Asp Ala Ile Ile
                165                 170

<210> SEQ ID NO 48
<211> LENGTH: 279
<212> TYPE: PRT
<213> ORGANISM: Helicoverpa punctigera

<400> SEQUENCE: 48

Ala Val Ser Ala Val Glu Ile Gly Thr Pro Asp Ala Asp Ser Pro Val
 1               5                  10                  15

Phe Gly Tyr His Ala Lys Phe Gly Ile Pro Glu Ala Ala Arg Ile Lys
                 20                  25                  30

Ser Ala Glu Glu Val Gln Ser Phe Asn Gly Gln Arg Ile Val Gly Gly
             35                  40                  45

Ser Ile Thr Asp Ile Ala Asn Val Pro Tyr Gln Ala Gly Leu Val Ile
         50                  55                  60

Thr Ile Phe Ile Phe Gln Ser Val Cys Gly Ala Ser Leu Ile Ser His
 65                  70                  75                  80

Asn Arg Leu Val Thr Ala Ala His Cys Lys Ser Asp Gly Val Leu Thr
                 85                  90                  95

Ala Asn Ser Phe Thr Val Val Leu Gly Ser Asn Thr Leu Phe Phe Gly
                100                 105                 110

Gly Thr Arg Ile Asn Thr Asn Asp Val Val Met His Pro Asn Trp Asn
             115                 120                 125

Pro Ser Thr Ala Ala Asn Asp Ile Ala Val Met Arg Ile Ser Ser Val
         130                 135                 140

Ser Phe Ser Asn Val Ile Gln Pro Ile Ala Leu Pro Ser Gly Asp Glu
145                 150                 155                 160

Leu Asn Asn Leu Phe Val Gly Ala Asn Ala Leu Ala Ser Gly Phe Gly
                165                 170                 175

Arg Thr Ser Asp Gly Gly Ser Ile Gly Ser Asn Gln Gln Val Ser Ser
                180                 185                 190

Val Thr Ile Pro Val Ile Thr Asn Asp Glu Cys Ala Ala Val Tyr Gly
             195                 200                 205

Ser Ala Phe Val His Ser Ser Asn Ile Cys Thr Ser Gly Ala Gly Gly
         210                 215                 220

Lys Gly Thr Cys Asn Gly Asp Ser Gly Gly Pro Leu Ala Val Asp Ser
225                 230                 235                 240

Asn Asn Glu Lys Ile Leu Ile Gly Val Thr Ser Tyr Gly Ala Gln Ala
                245                 250                 255
```

```
Gly Cys Ala Val Gly Leu Pro Ala Ala Phe Ala Arg Val Thr Ser Phe
        260                 265                 270
Val Ser Trp Val Gln Ser Gln
        275

<210> SEQ ID NO 49
<211> LENGTH: 292
<212> TYPE: PRT
<213> ORGANISM: Helicoverpa punctigera

<400> SEQUENCE: 49

Met Lys Leu Phe Leu Gly Val Cys Leu Ala Leu Ala Val Ala Val Ser
1               5                   10                  15
Ala Val Glu Ile Gly Thr Pro Glu Ala Gly Ser Pro Val Phe Gly Tyr
            20                  25                  30
His Ala Lys Phe Gly Ile Ala Glu Ala Ala Arg Ile Lys Ser Ala Glu
        35                  40                  45
Glu Val Gln Ser Phe Asn Gly Gln Arg Ile Val Gly Gly Ser Ile Thr
    50                  55                  60
Asn Ile Ala Asn Val Pro Tyr Gln Ala Gly Leu Val Ile Thr Ile Phe
65                  70                  75                  80
Ile Phe Gln Ser Val Cys Gly Ala Ser Leu Ile Ser His Asn Arg Leu
                85                  90                  95
Val Thr Ala Ala His Cys Lys Phe Asp Gly Val Met Thr Ala Asn Ser
            100                 105                 110
Phe Thr Val Val Leu Gly Ser Asn Thr Leu Phe Phe Gly Gly Thr Arg
        115                 120                 125
Ile Asn Thr Asn Asp Val Val Met His Pro Asn Trp Asn Pro Ser Thr
    130                 135                 140
Val Ala Asn Asp Ile Ala Val Ile Arg Ile Ser Ser Ile Val Tyr Asn
145                 150                 155                 160
Asn Val Ile Gln Pro Ile Ala Leu Pro Ser Gly Asp Glu Leu Asp Asn
                165                 170                 175
Leu Phe Val Gly Ala Asn Ala Leu Ala Ser Gly Phe Gly Arg Thr Ser
            180                 185                 190
Asp Ser Gly Gly Ile Gly Thr Asn Gln Gln Leu Ser Ser Val Thr Ile
        195                 200                 205
Pro Val Ile Thr Asn Ala Glu Cys Ala Ala Val Tyr Gly Pro Ala Phe
    210                 215                 220
Val His Asp Thr Asn Ile Cys Thr Ser Gly Ala Gly Gly Lys Gly Thr
225                 230                 235                 240
Cys Asn Gly Asp Ser Gly Gly Pro Leu Ala Val Asp Ser Asn Asp Lys
                245                 250                 255
Lys Ile Leu Ile Gly Val Thr Ser Tyr Gly Ala Ala Asp Gly Cys Ala
            260                 265                 270
Ala Gly Phe Pro Ala Ala Phe Ala Arg Val Thr Ser Phe Val Ser Trp
        275                 280                 285
Val Gln Ser Gln
    290

<210> SEQ ID NO 50
<211> LENGTH: 295
<212> TYPE: PRT
<213> ORGANISM: Helicoverpa punctigera

<400> SE

```
Met Lys Leu Leu Ala Val Thr Leu Leu Ala Phe Ala Ala Val Val Ser
1               5                   10                  15

Ala Arg Asn Ile Asp Leu Glu Asp Val Ile Asp Leu Glu Asp Ile Thr
            20                  25                  30

Ala Tyr Asp Tyr His Thr Lys Ile Gly Ile Pro Leu Ala Glu Glu Ile
        35                  40                  45

Arg Ala Ala Glu Glu Glu Ala Glu Arg Asp Pro Ser Arg Ile Val Gly
    50                  55                  60

Gly Ser Thr Ser Ser Leu Gly Ala Phe Pro Tyr Gln Ala Gly Leu Leu
65                  70                  75                  80

Ala Asn Phe Ala Ser Gly Gln Gly Val Cys Gly Gly Ser Leu Leu Asn
                85                  90                  95

Gln Arg Arg Val Leu Thr Ala Ala His Cys Trp Phe Asp Gly Arg Asn
            100                 105                 110

Gln Ala Arg Ser Phe Thr Val Val Leu Gly Ser Val Arg Leu Phe Ser
        115                 120                 125

Gly Gly Thr Arg Leu Asp Thr Ala Ser Val Val Met His Gly Ser Trp
    130                 135                 140

Asn Pro Asn Leu Ile Arg Asn Asp Ile Ala Met Ile Asn Leu Pro Ser
145                 150                 155                 160

Asn Val Ala Thr Ser Gly Asn Ile Ala Pro Ile Ala Leu Pro Ser Gly
                165                 170                 175

Asn Glu Leu Asn Asn Asn Phe Asn Gly Ala Thr Ala Thr Ala Ser Gly
            180                 185                 190

Phe Gly Leu Ala Arg Asp Gly Gly Ser Val Asp Gly Asn Leu Arg His
        195                 200                 205

Val Asn Leu Pro Val Ile Thr Asn Ala Val Cys Thr Val Ser Phe Pro
    210                 215                 220

Gly Ile Ile Gln Ser Ser Asn Ile Cys Thr Ser Gly Ala Asn Gly Arg
225                 230                 235                 240

Ser Thr Cys Gln Gly Asp Ser Gly Gly Pro Leu Val Val Asn Ser Asn
                245                 250                 255

Asn Arg Arg Ile Leu Ile Gly Val Thr Ser Phe Gly Ser Ala Arg Gly
            260                 265                 270

Cys Gln Val Gly Ser Pro Ala Ala Phe Ala Arg Val Thr Ser Phe Ile
        275                 280                 285

Ser Trp Ile Asn Gln Arg Leu
    290                 295

<210> SEQ ID NO 51
<211> LENGTH: 295
<212> TYPE: PRT
<213> ORGANISM: Helicoverpa punctigera

<400> SEQUENCE: 51

Met Lys Leu Leu Ala Val Thr Leu Leu Ala Phe Ala Ala Val Val Ser
1               5                   10                  15

Ala Arg Asn Ile Asp Leu Glu Asp Val Ile Asp Leu Glu Asp Ile Thr
            20                  25                  30

Ala Tyr Asp Tyr His Thr Lys Ile Gly Ile Pro Leu Ala Glu Lys Ile
        35                  40                  45

Arg Ala Ala Glu Glu Glu Ala Glu Arg Asn Pro Ser Arg Ile Val Gly
    50                  55                  60

Gly Ser Thr Ser Ser Leu Gly Ala Phe Pro Tyr Gln Ala Gly Leu Leu
65                  70                  75                  80
```

```
Ala Ser Phe Ala Ser Gly Gln Gly Val Cys Gly Gly Ser Leu Leu Asn
                85                  90                  95

Val Arg Arg Val Leu Thr Ala Ala His Cys Trp Phe Asp Gly Arg Asn
                100                 105                 110

Gln Ala Arg Ser Phe Thr Val Leu Gly Ser Val Arg Leu Tyr Ser
                115                 120                 125

Gly Gly Thr Arg Leu Asn Thr Ala Ser Val Val Met His Gly Ser Trp
                130                 135                 140

Asn Pro Asn Leu Val Arg Asn Asp Ile Ala Met Ile Asn Leu Pro Ser
145                 150                 155                 160

Asn Val Ala Thr Ser Gly Asn Ile Ala Pro Ile Ala Leu Pro Ser Gly
                165                 170                 175

Asn Glu Leu Asn Asn Gln Phe Ala Gly Ala Thr Ala Thr Ala Ser Gly
                180                 185                 190

Phe Gly Leu Ala Arg Asp Gly Val Ile Asp Gly Asn Leu Arg His
                195                 200                 205

Val Asn Leu Pro Val Ile Thr Asn Ala Val Cys Ser Gln Ser Phe Pro
210                 215                 220

Gly Leu Ile Gln Ala Ser Asn Val Cys Thr Ser Gly Ala Asn Gly Arg
225                 230                 235                 240

Ser Thr Cys Gln Gly Asp Ser Gly Gly Pro Leu Val Val Asn Ser Asn
                245                 250                 255

Asn Arg Arg Ile Leu Ile Gly Val Thr Ser Phe Gly Ser Ala Arg Gly
                260                 265                 270

Cys Gln Val Gly Ser Pro Ala Ala Phe Ala Arg Val Ser Ser Tyr Ile
                275                 280                 285

Ser Trp Ile Asn Gln Arg Leu
                290                 295

<210> SEQ ID NO 52
<211> LENGTH: 234
<212> TYPE: PRT
<213> ORGANISM: Helicoverpa punctigera

<400> SEQUENCE: 52

Ile Val Gly Gly Ser Ser Ala Ser Leu Gly Gln Phe Pro Tyr Gln Ala
1               5                   10                  15

Gly Leu Leu Ile Asn Leu Pro Leu Gly Gln Ser Val Cys Gly Gly Ser
                20                  25                  30

Leu Leu Asn Gln Arg Arg Val Leu Thr Ala Ala His Cys Trp Phe Asp
                35                  40                  45

Gly Arg Asn Gln Ala Thr Ser Leu Thr Val Ile Leu Gly Ser Ile Asn
                50                  55                  60

Leu Phe Phe Gly Gly Thr Arg Leu Asn Ser Asn Ser Val Val Met Gln
65                  70                  75                  80

Gly Ser Trp Asn Pro Asn Leu Ile Arg Asn Asp Ile Ala Ile Ile Asn
                85                  90                  95

Leu Pro Ser Asn Val Gly Thr Ser Gly Asn Ile Ala Pro Ile Ala Leu
                100                 105                 110

Pro Ser Gly Asn Glu Leu Asn Asn Gln Phe Ala Gly Phe Thr Ala Thr
                115                 120                 125

Ala Ser Gly Phe Gly Leu Thr Arg Asp Gly Gly Asn Val Ser Pro Thr
                130                 135                 140

Leu Asn His Val Asn Leu Pro Val Ile Thr Asn Asn Val Cys Trp Gln
```

```
                145                 150                 155                 160
Ser Phe Pro Leu Tyr Ile Gln Ser Thr Asn Ile Cys Thr Ser Gly Ala
                165                 170                 175

Asn Gly Arg Gly Thr Cys Gln Gly Asp Ser Gly Pro Leu Val Val
            180                 185                 190

Thr Ser Asn Asn Arg Arg Ile Leu Ile Gly Val Thr Ser Phe Gly Ser
            195                 200                 205

Asp Arg Gly Cys Gln Val Gly Ala Pro Ala Ala Phe Ala Arg Val Thr
            210                 215                 220

Ser Tyr Ile Ser Trp Ile Asn Gln Arg Leu
225                 230

<210> SEQ ID NO 53
<211> LENGTH: 296
<212> TYPE: PRT
<213> ORGANISM: Helicoverpa punctigera

<400> SEQUENCE: 53

Met Ala Ala Ala Tyr Leu Leu Gly Leu Leu Phe Val Leu Gly Tyr Val
1               5                   10                  15

Gln Gly Gly Leu Leu Asn Ala Asp Pro Ala Ile Ile Glu Asp Leu Arg
                20                  25                  30

Asp Ala Glu Phe Ser Ser Gly Ser Arg Ile Val Ala Gly Trp Pro Ala
            35                  40                  45

Val Glu Gly Gln Ile Pro Tyr Gln Gly Ser Leu Arg Met Val Ser Ala
50                  55                  60

Ile Gly Gly Val Ser Ser Cys Gly Cys Ser Leu Ile His Asn Lys Trp
65                  70                  75                  80

Val Leu Thr Ala Ala His Cys Leu Ala Asn Arg Ile Thr Phe Val Val
                85                  90                  95

Arg Phe Gly Leu Thr Asn Leu Thr Arg Pro Glu Ile Leu Val Glu Ser
            100                 105                 110

Thr Asn Lys Tyr Ile His Pro Glu Tyr Asp Glu Ile Arg Ala Gly Val
            115                 120                 125

Gln Thr Ala Asp Leu Ala Leu Val Gly Leu Asp His Glu Ile Glu Tyr
        130                 135                 140

Ser Ala Asn Val Gln Pro Ser Arg Leu Met Ser Ser Ala Gln Lys Asn
145                 150                 155                 160

Ile Asn Tyr Glu Gly Ile Gln Met Ile Val Ser Gly Phe Gly Arg Thr
                165                 170                 175

Asp Asp Leu Trp Asn Gly Gly Ala Ser Glu Ile Leu Leu Trp Val
            180                 185                 190

Tyr Gln Arg Gly Val Ser Asn Glu Glu Cys Leu Arg Trp Tyr Pro Thr
            195                 200                 205

Ser Gln Val Ile Lys Glu Gln Thr Ile Cys Ala Gly Tyr Trp Asp Asn
            210                 215                 220

Pro Ser Gln Ser Ser Cys Gln Gly Asp Ser Gly Gly Pro Leu Thr Ile
225                 230                 235                 240

Ile Asp Ala Asp Gly Glu Arg Thr Gln Ser Arg Tyr Cys Glu Leu Arg
                245                 250                 255

Ile His Cys Trp Asn Ala Ala His Ser Pro Gln Gly Tyr Val Arg Pro
            260                 265                 270

Gly His Tyr His Asp Trp Phe Thr Glu Val Thr Gly Ile Asn Phe Asp
            275                 280                 285
```

Trp Asp Ser Asp Ala Ile Ile Pro
    290                 295

<210> SEQ ID NO 54
<211> LENGTH: 365
<212> TYPE: PRT
<213> ORGANISM: Helicoverpa punctigera

<400> SEQUENCE: 54

Met Ala Ala Ala Tyr Leu Leu Gly Leu Leu Phe Val Leu Gly Tyr Val
1               5                   10                  15

Gln Gly Gly Leu Leu Asn Ala Asp Pro Ala Ile Ile Glu Asp Leu Arg
            20                  25                  30

Asp Ala Glu Phe Ser Ser Phe Ser Arg Ile Val Ala Gly Trp Pro Ala
        35                  40                  45

Val Glu Gly Gln Ile Pro Tyr Gln Gly Ser Leu Arg Met Val Ser Ala
    50                  55                  60

Ile Gly Gly Val Ser Ser Cys Gly Cys Ser Leu Ile His Asn Lys Trp
65                  70                  75                  80

Val Leu Thr Ala Ala His Cys Leu Ala Asn Arg Ile Thr Phe Val Val
                85                  90                  95

Arg Phe Gly Leu Thr Asn Leu Thr Arg Pro Glu Ile Leu Val Glu Ser
            100                 105                 110

Thr Asn Lys Tyr Ile His Pro Glu Tyr Asp Glu Ile Arg Ala Gly Val
        115                 120                 125

Gln Thr Ala Asp Leu Ala Leu Val Gly Leu Asp Gln Glu Ile Glu Tyr
    130                 135                 140

Ser Ala Asn Val Gln Pro Ser Arg Leu Met Ser Ser Ala Gln Lys Asn
145                 150                 155                 160

Ile Asn Tyr Glu Gly Ile Gln Met Ile Val Ser Gly Phe Gly Arg Thr
                165                 170                 175

Asp Asp Leu Trp Asn Gly Gly Ala Ala Ser Glu Ile Leu Leu Trp Val
            180                 185                 190

Tyr Gln Arg Gly Val Ser Asn Glu Glu Cys Leu Arg Trp Tyr Pro Thr
        195                 200                 205

Ser Gln Val Ile Lys Glu Gln Thr Ile Cys Ala Gly Tyr Trp Asp Asn
    210                 215                 220

Pro Ser Gln Ser Ser Cys Gln Gly Asp Ser Gly Gly Pro Leu Thr Ile
225                 230                 235                 240

Ile Asp Ala Asp Gly Glu Arg Thr Gln Val Gly Ile Val Ser Ser Asp
                245                 250                 255

Pro Leu Leu Asp Ala Thr Val His Ser Pro Arg Val Thr Ser Pro Gly
            260                 265                 270

His Tyr His Asp Gly His Arg Gly Asp Arg His Gln Leu Arg Leu Gly
        275                 280                 285

Gln Arg Arg His Tyr Pro Asp Ser Ser Glu Ser Ser Leu Arg Ala Ala
    290                 295                 300

Ile Leu Pro Leu Glu Ser Ser Arg Ala Phe Ile Arg Arg Asn Gln Ser
305                 310                 315                 320

Ser Phe Arg Gly Gly Leu Cys Gln Pro Pro Arg Phe Pro Thr Arg Thr
                325                 330                 335

Val Pro Thr His Leu Pro Arg Arg Thr Leu Ala Ala Pro Pro Ser Glu
            340                 345                 350

Glu Glu Glu Ala Pro Glu Lys Val Arg Val Val Glu Tyr
        355                 360                 365

```
<210> SEQ ID NO 55
<211> LENGTH: 36
<212> TYPE: PRT
<213> ORGANISM: Helicoverpa punctigera

<400> SEQUENCE: 55

Ile Val Gly Gly Ser Leu Ser Ser Val Gly Gln Ile Pro Tyr Gln Ala
1               5                   10                  15

Gly Leu Val Ile Asp Leu Ala Gly Gly Gln Ala Val Cys Gly Gly Ser
            20                  25                  30

Leu Ile Ser Ala
        35

<210> SEQ ID NO 56
<211> LENGTH: 30
<212> TYPE: PRT
<213> ORGANISM: Helicoverpa punctigera

<400> SEQUENCE: 56

Ile Val Gly Gly Ser Thr Ser Ser Val Gly Gln Phe Pro Tyr Gln Ala
1               5                   10                  15

Gly Leu Leu Ala Ser Phe Ala Gly Gly Gln Ala Val Cys Gly
            20                  25                  30

<210> SEQ ID NO 57
<211> LENGTH: 37
<212> TYPE: PRT
<213> ORGANISM: Helicoverpa punctigera

<400> SEQUENCE: 57

Ile Val Gly Gly Ser Ile Thr Asp Ile Ala Asn Val Pro Tyr Gln Ala
1               5                   10                  15

Gly Leu Val Ile Thr Ile Phe Ile Phe Gln Ser Val Cys Gly Ala Ser
            20                  25                  30

Leu Ile Ser His Asn
        35

<210> SEQ ID NO 58
<211> LENGTH: 37
<212> TYPE: PRT
<213> ORGANISM: Helicoverpa punctigera

<400> SEQUENCE: 58

Ile Val Gly Gly Ser Ile Thr Asn Ile Ala Asn Val Pro Tyr Gln Ala
1               5                   10                  15

Gly Leu Val Ile Thr Ile Phe Ile Phe Gln Ser Val Cys Gly Ala Ser
            20                  25                  30

Leu Ile Ser His Asn
        35

<210> SEQ ID NO 59
<211> LENGTH: 37
<212> TYPE: PRT
<213> ORGANISM: Helicoverpa punctigera

<400> SEQUENCE: 59

Ile Val Gly Gly Ser Thr Ser Ser Leu Gly Ala Phe Pro Tyr Gln Ala
1               5                   10                  15

Gly Leu Leu Ala Ser Phe Ala Ser Gly Gln Gly Val Cys Gly Gly Ser
            20                  25                  30
```

Leu Leu Asn Val Arg
        35

<210> SEQ ID NO 60
<211> LENGTH: 37
<212> TYPE: PRT
<213> ORGANISM: Helicoverpa punctigera

<400> SEQUENCE: 60

Ile Val Gly Gly Ser Thr Ser Ser Leu Gly Ala Phe Pro Tyr Gln Ala
1               5                   10                  15

Gly Leu Leu Ala Asn Phe Ala Ser Gly Gln Gly Val Cys Gly Gly Ser
            20                  25                  30

Leu Leu Asn Gln Arg
        35

<210> SEQ ID NO 61
<211> LENGTH: 37
<212> TYPE: PRT
<213> ORGANISM: Helicoverpa punctigera

<400> SEQUENCE: 61

Ile Val Gly Gly Ser Ser Ala Ser Leu Gly Gln Phe Pro Tyr Gln Ala
1               5                   10                  15

Gly Leu Ser Leu Ile Tyr Ser Gly Gln Ser Val Cys Gly Gly Ser Leu
            20                  25                  30

Leu Asn Gln Arg Arg
        35

<210> SEQ ID NO 62
<211> LENGTH: 37
<212> TYPE: PRT
<213> ORGANISM: Helicoverpa punctigera

<400> SEQUENCE: 62

Ile Val Ala Gly Trp Pro Ala Val Glu Gly Gln Ile Pro Tyr Gln Gly
1               5                   10                  15

Ser Leu Arg Met Val Ser Ala Ile Gly Gly Val Ser Ser Cys Gly Cys
            20                  25                  30

Ser Leu Ile His Asn
        35

<210> SEQ ID NO 63
<211> LENGTH: 235
<212> TYPE: PRT
<213> ORGANISM: Helicoverpa punctigera

<400> SEQUENCE: 63

Ile Val Gly Gly Ser Ile Thr Asp Ile Ala Asn Val Pro Tyr Gln Ala
1               5                   10                  15

Gly Leu Val Ile Thr Ile Phe Ile Phe Gln Ser Val Cys Gly Ala Ser
            20                  25                  30

Leu Ile Ser His Asn Arg Leu Val Thr Ala Ala His Cys Lys Ser Asp
        35                  40                  45

Gly Val Leu Thr Ala Asn Ser Phe Thr Val Leu Gly Ser Asn Thr
    50                  55                  60

Leu Phe Phe Gly Gly Thr Arg Ile Asn Thr Asn Asp Val Val Met His
65                  70                  75                  80

Pro Asn Trp Asn Pro Ser Thr Ala Ala Asn Asp Ile Ala Val Met Arg

```
                85                  90                  95
Ile Ser Ser Val Ser Phe Ser Asn Val Ile Gln Pro Ile Ala Leu Pro
            100                 105                 110

Ser Gly Asp Glu Leu Asn Asn Leu Phe Val Gly Ala Asn Ala Leu Ala
            115                 120                 125

Phe Gly Phe Gly Arg Thr Ser Asp Gly Gly Ser Ile Gly Ser Asn Gln
            130                 135                 140

Gln Val Ser Ser Val Thr Ile Pro Val Ile Thr Asn Asp Glu Cys Ala
145                 150                 155                 160

Ala Val Tyr Gly Ser Ala Phe Val His Ser Ser Asn Ile Cys Thr Ser
            165                 170                 175

Gly Ala Gly Gly Lys Gly Thr Cys Asn Gly Asp Ser Gly Gly Pro Leu
            180                 185                 190

Ala Ile Asp Ser Asn Asn Glu Lys Ile Leu Ile Gly Val Thr Ser Tyr
            195                 200                 205

Gly Ala Gln Ala Gly Cys Ala Ala Gly Leu Pro Ala Ala Phe Ala Arg
            210                 215                 220

Val Thr Ser Phe Val Ser Trp Val Gln Ser Gln
225                 230                 235

<210> SEQ ID NO 64
<211> LENGTH: 235
<212> TYPE: PRT
<213> ORGANISM: Helicoverpa punctigera

<400> SEQUENCE: 64

Ile Val Gly Gly Ser Ile Thr Asn Ile Ala Asn Val Pro Tyr Gln Ala
1               5                   10                  15

Gly Leu Val Ile Thr Ile Phe Ile Phe Gln Ser Val Cys Gly Ala Ser
            20                  25                  30

Leu Ile Ser His Asn Arg Leu Val Thr Ala Ala His Cys Lys Phe Asp
            35                  40                  45

Gly Val Met Thr Ala Asn Ser Phe Thr Val Val Leu Gly Ser Asn Thr
            50                  55                  60

Leu Phe Phe Gly Gly Thr Arg Ile Asn Thr Asn Asp Val Val Met His
65              70                  75                  80

Pro Asn Trp Asn Pro Ser Thr Val Ala Asn Asp Ile Ala Val Ile Arg
            85                  90                  95

Ile Ser Ser Ile Val Tyr Asn Asn Val Ile Gln Pro Ile Ala Leu Pro
            100                 105                 110

Ser Gly Asp Glu Leu Asp Asn Leu Phe Val Gly Ala Asn Ala Leu Ala
            115                 120                 125

Ser Gly Phe Gly Arg Thr Ser Asp Ser Gly Gly Ile Gly Thr Asn Gln
            130                 135                 140

Gln Leu Ser Ser Val Thr Ile Pro Val Ile Thr Asn Ala Glu Cys Ala
145                 150                 155                 160

Ala Val Tyr Gly Pro Ala Phe Val His Asp Thr Asn Ile Cys Thr Ser
            165                 170                 175

Gly Ala Gly Gly Lys Gly Thr Cys Asn Gly Asp Ser Gly Gly Pro Leu
            180                 185                 190

Ala Val Asp Ser Asn Asp Lys Lys Ile Leu Ile Gly Val Thr Ser Tyr
            195                 200                 205

Gly Ala Ala Asp Gly Cys Ala Ala Gly Phe Pro Ala Ala Phe Ala Arg
            210                 215                 220
```

```
Val Thr Ser Phe Val Ser Trp Val Gln Ser Gln
225                 230                 235

<210> SEQ ID NO 65
<211> LENGTH: 234
<212> TYPE: PRT
<213> ORGANISM: Helicoverpa punctigera

<400> SEQUENCE: 65

Ile Val Gly Gly Ser Thr Ser Leu Gly Ala Phe Pro Tyr Gln Ala
1               5                   10                  15

Gly Leu Leu Ala Ser Phe Ala Ser Gly Gln Gly Val Cys Gly Gly Ser
                20                  25                  30

Leu Leu Asn Val Arg Arg Val Leu Thr Ala Ala His Cys Trp Phe Asp
            35                  40                  45

Gly Arg Asn Gln Ala Arg Ser Phe Thr Val Val Leu Gly Ser Val Arg
        50                  55                  60

Leu Tyr Ser Gly Gly Thr Arg Leu Asn Thr Ala Ser Val Val Met His
65                  70                  75                  80

Gly Ser Trp Asn Pro Asn Leu Val Arg Asn Asp Ile Ala Met Ile Asn
                85                  90                  95

Leu Pro Ser Asn Val Ala Thr Ser Gly Asn Ile Ala Pro Ile Ala Leu
                100                 105                 110

Pro Ser Gly Asn Glu Leu Asn Asn Gln Phe Ala Gly Ala Thr Ala Thr
            115                 120                 125

Ala Ser Gly Phe Gly Leu Ala Arg Asp Gly Val Ile Asp Gly Asn
        130                 135                 140

Leu Arg His Val Asn Leu Pro Val Ile Thr Asn Ala Val Cys Ser Gln
145                 150                 155                 160

Ser Phe Pro Gly Leu Ile Gln Ala Ser Asn Val Cys Thr Ser Gly Ala
                165                 170                 175

Asn Gly Arg Ser Thr Cys Gln Gly Asp Ser Gly Gly Pro Leu Val Val
                180                 185                 190

Asn Ser Asn Asn Arg Arg Ile Leu Ile Gly Val Thr Ser Phe Gly Ser
            195                 200                 205

Ala Arg Gly Cys Gln Val Gly Ser Pro Ala Ala Phe Ala Arg Val Ser
        210                 215                 220

Ser Tyr Ile Ser Trp Ile Asn Gln Arg Leu
225                 230

<210> SEQ ID NO 66
<211> LENGTH: 234
<212> TYPE: PRT
<213> ORGANISM: Helicoverpa punctigera

<400> SEQUENCE: 66

Ile Val Gly Gly Ser Thr Ser Leu Gly Ala Phe Pro Tyr Gln Ala
1               5                   10                  15

Gly Leu Leu Ala Asn Phe Ala Ser Gly Gln Gly Val Cys Gly Gly Ser
                20                  25                  30

Leu Leu Asn Gln Arg Arg Val Leu Thr Ala Ala His Cys Trp Phe Asp
            35                  40                  45

Gly Arg Asn Gln Ala Arg Ser Phe Thr Val Val Leu Gly Ser Val Arg
        50                  55                  60

Leu Phe Ser Gly Gly Thr Arg Leu Asp Thr Ala Ser Val Val Met His
65                  70                  75                  80
```

```
Gly Ser Trp Asn Pro Asn Leu Ile Arg Asn Asp Ile Ala Met Ile Asn
                85                  90                  95

Leu Pro Ser Asn Val Ala Thr Ser Gly Asn Ile Ala Pro Ile Ala Leu
            100                 105                 110

Pro Ser Gly Asn Glu Leu Asn Asn Asn Phe Asn Gly Ala Thr Ala Thr
        115                 120                 125

Ala Ser Gly Phe Gly Leu Ala Arg Asp Gly Gly Ser Val Asp Gly Asn
    130                 135                 140

Leu Arg His Val Asn Leu Pro Val Ile Thr Asn Ala Val Cys Thr Val
145                 150                 155                 160

Ser Phe Pro Gly Ile Ile Gln Ser Ser Asn Ile Cys Thr Ser Gly Ala
                165                 170                 175

Asn Gly Arg Ser Thr Cys Gln Gly Asp Ser Gly Gly Pro Leu Val Val
            180                 185                 190

Asn Ser Asn Asn Arg Arg Ile Leu Ile Gly Val Thr Ser Phe Gly Ser
        195                 200                 205

Ala Arg Gly Cys Gln Val Gly Ser Pro Ala Ala Phe Ala Arg Val Thr
    210                 215                 220

Ser Phe Ile Ser Trp Ile Asn Gln Arg Leu
225                 230

<210> SEQ ID NO 67
<211> LENGTH: 282
<212> TYPE: PRT
<213> ORGANISM: Helicoverpa punctigera

<400> SEQUENCE: 67

Ile Val Gly Gly Ser Ser Ala Ser Leu Gly Gln Phe Pro Tyr Gln Ala
1               5                   10                  15

Gly Leu Ser Leu Ile Tyr Ser Gly Gln Ser Val Cys Gly Gly Ser Leu
            20                  25                  30

Leu Asn Gln Arg Arg Val Leu Thr Ala Ala His Cys Trp Phe Asp Gly
        35                  40                  45

Ile Val Ala Gly Trp Pro Ala Val Glu Gly Gln Ile Pro Tyr Gln Gly
    50                  55                  60

Ser Leu Arg Met Val Ser Ala Ile Gly Gly Val Ser Ser Cys Gly Cys
65                  70                  75                  80

Ser Leu Ile His Asn Lys Trp Val Leu Thr Ala Ala His Cys Leu Ala
                85                  90                  95

Asn Arg Asn Gln Ala Thr Ser Leu Thr Val Ile Leu Gly Ser Ile Asn
            100                 105                 110

Leu Phe Phe Gly Gly Thr Arg Leu Asn Ser Asn Ser Val Val Met His
        115                 120                 125

Gly Ser Trp Asn Pro Asn Leu Ile Arg Asn Asp Ile Ala Ile Ile Asn
    130                 135                 140

Leu Pro Ser Asn Val Gly Thr Ser Gly Asn Ile Ala Pro Ile Ala Leu
145                 150                 155                 160

Pro Ser Gly Asn Glu Leu Asn Asn Gln Phe Ala Gly Phe Thr Ala Thr
                165                 170                 175

Ala Ser Gly Phe Gly Leu Thr Arg Asp Gly Gly Asn Val Ser Pro Thr
            180                 185                 190

Leu Asn His Val Asn Leu Pro Val Ile Thr Asn Asn Val Cys Trp Gln
        195                 200                 205

Ser Phe Pro Leu Tyr Ile Gln Ser Thr Asn Ile Cys Thr Ser Gly Ala
    210                 215                 220
```

-continued

Asn Gly Arg Gly Thr Cys Gln Gly Asp Ser Gly Gly Pro Leu Val Val
225                 230                 235                 240

Thr Ser Asn Asn Arg Arg Ile Leu Ile Gly Val Thr Ser Phe Gly Ser
            245                 250                 255

Asp Arg Gly Cys Gln Val Gly Ala Pro Ala Ala Phe Ala Arg Val Thr
        260                 265                 270

Ser Tyr Ile Ser Trp Ile Asn Gln Arg Leu
    275                 280

<210> SEQ ID NO 68
<211> LENGTH: 256
<212> TYPE: PRT
<213> ORGANISM: Helicoverpa punctigera

<400> SEQUENCE: 68

Ile Val Ala Gly Trp Pro Ala Val Glu Gly Gln Ile Pro Tyr Gln Gly
1               5                   10                  15

Ser Leu Arg Met Val Ser Ala Ile Gly Gly Val Ser Ser Cys Gly Cys
            20                  25                  30

Ser Leu Ile His Asn Lys Trp Val Leu Thr Ala Ala His Cys Leu Ala
        35                  40                  45

Asn Arg Ile Thr Phe Val Val Arg Phe Gly Leu Thr Asn Leu Thr Arg
    50                  55                  60

Pro Glu Ile Leu Val Glu Ser Thr Asn Lys Tyr Ile His Pro Glu Tyr
65                  70                  75                  80

Asp Glu Ile Arg Ala Gly Val Gln Thr Ala Asp Leu Ala Leu Val Gly
                85                  90                  95

Leu Asp His Glu Ile Glu Tyr Ser Ala Asn Val Gln Pro Ser Arg Leu
            100                 105                 110

Met Ser Ser Ala Gln Lys Asn Ile Asn Tyr Glu Gly Ile Gln Met Ile
        115                 120                 125

Val Ser Gly Phe Gly Arg Thr Asp Asp Leu Trp Asn Gly Gly Ala Ala
    130                 135                 140

Ser Glu Ile Leu Leu Trp Val Tyr Gln Arg Gly Val Ser Asn Glu Glu
145                 150                 155                 160

Cys Leu Arg Trp Tyr Pro Thr Ser Gln Val Ile Lys Glu Gln Thr Ile
                165                 170                 175

Cys Ala Gly Tyr Trp Asp Asn Pro Ser Gln Ser Ser Cys Gln Gly Asp
            180                 185                 190

Ser Gly Gly Pro Leu Thr Ile Ile Asp Ala Asp Gly Glu Arg Thr Gln
        195                 200                 205

Ser Arg Tyr Cys Glu Leu Arg Ile His Cys Trp Asn Ala Thr Ala His
    210                 215                 220

Ser Pro Gln Gly Tyr Val Arg Pro Gly His Tyr His Asp Trp Phe Thr
225                 230                 235                 240

Glu Val Thr Gly Ile Asn Phe Asp Trp Asp Ser Asp Ala Ile Ile Pro
                245                 250                 255

<210> SEQ ID NO 69
<211> LENGTH: 236
<212> TYPE: PRT
<213> ORGANISM: Helicoverpa punctigera

<400> SEQUENCE: 69

Ile Val Gly Gly Ser Leu Ser Ser Val Gly Gln Ile Pro Tyr Gln Ala
1               5                   10                  15

-continued

Gly Leu Val Ile Asp Leu Ala Gly Gly Gln Ala Val Cys Gly Gly Ser
          20                  25                  30

Leu Ile Ser Ala Ser Arg Val Leu Thr Ala Ala His Cys Trp Phe Asp
          35                  40                  45

Gly Gln Asn Gln Ala Trp Arg Phe Thr Val Val Leu Gly Ser Thr Thr
  50                  55                  60

Leu Phe Ser Gly Gly Thr Arg Ile Pro Thr Ser Asn Val Val Met His
65                  70                  75                  80

Gly Ser Trp Thr Pro Ser Leu Ile Arg Asn Asp Val Ala Val Ile Arg
              85                  90                  95

Leu Gly Thr Asn Val Ala Thr Ser Asn Thr Ile Ala Ile Ala Leu
              100                 105                 110

Pro Ser Gly Ser Gln Ile Asn Glu Asn Phe Ala Gly Glu Thr Ala Leu
              115                 120                 125

Ala Ser Gly Phe Gly Leu Thr Ser Asp Thr Gly Ser Ile Ser Ser Asn
  130                 135                 140

Gln Ala Leu Ser His Val Asn Leu Pro Val Ile Thr Asn Ala Val Cys
145                 150                 155                 160

Arg Asn Ser Phe Pro Leu Leu Ile Gln Asp Ser Asn Ile Cys Thr Ser
              165                 170                 175

Gly Ala Asn Gly Arg Ser Thr Cys Arg Gly Asp Ser Gly Gly Pro Leu
              180                 185                 190

Val Val Thr Arg Asn Asn Arg Pro Leu Leu Ile Gly Ile Thr Ser Phe
              195                 200                 205

Gly Ser Ala Arg Gly Cys Gln Val Gly Ser Pro Ala Ala Phe Ala Arg
  210                 215                 220

Val Thr Ser Tyr Ile Ser Trp Ile Asn Gly Gln Leu
225                 230                 235

<210> SEQ ID NO 70
<211> LENGTH: 224
<212> TYPE: PRT
<213> ORGANISM: Homo sapiens

<400> SEQUENCE: 70

Ile Val Gly Gly Tyr Thr Cys Glu Glu Asn Ser Leu Pro Tyr Gln Val
1               5                   10                  15

Ser Leu Asn Ser Gly Ser His Phe Cys Gly Gly Ser Leu Ile Ser Glu
              20                  25                  30

Gln Trp Val Val Ser Ala Ala His Cys Tyr Lys Thr Arg Ile Gln Val
          35                  40                  45

Arg Leu Gly Glu His Asn Ile Lys Val Leu Glu Gly Asn Glu Gln Phe
  50                  55                  60

Ile Asn Ala Ala Lys Ile Ile Arg His Pro Lys Tyr Asn Arg Asp Thr
65                  70                  75                  80

Leu Asp Asn Asp Ile Met Leu Ile Lys Leu Ser Ser Pro Ala Val Ile
              85                  90                  95

Asn Ala Arg Val Ser Thr Ile Ser Leu Pro Thr Ala Pro Pro Ala Ala
              100                 105                 110

Gly Thr Glu Cys Leu Ile Ser Gly Trp Gly Asn Thr Leu Ser Phe Gly
              115                 120                 125

Ala Asp Tyr Pro Asp Glu Leu Lys Cys Leu Asp Ala Pro Val Leu Thr
  130                 135                 140

Gln Ala Glu Cys Lys Ala Ser Tyr Pro Gly Lys Ile Thr Asn Ser Met

```
145                 150                 155                 160
Phe Cys Val Gly Phe Leu Glu Gly Gly Lys Asp Ser Cys Gln Arg Asp

```
<212> TYPE: PRT
<213> ORGANISM: Helicoverpa punctigera

<400> SEQUENCE: 72

Val His Leu Glu Asp Ser Ile Asp Leu Glu Asp Ile Thr Ala Trp Gly
1               5                   10                  15

Tyr Leu Thr Lys Phe Gly Ile Pro Glu Ala Glu Lys Ile Arg Asn Ala
            20                  25                  30

Glu Glu Ala Ser Ser Ala Ser Arg Ile Val Gly Gly Ser Leu Ser Ser
        35                  40                  45

Leu Gly Gln Ile Pro Tyr Gln Ala Gly Leu Val Ile Asp Leu Ala Gly
    50                  55                  60

Gly Gln Ala Val Cys Gly Gly Ser Leu Ile Ser Ala Ser Arg Val Leu
65                  70                  75                  80

Thr Ala Ala His Cys Trp Phe Asp Gly Gln Asn Gln Ala Trp Arg Phe
                85                  90                  95

Thr Val Val Leu Gly Ser Thr Thr Leu Phe Ser Gly Thr Arg Ile
            100                 105                 110

Pro Thr Ser Asn Val Val Met His Gly Ser Trp Thr Pro Ser Leu Ile
            115                 120                 125

Arg Asn Asp Val Ala Val Ile Arg Leu Gly Thr Asn Val Gly Thr Ser
130                 135                 140

Asn Thr Ile Ala Ile Ile Ala Leu Pro Ser Gly Ser Gln Ile Asn Glu
145                 150                 155                 160

Asn Phe Ala Gly Glu Thr Ala Leu Ala Ser Gly Phe Gly Leu Thr Ser
                165                 170                 175

Asp Thr Gly Ser Ile Ser Ser Asn Gln Ala Leu Ser His Val Asn Leu
            180                 185                 190

Pro Val Ile Thr Asn Ala Val Cys Arg Asn Ser Phe Pro Leu Leu Ile
        195                 200                 205

Gln Asp Ser Asn Ile Cys Thr Ser Gly Ala Asn Gly Arg Ser Thr Cys
    210                 215                 220

Arg Gly Asp Ser Gly Gly Pro Leu Val Val Thr Arg Asn Asn Arg Pro
225                 230                 235                 240

Leu Leu Ile Gly Ile Thr Ser Phe Gly Ser Ala Arg Gly Cys Gln Val
                245                 250                 255

Gly Ser Pro Ala Ala Phe Ala Arg Val Thr Ser Tyr Ile Ser Trp Ile
            260                 265                 270

Asn Gly Gln
        275

<210> SEQ ID NO 73
<211> LENGTH: 230
<212> TYPE: PRT
<213> ORGANISM: bovine

<400> SEQUENCE: 73

Ile Val Asn Gly Glu Asp Ala Val Pro Gly Ser Trp Pro Trp Gln Val
1               5                   10                  15

Ser Leu Gln Asp Ser Thr Gly Phe His Phe Cys Gly Gly Ser Leu Ile
            20                  25                  30

Ser Glu Asp Trp Val Val Thr Ala Ala His Cys Gly Val Thr Thr Ser
        35                  40                  45

Asp Val Val Val Ala Gly Glu Phe Asp Gln Gly Ser Ser Ser Glu Lys
    50                  55                  60
```

```
Ile Gln Lys Leu Lys Ile Ala Lys Val Phe Lys Asn Ser Lys Tyr Asn
65                  70                  75                  80

Ser Leu Thr Ile Asn Asn Asp Ile Thr Leu Lys Leu Ala Thr Pro
                85                  90                  95

Ala Gln Phe Ser Glu Thr Val Ser Ala Val Cys Leu Pro Ser Ala Asp
                100                 105                 110

Glu Asp Phe Pro Ala Gly Met Leu Cys Ala Thr Thr Gly Trp Gly Lys
            115                 120                 125

Thr Lys Tyr Asn Ala Leu Lys Thr Pro Asp Lys Leu Gln Gln Ala Thr
            130                 135                 140

Leu Pro Ile Val Ser Asn Thr Asp Cys Arg Lys Tyr Trp Gly Ser Arg
145                 150                 155                 160

Val Thr Asp Val Met Ile Cys Ala Gly Ala Ser Gly Val Ser Ser Cys
                165                 170                 175

Met Gly Asp Ser Gly Gly Pro Leu Val Cys Gln Lys Asn Gly Ala Trp
            180                 185                 190

Thr Leu Ala Gly Ile Val Ser Trp Gly Ser Ser Thr Cys Ser Thr Ser
            195                 200                 205

Thr Pro Ala Val Tyr Ala Arg Val Thr Ala Leu Met Pro Trp Val Gln
    210                 215                 220

Glu Thr Leu Ala Ala Asn
225                 230

<210> SEQ ID NO 74
<211> LENGTH: 230
<212> TYPE: PRT
<213> ORGANISM: bovine

<400> SEQUENCE: 74

Ile Val Asn Gly Glu Glu Ala Val Pro Gly Ser Trp Pro Trp Gln Val
1               5                   10                  15

Ser Leu Gln Asp Lys Thr Gly Phe His Phe Cys Gly Gly Ser Leu Ile
                20                  25                  30

Asn Glu Asn Trp Val Val Thr Ala Ala His Cys Gly Val Thr Thr Ser
            35                  40                  45

Asp Val Val Ala Gly Glu Phe Asp Gln Gly Leu Glu Thr Glu Asp
        50                  55                  60

Thr Gln Val Leu Lys Ile Gly Lys Val Phe Lys Asn Pro Lys Phe Ser
65                  70                  75                  80

Ile Leu Thr Val Arg Asn Asp Ile Thr Leu Leu Lys Leu Ser Thr Ala
                85                  90                  95

Ala Ser Phe Ser Gln Thr Val Ser Ala Val Cys Leu Pro Ser Ala Ser
                100                 105                 110

Asp Asp Phe Ala Ala Gly Thr Thr Cys Val Thr Thr Gly Trp Gly Leu
            115                 120                 125

Thr Arg Tyr Thr Asn Ala Asn Thr Pro Asp Arg Leu Gln Gln Ala Ser
            130                 135                 140

Leu Pro Leu Leu Ser Asn Thr Asn Cys Lys Lys Tyr Trp Gly Thr Lys
145                 150                 155                 160

Ile Lys Asp Ala Met Ile Cys Ala Gly Ala Ser Gly Val Ser Ser Cys
                165                 170                 175

Met Gly Asp Ser Gly Gly Pro Leu Val Cys Lys Gln Asn Gly Ala Trp
            180                 185                 190

Thr Leu Val Gly Ile Val Ser Trp Gly Ser Ser Thr Cys Ser Thr Ser
            195                 200                 205
```

```
Thr Pro Gly Val Tyr Ala Arg Val Thr Ala Leu Val Asn Trp Val Gln
    210                 215                 220

Gln Thr Leu Ala Ala Asn
225                 230

<210> SEQ ID NO 75
<211> LENGTH: 237
<212> TYPE: PRT
<213> ORGANISM: Helicoverpa punctigera

<400> SEQUENCE: 75

Ile Val Gly Gly Ser Thr Ser Ser Leu Gly Ala Phe Pro Tyr Gln Ala
1               5                   10                  15

Gly Leu Leu Ala Ser Phe Ala Ser Gly Gln Gly Val Cys Gly Gly Ser
            20                  25                  30

Leu Leu Asn Val Arg Arg Val Leu Thr Ala Ala His Cys Trp Phe Asp
        35                  40                  45

Gly Arg Asn Gln Ala Arg Ser Phe Thr Val Val Leu Gly Ser Val Arg
    50                  55                  60

Leu Tyr Ser Gly Gly Thr Arg Leu Asn Thr Ala Ser Val Val Met His
65                  70                  75                  80

Gly Ser Trp Asn Pro Asn Leu Val Arg Thr Ile Asn Asn Asp Ile Ala
                85                  90                  95

Met Ile Asn Leu Pro Ser Asn Val Ala Thr Ser Gly Asn Ile Ala Pro
            100                 105                 110

Ile Ala Leu Pro Ser Gly Asn Glu Leu Asn Asn Gln Phe Ala Gly Ala
        115                 120                 125

Thr Ala Thr Ala Ser Gly Phe Gly Leu Ala Arg Asp Gly Gly Val Ile
    130                 135                 140

Asp Gly Asn Leu Arg His Val Asn Leu Pro Val Ile Thr Asn Ala Val
145                 150                 155                 160

Cys Ser Gln Ser Phe Pro Gly Leu Ile Gln Ala Ser Asn Val Cys Thr
                165                 170                 175

Ser Gly Ala Asn Gly Arg Ser Thr Cys Gln Gly Gly Asp Ser Gly Gly
            180                 185                 190

Pro Leu Val Asn Ser Asn Asn Arg Arg Ile Leu Ile Gly Val Thr Ser
        195                 200                 205

Phe Gly Ser Ala Arg Gly Cys Gln Val Gly Ser Pro Ala Ala Phe Ala
    210                 215                 220

Arg Val Ser Ser Tyr Ile Ser Trp Ile Asn Gln Arg Leu
225                 230                 235

<210> SEQ ID NO 76
<211> LENGTH: 236
<212> TYPE: PRT
<213> ORGANISM: Helicoverpa punctigera

<400> SEQUENCE: 76

Ile Val Gly Gly Ser Leu Ser Ser Val Gly Gln Ile Pro Tyr Gln Ala
1               5                   10                  15

Gly Leu Val Ile Asp Leu Ala Gly Gln Ala Val Cys Gly Gly Ser
            20                  25                  30

Leu Leu Ser Ala Ser Arg Val Leu Thr Ala Ala His Cys Trp Phe Asp
        35                  40                  45

Gly Gln Asn Gln Ala Trp Arg Phe Thr Val Val Leu Gly Ser Thr Thr
    50                  55                  60
```

Leu Phe Ser Gly Gly Thr Arg Leu Asn Ile Pro Ser Ser Asn Met His
65                  70                  75                  80

Gly Ser Trp Asn Pro Ser Leu Ile Arg Asn Asp Val Ala Val Ile Arg
                85                  90                  95

Leu Gly Thr Asn Val Ala Thr Ser Asn Thr Ile Ala Ile Ile Ala Leu
            100                 105                 110

Pro Ser Gly Ser Gln Ile Asn Glu Asn Phe Ala Gly Glu Thr Ala Leu
        115                 120                 125

Ala Ser Gly Phe Gly Leu Thr Ser Tyr Thr Gly Ser Ile Ser Ser Asn
    130                 135                 140

Gln Ala Leu Ser His Val Asn Leu Pro Val Ile Thr Asn Ala Val Cys
145                 150                 155                 160

Arg Asn Ser Phe Ser Leu Leu Ile Gln Asp Ser Asn Ile Cys Thr Ser
                165                 170                 175

Gly Ala Asn Gly Arg Ser Thr Cys Arg Gly Asp Ser Gly Gly Pro Leu
            180                 185                 190

Val Val Thr Arg Asn Asn Arg Pro Leu Leu Ile Gly Val Thr Ser Phe
        195                 200                 205

Gly Ser Ala Arg Gly Cys Gln Val Gly Ser Pro Ala Ala Phe Ala Arg
    210                 215                 220

Val Thr Ser Tyr Ile Ser Trp Ile Asn Gly Gln Leu
225                 230                 235

<210> SEQ ID NO 77
<211> LENGTH: 107
<212> TYPE: PRT
<213> ORGANISM: potato

<400> SEQUENCE: 77

Met Glu Ser Lys Phe Ala His Ile Ile Val Phe Phe Leu Leu Ala Thr
1               5                   10                  15

Ser Phe Glu Thr Leu Met Ala Arg Lys Glu Ser Asp Gly Pro Glu Val
            20                  25                  30

Ile Glu Leu Leu Lys Glu Phe Glu Cys Asn Gly Lys Gln Phe Trp Pro
        35                  40                  45

Glu Leu Ile Gly Val Pro Thr Lys Leu Ala Lys Glu Ile Ile Glu Lys
    50                  55                  60

Glu Asn Ser Leu Ile Asn Asn Val Gln Ile Leu Leu Asn Gly Ser Pro
65                  70                  75                  80

Val Thr Met Asp Tyr Arg Cys Asn Arg Val Arg Leu Phe Asp Asn Ile
                85                  90                  95

Leu Gly Ser Val Val Gln Ile Pro Arg Val Ala
            100                 105

<210> SEQ ID NO 78
<211> LENGTH: 107
<212> TYPE: PRT
<213> ORGANISM: potato

<400> SEQUENCE: 78

Met Glu Ser Lys Phe Ala His Ile Ile Val Phe Phe Leu Leu Ala Thr
1               5                   10                  15

Ser Phe Glu Thr Leu Leu Ala Arg Lys Glu Ser Asp Gly Pro Glu Val
            20                  25                  30

Ile Glu Leu Leu Lys Glu Phe Glu Cys Asn Gly Lys Gln Phe Trp Pro
        35                  40                  45

```
Glu Leu Ile Gly Val Pro Thr Lys Leu Ala Lys Glu Ile Ile Glu Lys
        50                  55                  60

Glu Asn Ser Leu Ile Asn Asn Val Gln Ile Leu Leu Asn Gly Ser Pro
 65                  70                  75                  80

Val Ala Met Asp Tyr Arg Cys Asn Arg Val Arg Leu Phe Asp Asn Ile
                 85                  90                  95

Leu Gly Ser Val Val Gln Ile Pro Arg Val Ala
            100                 105
```

<210> SEQ ID NO 79
<211> LENGTH: 71
<212> TYPE: PRT
<213> ORGANISM: potato

<400> SEQUENCE: 79

```
Lys Glu Phe Glu Cys Asp Gly Lys Leu Gln Trp Pro Glu Leu Ile Gly
 1               5                  10                  15

Val Pro Thr Lys Leu Ala Lys Glu Ile Ile Glu Lys Gln Asn Ser Leu
                20                  25                  30

Ile Ser Asn Val His Ile Leu Leu Asn Gly Ser Pro Val Thr Met Asp
                35                  40                  45

Phe Arg Cys Asn Arg Val Arg Leu Phe Asp Asp Ile Leu Gly Ser Val
            50                  55                  60

Val Gln Ile Pro Arg Val Ala
 65                  70
```

<210> SEQ ID NO 80
<211> LENGTH: 106
<212> TYPE: PRT
<213> ORGANISM: potato

<400> SEQUENCE: 80

```
Met Glu Ser Lys Phe Ala His Ile Ile Val Phe Phe Leu Leu Ala Thr
 1               5                  10                  15

Ser Phe Glu Thr Leu Leu Ala Arg Lys Glu Ser Asp Gly Pro Glu Val
                20                  25                  30

Ile Glu Leu Gln Lys Glu Phe Glu Cys Asn Gly Lys Gln Arg Trp Pro
                35                  40                  45

Glu Leu Ile Gly Val Pro Thr Lys Leu Ala Lys Gly Ile Ile Glu Lys
        50                  55                  60

Glu Asn Ser Leu Ile Thr Asn Val Gln Ile Leu Leu Asn Gly Ser Pro
 65                  70                  75                  80

Val Thr Met Asp Tyr Arg Ser Asn Arg Val Arg Leu Phe Asp Asn Ile
                 85                  90                  95

Leu Gly Asp Val Val Gln Ile Pro Arg Val
            100                 105
```

<210> SEQ ID NO 81
<211> LENGTH: 111
<212> TYPE: PRT
<213> ORGANISM: potato

<400> SEQUENCE: 81

```
Met Glu Ser Lys Phe Ala His Ile Ile Val Phe Phe Leu Leu Ala Thr
 1               5                  10                  15

Ser Phe Glu Thr Leu Met Ala Arg Lys Glu Gly Asp Gly Ser Glu Val
                20                  25                  30
```

```
Ile Lys Leu Leu Lys Glu Ser Glu Ser Trp Cys Lys Gly Lys
        35              40                  45

Gln Phe Trp Pro Glu Leu Ile Gly Val Pro Thr Lys Leu Ala Lys Glu
    50                  55                  60

Ile Ile Glu Lys Glu Asn Pro Ser Ile Asn Asp Val Pro Ile Ile Leu
65                  70                  75                  80

Asn Gly Thr Pro Val Pro Ala Asp Phe Arg Cys Asn Arg Val Arg Leu
                85                  90                  95

Phe Asp Asn Ile Leu Gly Asp Val Val Gln Ile Pro Arg Val Ala
            100                 105                 110

<210> SEQ ID NO 82
<211> LENGTH: 111
<212> TYPE: PRT
<213> ORGANISM: potato

<400> SEQUENCE: 82

Met Glu Ser Lys Phe Ala His Ile Ile Val Phe Phe Leu Leu Ala Thr
1               5                   10                  15

Ser Phe Glu Thr Leu Met Ala Arg Lys Glu Ile Asp Gly Pro Glu Val
            20                  25                  30

Ile Glu Leu Leu Lys Glu Phe Asp Ser Asn Leu Met Cys Glu Gly Lys
        35                  40                  45

Gln Met Trp Pro Glu Leu Ile Gly Val Pro Thr Lys Leu Ala Lys Glu
    50                  55                  60

Ile Ile Glu Lys Glu Asn Pro Ser Ile Thr Asn Ile Pro Ile Leu Leu
65                  70                  75                  80

Ser Gly Ser Pro Ile Thr Leu Asp Tyr Leu Cys Asp Arg Val Arg Leu
                85                  90                  95

Phe Asp Asn Ile Leu Gly Phe Val Val Gln Met Pro Val Val Thr
            100                 105                 110

<210> SEQ ID NO 83
<211> LENGTH: 107
<212> TYPE: PRT
<213> ORGANISM: potato

<400> SEQUENCE: 83

Met Val Lys Phe Ala His Val Val Ala Phe Leu Leu Leu Ala Ser Leu
1               5                   10                  15

Ile Gln Pro Leu Thr Ala Arg Asp Leu Glu Ile Asn Val Leu Gln Leu
            20                  25                  30

Asp Val Ser Gln Ser Gly Cys Pro Gly Val Thr Lys Glu Arg Trp Pro
        35                  40                  45

Glu Leu Leu Gly Thr Pro Ala Lys Phe Ala Met Gln Ile Ile Gln Lys
    50                  55                  60

Glu Asn Pro Lys Leu Thr Asn Val Gln Thr Ile Leu Asn Gly Gly Pro
65                  70                  75                  80

Val Thr Glu Asp Leu Arg Cys Asn Arg Val Arg Leu Phe Val Asn Val
                85                  90                  95

Leu Asp Phe Ile Val Gln Thr Pro Gln Ile Gly
            100                 105

<210> SEQ ID NO 84
<211> LENGTH: 73
<212> TYPE: PRT
<213> ORGANISM: potato
```

<400> SEQUENCE: 84

Met Ser Ser Thr Glu Cys Gly Gly Gly Gly Ala Lys Thr Ser
1               5                   10                  15

Trp Pro Glu Val Val Gly Leu Ser Val Glu Asp Ala Lys Lys Val Ile
            20                  25                  30

Leu Lys Asp Lys Pro Asp Ala Asp Ile Val Val Leu Pro Val Gly Ser
        35                  40                  45

Val Val Thr Ala Asp Tyr Arg Pro Asn Arg Val Arg Ile Phe Val Asp
    50                  55                  60

Ile Val Ala Gln Thr Pro His Ile Gly
65                  70

<210> SEQ ID NO 85
<211> LENGTH: 70
<212> TYPE: PRT
<213> ORGANISM: potato

<400> SEQUENCE: 85

Thr Glu Phe Gly Ser Glu Leu Lys Ser Phe Pro Glu Val Val Gly Lys
1               5                   10                  15

Thr Val Asp Gln Ala Arg Glu Tyr Phe Thr Leu His Tyr Pro Gln Tyr
            20                  25                  30

Asp Val Tyr Phe Leu Pro Glu Gly Ser Pro Val Thr Leu Asp Leu Arg
        35                  40                  45

Tyr Asn Arg Val Arg Val Phe Tyr Asn Pro Gly Thr Asn Val Val Asn
    50                  55                  60

His Val Pro His Val Gly
65                  70

<210> SEQ ID NO 86
<211> LENGTH: 60
<212> TYPE: DNA
<213> ORGANISM: potato

<400> SEQUENCE: 86
ggatccatga aactcttggc tgtgactcta ttggctttcg ccgcggtcgt ctccgcgagg      60

<210> SEQ ID NO 87
<211> LENGTH: 18
<212> TYPE: PRT
<213> ORGANISM: potato

<400> SEQUENCE: 87

Met Lys Leu Leu Ala Val Thr Leu Leu Ala Phe Ala Ala Val Val Ser
1               5                   10                  15

Ala Arg

<210> SEQ ID NO 88
<211> LENGTH: 40
<212> TYPE: DNA
<213> ORGANISM: artificial sequence
<220> FEATURE:
<223> OTHER INFORMATION: FwBacRECH2 primer

<400> SEQUENCE: 88
ggatccatga aactcttggc tgtgactcta ttggctttcg      40

<210> SEQ ID NO 89
<211> LENGTH: 40
<212> TYPE: DNA

<213> ORGANISM: artificial sequence
<220> FEATURE:
<223> OTHER INFORMATION: FwBacRECH2 primer

<400> SEQUENCE: 89
ttggctttcg ccgcggtcgt ctccgcgagg aacgggtccc                          40

<210> SEQ ID NO 90
<211> LENGTH: 864
<212> TYPE: DNA
<213> ORGANISM: Helicoverpa sp

<400> SEQUENCE: 90
aacggatccc accatcacca tcaccatgtt cacctcgagg attctattga tctggaagat     60
attaccgctt ggggatacct caccaaattc ggtattccag aagctgagaa atccgcaac    120
gctgaagaag ctagctctgc tagcaggatc gtcggtggtt cattgtccag tgtcggacag   180
atcccttacc aggctggtct cgtcattgac ttagcaggtg gccaggctgt ctgcggaggc   240
tccctgatca gcgcttcccg cgtactgacc gctgctcact gctggttcga cggccaaaac   300
caggcctgga gattcaccgt tgttcttggt tccaccacct tgttctctgg cggtaccaga   360
atccctacat ccaatgttgt tatgcacgga agctggactc ctagccttat ccgtaacgat   420
gttgccgtaa tcagattggg caccaacgta gcaacctcaa acaccattgc catcatcgct   480
ctacccagcg gcagccagat caacgagaac ttcgccggtg aaaccgccct cgcctccggc   540
ttcggtctca ccagtgacac cggcagcatc tccagcaacc aggctctgag ccacgtcaac   600
ctgccagtga tcaccaacgc tgtgtgcaga aattcattcc ccctgctgat ccaggactct   660
aacatttgca ccagcggtgc caacggcagg agcacttgcc gcggtgactc cggcggtcct   720
ctcgtcgtca ccaggaacaa cagaccactc ttgatcggta tcacctcttt cggatctgcc   780
cgcggttgcc aagttggatc tcccgctgcc ttcgccagag tcacctctta catcagctgg   840
atcaacggcc agctctaaaa gctt                                         864

<210> SEQ ID NO 91
<211> LENGTH: 287
<212> TYPE: PRT
<213> ORGANISM: Helicoverpa sp

<400> SEQUENCE: 91

Asn Gly Ser His His His His His Val His Leu Glu Asp Ser Ile
1               5                   10                  15

Asp Leu Glu Asp Ile Thr Ala Trp Gly Tyr Leu Thr Lys Phe Gly Ile
            20                  25                  30

Pro Glu Ala Glu Lys Ile Arg Asn Ala Glu Glu Ala Ser Ser Ala Ser
        35                  40                  45

Arg Ile Val Gly Gly Ser Leu Ser Ser Val Gly Gln Ile Pro Tyr Gln
    50                  55                  60

Ala Gly Leu Val Ile Asp Leu Ala Gly Gly Gln Ala Val Cys Gly Gly
65                  70                  75                  80

Ser Leu Ile Ser Ala Ser Arg Val Leu Thr Ala Ala His Cys Trp Phe
                85                  90                  95

Asp Gly Gln Asn Gln Ala Trp Arg Phe Thr Val Val Leu Gly Ser Thr
            100                 105                 110

Thr Leu Phe Ser Gly Gly Thr Arg Ile Pro Thr Ser Asn Val Val Met
        115                 120                 125

His Gly Ser Trp Thr Pro Ser Leu Ile Arg Asn Asp Val Ala Val Ile

-continued

```
    130                 135                 140

Arg Leu Gly Thr Asn Val Ala Thr Ser Asn Thr Ile Ala Ile Ile Ala
145                 150                 155                 160

Leu Pro Ser Gly Ser Gln Ile Asn Glu Asn Phe Ala Gly Glu Thr Ala
                165                 170                 175

Leu Ala Ser Gly Phe Gly Leu Thr Ser Asp Thr Gly Ser Ile Ser Ser
            180                 185                 190

Asn Gln Ala Leu Ser His Val Asn Leu Pro Val Ile Thr Asn Ala Val
        195                 200                 205

Cys Arg Asn Ser Phe Pro Leu Leu Ile Gln Asp Ser Asn Ile Cys Thr
    210                 215                 220

Ser Gly Ala Asn Gly Arg Ser Thr Cys Arg Gly Asp Ser Gly Gly Pro
225                 230                 235                 240

Leu Val Val Thr Arg Asn Asn Arg Pro Leu Leu Ile Gly Ile Thr Ser
                245                 250                 255

Phe Gly Ser Ala Arg Gly Cys Gln Val Gly Ser Pro Ala Ala Phe Ala
            260                 265                 270

Arg Val Thr Ser Tyr Ile Ser Trp Ile Asn Gly Gln Leu Lys Leu
        275                 280                 285

<210> SEQ ID NO 92
<211> LENGTH: 25
<212> TYPE: DNA
<213> ORGANISM: artificial sequence
<220> FEATURE:
<223> OTHER INFORMATION: RvRECH primer

<400> SEQUENCE: 92
gatcaacggc cagctctaaa agctt                                           25

<210> SEQ ID NO 93
<211> LENGTH: 15
<212> TYPE: PRT
<213> ORGANISM: Helicoverpa sp

<400> SEQUENCE: 93

Ile Val Gly Gly Ser Thr Ser Ser Leu Gly Ala Thr Pro Tyr Gln
1               5                   10                  15
```

INSECT CHYMOTRYPSIN AND INHIBITORS THEREOF

The present application is a U.S. national phase filing under 35 U.S.C. 371 of PCT Application No. PCT/AU2004/000524, filed Apr. 23, 2004, which claim the benefit of U.S. provisional patent Application No. 60/465,054, filed Apr. 23, 2003, each of which are hereby incorporated by reference in their entirety.

BACKGROUND OF THE INVENTION

1. Field of the Invention

The present invention relates generally to a novel chymotrypsin that exhibits resistance to a plant serine proteinase inhibitor. More particularly, the present invention provides a chymotrypsin which is up-regulated in the gut of *Helicoverpa armigera* and *Helicoverpa punctigera* insect larvae when fed the serine proteinase inhibitors of *Nicotiana alata*. The novel chymotrypsin represents, therefore, a target for the identification of antagonists including inhibitors which are proposed to be useful in the control of *Helicoverpa* spp. populations that have become resistant to serine proteinase inhibitors produced in plants. The antagonists of the chymotrypsin may be topically applied to the plants or, when in proteinaceous form, may be produced by genetic means in plant cells. The antagonists may act at the level of gene expression or protein activity.

2. Description of the Prior Art

Bibliographic details of the publications referred to in this specification are also collected at the end of the description.

Reference to any prior art in this specification is not, and should not be taken as, an acknowledgment or any form of suggestion that this prior art forms part of the common general knowledge in any country.

Female reproductive tissues and wounded leaves of the ornamental tobacco, *Nicotiana alata* amass high levels of serine proteinase inhibitors (PIs) for protection against pests and pathogens (Atkinson et al., *The Plant Cell* 5: 203-213, 1993). These 6 kDa PIs accumulate in the vacuole (Miller et al., *Plant Cell* 11: 1499-1508, 1999) and are derived in vivo from the post-translational modification of a 40.3 kDa precursor protein. The precursor of the PI protein (referred to as "NaPI") is composed of six repeated regions of high sequence identity (FIG. 1) each with a potential PI reactive site. Processing of the six-repeat precursor protein unexpectedly occurs at sites located within, rather than between the repeated regions. Complete removal of the linker sequence (Glu-Glu-Lys-Lys-Asn) [SEQ ID NO:1] contained within each repeated region, generates five contiguous 6 kDa inhibitors (C1 and T1-T4) and a novel two-chain chymotrypsin inhibitor (C2) formed by disulphide bond linkage of N-terminal and C-terminal peptide fragments (Heath et al., *European Journal of Biochemistry* 230(1): 25-257, 1995; Lee et al., *Nature Structural Biology* 6(6): 526-530, 1999). The structures of C1, T1-T4 and C2 have been solved using ¹H-NMR techniques (Nielson et al., *J. Mol. Biol.* 242: 231-243, 1994; Nielson et al., *Biochemistry* 34: 14304-14311, 1995; Lee et al., 1999, supra).

*Nicotiana alata* also has a second gene related to NaPI that encodes a closely related precursor protein with four rather than six repeated domains (Miller et al., *Plant Mol. Biol.* 42: 329-333, 2000). This precursor is also processed in vivo resulting in the release of three contiguous 6 kDa inhibitors (C1, T4 and T5) and the two-chain inhibitor C2 (FIG. 1). Three of the inhibitors (C1, C2 and T4) are identical to those released from the six-domain precursor. Related multidomain precursors have been described for other solanaceous plants including *N. tabacum* (Balandin et al., *Plant Mol. Biol.* 27: 1197-1204, 1995), *N. glutinosa* (Choi et al., *Biochim. et Biophys. Acta* 1492: 211-215, 2000), *L. esculentum* (Taylor et al., *Plant Mol. Biol.* 23: 1005-1014, 1993) and *Capsicum annum* (Moura and Ryan, *Plant Physiol.* 126: 289-298, 2001; Antcheva et al., *Protein Sci.* 10: 2280-2290, 2001).

Several groups have reported on the affect of serine proteinase inhibitors on the activity of the digestive proteases of insects and have suggested that they are produced by plants for protection against the damaging affects of insect pests and microorganisms (Ryan, *Annu. Rev. Phytopathol.* 28: 425-449, 1990; Gatehouse et al., In: *Plant Genetic Manipulation for Crop Protection,* Biotech. in Agriculture No. 7, Eds. Gatehouse, Hilder & Boulter, International U.K., pp. 155-181, 1992). Insects that are specialist feeders on a particular host plant are generally resistant to the serine PIs produced by that plant, but are sensitive to PIs produced by non-hosts (Broadway and Villani, *Entomol. Expo. Appl.* 76: 303-312, 1995; Broadway, *J. Insect. Physiol.* 41: 107-116, 1995). There is interest, therefore, in transferring genes encoding serine PIs from non-hosts into crop plants to enhance insect resistance and to decrease reliance on chemical pesticides. Recently, however, several groups have reported on the ability of certain insects to change the relative proportions of proteolytic enzymes in their midgut following ingestion of high levels of PIs (Broadway, 1995, supra; Jongsma et al., *Proc. Natl. Acad. Sci. USA* 92(17): 8041-8045, 1995a). Broadway (1995, supra), for example, found that certain lepidopteran insects produce two broad classes of trypsin like proteases, one of which is insensitive to PIs from cabbage leaves. After ingestion of the cabbage PIs the insects increased production of the trypsin class not affected by the PIs and thus were able to grow and develop unhindered. Jongsma and coworkers (1995, supra) made a similar observation with *Spodoptera exigua* larvae fed on PIs from potato (PotII) and tobacco. The factors that regulate the secretion of these proteases under these conditions are not known.

These studies indicate that PIs specific for only one or two of the range of proteinases in an insect gut will be of limited use for long term plant protection. The gene encoding the *N.alata* PI has a potential advantage over other plant PIs for the enhancement of insect resistance in transgenic plants. Most plant serine PIs contain only one or two inhibitory domains, whereas the *N. alata* PI precursors have four or six (FIG. 1). Thus, there is potential to engineer the individual domains of the *N. alata* PI to provide inhibitory activity against several proteinases in the insect gut.

The midgut proteases of several *Lepidoptera, Coleoptera* and *Orthoptera* have been partially characterized. In most *Lepidopteran* species the endoproteinase activity is due primarily to serine proteinases (trypsin, chymotrypsin and/or elastase) and cysteine and metalloproteinases are not detectable (Christeller et al., *Insect Biochem. Molecul. Biol.* 22: 735-746, 1992; Terra and Ferreira, *Comp. Biochem. Physiol.* 109: 1-62, 1994; Xu and Qin, *J. Econ. Entomol.* 87: 334-338, 1994; Lee and Anstee, *Insect. Biochem. Molec. Biol.* 25: 63-71, 1995a; Johnston et al., *Insect Biochem.* 21: 389-397, 1991; Johnston et al., *Insect Biochem. Molec. Biol.* 25(3): 375-383, 1995). Exopeptidase and leucineaminopeptidase have also been identified (Christeller et al., 1992, supra; Lee and Anstee, *Insect. Biochem. Molec. Biol.* 25(1): 49-61, 1995b).

The mechanism of action of PIs on insects is only partially understood. Three responses have been described:

(i) Severe retardation of growth without a decrease in gut proteolytic activity. Broadway and Duffey (*J. Insect*

*Physiol.* 32: 673-680, 1986a; Broadway and Duffey, *J. Insect Physiol.* 32: 827-833, 1986b) found that insects fed on PIs had remarkably reduced growth rates that were not associated with a decrease in the total proteolytic activity in the gut. Indeed the gut proteolytic activity often increased. They suggested that a feedback mechanism was operating that led to hyperproduction of proteases, that led in turn to a depletion of essential sulphur containing amino acids. This phenomenon has been recorded for other insects after chronic ingestion of PIs (Burgess et al., *Entomol. Exp. App.* 61: 123-130, 1991; De Leo et al., *Plant Physiol.* 118: 997-1004, 1998; Markwick et al., *J. Economic Entomology* 91 (6): 1265-76, 1998).

(ii) Severe retardation of growth with a decrease in gut proteolytic activity. Broadway (1995, supra) found that the lepidopteran species, *Agrotis ipsilon* (black cutworm) had reduced growth and delayed pupation after exposure to soybean trypsin inhibitor and did not respond by secreting PI-insensitive proteases. These insects had up to a 70% reduction in total gut proteolytic activity. Codling moth larvae (*Lepidoptera:Tortricidae*) fed on 'elastase inhibitors' were also retarded in growth and development that was associated with diminished elastase activity in the gut (Markwick et al., *Journal of Economic Entomology* 88(1): 33-39, 1995).

(iii) No effect on growth—change in the complement of gut proteinases. Some insects can compensate for the inhibition of one group of proteinases by inducing a new proteinase activity. The genomes of lepidopteran insects contain genes for a range of serine proteases and insects can modify the expression of specific isozymes to suit dietary components (Bown, et al., *Insect Biochem. Molec. Biol.* 27: 625-638, 1997; Broadway, *J. Insect. Physiol.* 43(9): 855-874, 1997). Changes in the complement of gut trypsins and chymotrypsins have been detected using Northern blot analysis on RNA from *H. armigera* (Bown, et al., 1997, supra; Gatehouse, et al., *Insect Biochem. Molecul. Biol.* 27: 929-944, 1997), *H. zea* and *Agrotis ipsilon* (Mazumdar-Leighton and Broadway, *Insect Biochem. Mol. Biol.* 31: 645-657, 2001a; Mazumdar-Leighton and Broadway, *Insect Biochem. Mol. Biol.* 31:633-644, 2001b). Corresponding changes at the protein level have also been observed using electrophoretic separation of isozymes for *H. armigera* (Harsulkar, et al., *Plant Physiol.* 121: 497-506, 1999; Patankar, et al., *Insect Biochem. & Mol. Biol.* 31: 453-464, 2001), *Spodoptera frugiperda* (Paulillo, et al., *J. Econ. Entomol.* 93:892-896, 2000), *H. zea* and *Trichoplusia ni* (Broadway, *Arch. Insect Biochem. Physiol.* 32(I): 39-53, 1996). Sometimes specific isozymes have been up-regulated, and occasionally proteases previously undetected have been observed.

Recently, Mazumdar-Leighton and Broadway (2001a, supra) demonstrated that the production of PI-insensitive trypsins in *H. zea* is regulated at the transcriptional level and can be abolished using the transcriptional regulator actinomycin. Broadway and colleagues examined changes in gut trypsin and chymotrypsin activity after *H. zea* and *Trichoplusia ni* larvae were fed for 48 h on artificial diet containing 1% SBTI (Broadway, 1996, supra). Trypsin activity increased after SBTI consumption and protease banding patterns on zymograms indicated a change in the relative complement of proteases. The researchers showed in vitro that SBTI could inhibit 74% of the trypsin activity in gut extracts from control larvae, but only 3% of the gut trypsin activity in larvae that had consumed SBTI. They suggested the new protease bands (one new band for *H. zea* and 6 new bands for *T. ni*) on the zymograms may be SBTI-insensitive trypsins or SBTI-insensitive chymotrypsins and concluded that the production of these new proteases was enhanced by the ingestion of SBTI. Further studies using Northern blot analysis showed that consumption of SBTI resulted in transcriptional induction of mRNAs encoding trypsins and chymotrypsins by *H. zea* and *Agrotis ipsilon* (Mazumdar-Leighton and Broadway, 2001a, supra; Mazumdar-Leighton and Broadway, 2001b, supra), although it was not determined if these proteases were SBTI-insensitive.

The novel trypsin transcript induced in *H. zea* after ingestion of SBTI was designated HzT15 (Mazumdar-Leighton and Broadway, 2001b, supra). Recently, the first insect digestive enzyme insensitive to several proteinase inhibitors was purified from the gut of *H. zea* and corresponds to the protein encoded by HzT15 (Volpicella et al., *Eur. J Biochem.* 270: 10-19, 2003). The authors identified several differences in charge distribution across the surface of the structural model of this PI-insensitive trypsin relative to the PI inhibitable trypsins, but were unable to identify the structural changes that led to resistance.

Until recently, chymotrypsins were assumed to contribute relatively little to protein digestion in *Lepidoptera* and consequently most biochemical studies focused on characterization of the trypsins. This problem arose due to the initial use of synthetic substrates that worked well with mammalian chymotrypsins, but not at all or poorly with the *Lepidopteran* enzymes. *Lepidopteran* chymotrypsins prefer synthetic substrates with at least four amino acids to occupy the S1-S4 binding subsites on the enzyme, whereas mammalian trypsins are active on shorter substrates with one amino acid that is specific for the S1 binding subsite. That is, the insect chymotrypsins appear to have an extended substrate binding site requiring at least four amino acids for efficient catalysis. Recent studies have shown that chymotrypsins do respond to PI ingestion and are worthy of more detailed investigation. When larvae from *H. armigera* were fed on diets consisting of either potato proteinase inhibitor II, soybean trypsin inhibitor, aprotin (trypsin inhibitor) or potato proteinase inhibitor I, levels of chymotrypsin mRNA increased in all cases while trypsin mRNA decreased (Gatehouse, et aL, 1997, supra). Other reports also mention upregulation of chymotrypsins in preference to trypsins (Bown et al., 1997, supra; Wu et al., *Molecular Breeding* 3: 371-380, 1997). Mazumdar-Leighton and Broadway (2001a, supra) assayed chymotrypsin activity in the gut of *H. zea* larvae and found that SBTI inhibited 95% of the chymotrypsin from the gut of control insects but only 35% of activity from the gut of insects that had prior exposure to SBTI in the diet.

Hence, consumption of proteinase inhibitors can lead to a drastic change in the complement of gut proteases which allows insects to adapt to the diet and survive. Changes in the complement of proteases after exposure to PIs have been detected in insects fed on both artificial diets and transgenic plants. The triggers that regulate these changes are still unknown and the responses vary with the species, the PI and its concentration, and the base diet. It is unclear why some inhibitors induce this response and others do not. It is clear, however, that some larvae are genetically pre-adapted to PIs, since prior exposure to a specific inhibitor is not necessary for an insect to be resistant (Broadway, 1996, supra).

There is a need to identify and investigate novel insect proteinases which are insensitive to PIs and to use these to screen for antagonists of the proteinases in order to develop agents useful in controlling insect growth, maintenance, development and/or survival.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided at the end of the specification.

The present invention provides a novel chymotrypsin from *Helicoverpa* spp. referred to herein as "HpCh5". Reference to "HpCh5" includes all variants, derivatives, homologs and analogs as well as members of a HpCh5 family of chymotrypsins. Examples of variants of HpCh5 include proteinase inhibitor (PI) sensitive forms. Such sensitive forms may carry inter alia a substitution of the arginine at position 192 to an asparagine or glutamine. This substitution is referred to herein as "R192N/Q" using single amino acid nomenclature or "Arg 192 Asn/Gln" using three letter amino acid code. Other derivatives of HpF5 include the signal sequence of HpF5.

The HpCh5 chymotrypsin is encoded by a nucleotide sequence referred to as "HpF5". Again, reference to "HpF5" includes variants, homologs and analogs thereof. The term "HpF5" encompasses both a genomic sequence as well as a cDNA sequence. The amino acid sequence of HpCh5 is set forth in SEQ ID NO:2. The amino acid sequence of the N-terminal activation peptide is shown in SEQ ID NO:3. The nucleotide sequence of the coding region of HpF5 is set forth in SEQ ID NO:4 with the nucleotide sequence encoding the activation peptide is shown in SEQ ID NO:5 and its entire 5'-3' sequence shown in SEQ ID NO:6. HpCh5 is generally characterized by being substantially insensitive to inhibition by a PI from *N. alata*.

Variants and homologs of HpCh5 include molecules having at least 75% amino acid identity to SEQ ID NO:2 after optimal alignment. Variants and homologs of HpF5 include nucleotide sequences having at least about 75% similarity to SEQ ID NO:4 or SEQ ID NO:6 after optimal alignment or a nucleotide sequence capable of hybridizing to SEQ ID NO:4 or SEQ ID NO:6 or its complementary form under low stringency conditions.

Accordingly, one aspect of the present invention provides an isolated nucleic acid molecule comprising a sequence of nucleotides encoding a chymotrypsin from *Helicoverpa* ssp. or a variant, derivative, homolog or analog of said chymotrypsin, wherein said chymotrypsin exhibits resistance to a PI from *N. alata*.

Another aspect of the present invention provides an isolated chymotrypsin from *Helicoverpa* ssp. wherein said chymotrypsin exhibits resistance to a PI from *N. alata* or a variant, derivative, homolog or analog of said chymotrypsin.

The present invention provides compounds which inhibit HpCh5 or its variants and homologs or members of the HpCh5 chymotrypsin family or which inhibit expression of the HpF5 gene or its variants and homologs.

The compounds may be chemical type compounds such as those sprayed or provided to plants or genetic type molecules which may be either topically applied or generated in plant cells. The HpCh5 or HpF5 antagonists may also be a modified form of an existing plant PI.

The present invention provides, therefore, methods for inhibiting insect infestation of a plant or for retarding insect growth and development by the application or dispersement of an antagonist of HpCh5 activity or HpF5 gene expression.

The antagonists include compounds which bind to and inhibit HpCh5 as well as antisense or sense nucleic acid molecules generated by a plant cell and then ingested by an insect.

Reference to an "antagonist" includes reference to an inhibitor.

The present invention further provides genetically modified plants which are engineered to produce a HpCh5 or HpF5 antagonist. Reference to a "plant" includes a monocotyledonous or dicotyledonous plant and may be a plant regenerated from genetically transformed callus or tissue or progeny of such a plant. The present invention further provides seeds and other reproductive material from the genetically modified plants of the present invention.

Plants contemplated herein include cotton, sweet corn, tomato, tobacco, piniento, potato, sunflower, citrus, plums, sorghum, leeks, soybean, alfalfa, beans, pidgeon peas, chick peas, artichokes, curcurbits, lettuce, *Dianthus* (an ornamental plant) and geraniums, cape gooseberry, maize, flax and linseed, alfalfa, lupins, broad beans, garden peas, peanuts, canola, snapdragons, cherry, sunflower, pot marigolds, *Helichrysum* (an ornamental plant), wheat, barley, oats, triticale, carrots, onions orchids, roses and/or petunias.

The present invention further provides nucleic acid molecules which encode potato-derived protenase inhibitors such as but not limited to Pot1A and Pot1B or their homologs or derivatives as well as transgenic plants comprising and capable of expressing same.

Yet another aspect of the present invention contemplates a method for screening for an inhibitor of an insect chymotrypsin which is insensitive to inhibition by NaPI such as HpCh5. Such a method generally involves testing for chymotryptic activity in the presence of potential inhibitors. The assay is conveniently contacted in vitro although the use of *H. argmigera* and/or *H. punctiga* is also encompassed by the present invention. An isolated inhibitor identified by the subject assay is also contemplated by the present invention.

A summary of sequence identifiers used throughout the subject specification is provided in Table 1.

TABLE 1

Summary of sequence identifiers

| SEQUENCE ID NO: | DESCRIPTION |
| --- | --- |
| 1 | linker sequence |
| 2 | Amino acid sequence of HpCh5 [FIG. 12] |
| 3 | Amino acid sequence of the activation peptide of HpCh5 [FIG. 12] |
| 4 | Nucleotide sequence of coding region of mature chymotrypsin domain of HpF5 [FIG. 12] |
| 5 | Nucleotide sequence of activation peptide of HpF5 [FIG. 12] |
| 6 | Nucleotide sequence encoding activation peptide and HpCh5 mature chymotrypsin domain together with 3' UTR [FIG. 12] |
| 7 | BamHI oligonucleotide primer |
| 8 | HindIII oligonucleotide primer |
| 9 | N-terminal sequence of NaPI-insensitive chymotrypsin HpCh5 [Table 7, FIG. 11B] |
| 10 | Fw2ResChy primer [Table 7, FIG. 11B] |
| 11 | FwResChym primer [Table 7, FIG. 11B] |
| 12 | Hc35PQE-60-Fw primer |
| 13 | Hc35PQE-60-Rv primer |
| 14 | gene specific sense primer |
| 15 | gene specific antisense primer |
| 16 | StPot1A sense primer |
| 17 | StPot1B sense primer |

TABLE 1-continued

Summary of sequence identifiers

| SEQUENCE ID NO: | DESCRIPTION |
|---|---|
| 18 | StPotIA/B antisense primer |
| 19 | FWBacRECH1 (5'-3') primer |
| 20 | FWBacRECH2 (5'-3') primer |
| 21 | RvRECH (3'-5') primer |
| 22 | N-terminal amino acid sequence of six domain PI precursor from *N. alata* [FIG. 1C] |
| 23 | Amino acid sequence of C1 peptide from six domain PI precursor from *N. alata* |
| 24 | Amino acid sequence of T1 peptide from six domain PI precursor from *N. alata* |
| 25 | Amino acid sequence of T2 and T3 peptides from six domain PI precursor from *N. alata* |
| 26 | Amino acid sequence of T4 peptide from six domain PI precursor from *N. alata* |
| 27 | C-terminal amino acid sequence of six domain PI precursor from *N. alata* |
| 28-31 | Amino acid sequence of peptide fragment of *Helicoverpa punctigera* chymotrypsin [FIG. 5B] |
| 32 | Amino acid sequence of chymotrypsin from *H. armigera* (CAA72966) [FIG. 7] |
| 33 | Amino acid sequence of chymotrypsin from *H. armigera* (CAA72959) [FIG. 7] |
| 34 | Amino acid sequence of chymotrypsin from *H. armigera* (CAA72960) [FIG. 7] |
| 35 | Amino acid sequence of chymotrypsin from *H. armigera* (CAA72958) [FIG. 7] |
| 36 | Amino acid sequence of chymotrypsin from *H. armigera* (CAA72952) [FIG. 7] |
| 37 | Amino acid sequence of chymotrypsin from *H. armigera* (CAA72951) [FIG. 7] |
| 38 | FWG1 primer [FIG. 8] |
| 39 | RVG4 primer [FIG. 8] |
| 40 | Y79Fw primer [FIG. 8] |
| 41 | Y72Fw primer [FIG. 8] |
| 42 | Y72Rv primer [FIG. 8] |
| 43 | Amino acid sequence of *H. punctigera* chymotrypsin (F1Apcr) [FIG. 9] |
| 44 | Amino acid sequence of *H. punctigera* chymotrypsin (F1Bpcr) [FIG. 9] |
| 45 | Amino acid sequence of *H. punctigera* chymotrypsin (F2Bpcr) [FIG. 9] |
| 46 | Amino acid sequence of *H. punctigera* chymotrypsin (F3pcr) [FIG. 9] |
| 47 | Amino acid sequence of *H. punctigera* chymotrypsin (F4pcr) [FIG. 9] |
| 48 | Amino acid sequence of chymotrypsin from *H. punctigera* (HpCh1AI) [FIG. 10] |
| 49 | Amino acid sequence of chymotrypsin from *H. punctigera* (HpCh1BI) [FIG. 10] |
| 50 | Amino acid sequence of chymotrypsin from *H. punctigera* (HpCh2A) [FIG. 10] |
| 51 | Amino acid sequence of chymotrypsin from *H. punctigera* (HpCh2B) [FIG. 10] |
| 52 | Amino acid sequence of chymotrypsin from *H. punctigera* (HpCh3A) [FIG. 10] |
| 53 | Amino acid sequence of chymotrypsin from *H. punctigera* (HpCh4I) [FIG. 10] |
| 54 | Amino acid sequence of chymotrypsin from *H. punctigera* (HpCh4II) [FIG. 10] |
| 55 | Amino acid sequence of peptide from *H. punctigera* chymotrypsin (Rech1a) [FIG. 11A] |
| 56 | Amino acid sequence of peptide from *H. punctigera* chymotrypsin (Rech1b) [FIG. 11A] |
| 57 | Amino acid sequence of peptide from *H. punctigera* chymotrypsin (Family1a) [FIG. 11A] |
| 58 | Amino acid sequence of peptide from *H. punctigera* chymotrypsin (Family1b) [FIG. 11A] |
| 59 | Amino acid sequence of peptide from *H. punctigera* chymotrypsin (Family2b) [FIG. 11A] |
| 60 | Amino acid sequence of peptide from *H. punctigera* chymotrypsin (Family2a) [FIG. 11A] |
| 61 | Amino acid sequence of peptide from *H. punctigera* chymotrypsin (Family3) [FIG. 11A] |
| 62 | Amino acid sequence of peptide from *H. punctigera* chymotrypsin (Family4) [FIG. 11A] |
| 63 | Amino acid sequence of *H. punctigera* chymotrypsin (HpCh1AI) [FIG. 13] |
| 64 | Amino acid sequence of *H. punctigera* chymotrypsin (HpCh1BI) [FIG. 13] |
| 65 | Amino acid sequence of *H. punctigera* chymotrypsin (HpCh2B) [FIG. 13] |
| 66 | Amino acid sequence of *H. punctigera* chymotrypsin (HpCh2A) [FIG. 13] |
| 67 | Amino acid sequence of *H. punctigera* chymotrypsin (HpCh3) [FIG. 13] |
| 68 | Amino acid sequence of *H. punctigera* chymotrypsin (HpCh4I) [FIG. 13] |
| 69 | Amino acid sequence of *H. punctigera* chymotrypsin (HpCh5) [FIG. 13] |
| 70 | Amino acid sequence of human brain trypsin (TrypsinIV) [FIG. 13] |
| 71 | Amino acid sequence of chymotrypsin from *H. armigera* [FIG. 14] |
| 72 | Amino acid sequence of chymotrypsin from *H. punctigera* [FIG. 14] |
| 73 | Amino acid sequence of bovine chymotrypsin B (BOV CHB) [FIG. 15] |
| 74 | Amino acid sequence of bovine chymotrypsin A (BOV CHA) [FIG. 15] |
| 75 | Amino acid sequence from *H. punctigera* (HpCh2A) [FIG. 15] |
| 76 | Amino acid sequence from *H. punctigera* (HpCh5) [FIG. 15] |
| 77 | Amino acid sequence of potato inhibitor I family (PotI) {StPotIB} [FIG. 24] |
| 78 | Amino acid sequence of potato inhibitor I family (PotI) {X67950} [FIG. 24] |
| 79 | Amino acid sequence of potato inhibitor I family (PotI) {R01052} [FIG. 24] |
| 80 | Amino acid sequence of potato inhibitor I family (PotI) {M17108} [FIG. 24] |
| 81 | Amino acid sequence of potato inhibitor I family (PotI) {StPotIA} [FIG. 24] |
| 82 | Amino acid sequence of potato inhibitor I family (PotI) {K03290} [FIG. 24] |
| 83 | Amino acid sequence of potato inhibitor I family (PotI) {Z12619} [FIG. 24] |
| 84 | Amino acid sequence of potato inhibitor I family (PotI) {X78988} [FIG. 24] |
| 85 | Amino acid sequence of potato inhibitor I family (PotI) {EILXCH} [FIG. 24] |
| 86 | Nucleotide sequence encoding endoplasmic reticulum peptide [FIG. 28] |
| 87 | Amino acid sequence of endoplasmic reticulum peptide [FIG. 28] |
| 88 | Nucleotide sequence of FwBacRECH1 primer [FIG. 28] |
| 89 | Nucleotide sequence of FwBacRECH2 primer [FIG. 28] |
| 90 | Nucleotide sequence of HpF5 to which DNA encoding endoplasmic reticulum signal is to be added [FIG. 28] |
| 91 | Amino acid sequence of HpCh5 to which endoplasmic reticulum signal is to be added [FIG. 28] |
| 92 | Nucleotide sequence of RvRECH primer [FIG. 28] |
| 93 | Amino acid sequence of HpCHY1 [FIG. 4C] |

BRIEF DESCRIPTION OF THE FIGURES

FIG. 4 is a photographic representation showing purification and N-terminal sequence of an NaPI inhibitable chymotrypsin from *H. punctigera* gut. (A and B) Protein gel analysis of fractions at various stages of purification using an affinity column with immobilized C1 inhibitor (FIG. 1). (A) 15% ((w/v)) SDS-polyacrylamide gel loaded with (a) unfractionated gut extract (b) and (c) unbound proteins. (B) 12.5% (w/v) SDS-polyacrylamide gel loaded with (d) wash fraction (e) protein bound to the C1 column. (C) N-terminal sequence of the ~24 kDa protein in lane (e).

FIG. 7 is a diagrammatic representation showing the design of oligonucleotide primers for amplification of chymotrypsins from *H. punctigera*. An alignment of chymotrypsins from *Helicoverpa armigera* predicted from DNA sequences in the GenBank database. NCBI protein database accession numbers are left of the sequences. Regions corresponding to the oligonucleotide primers are boxed and the direction of amplification are indicated by arrows.

FIG. 8 is a diagrammatic representation showing oligonucleotide sequences used in RT-PCR amplification of *Helicoverpa* chymotrypsins.

FIG. 9 is a diagrammatic representation showing PCR products from amplification of cDNAs encoding *H. punctigera* chymotrypsins. PCR amplification of cDNA prepared from gut mRNA yielded partial sequence for five distinct chymotrypsins. The translated sequence is aligned and the region corresponding to the PCR primers is boxed.

FIG. 10 is a diagrammatic representation showing alignment of predicted amino acid sequence of chymotrypsins from *H. punctigera*. The catalytic residues are marked by a solid triangle (▼). The highly conserved active site motifs are highlighted with grey. The dipeptide R-I (↓↓), conserved among all chymotrypsins is the site for the proposed cleavage of the activation peptide by trypsin. The residues that lie in the substrate binding pocket and confer substrate specificity are indicated by the symbols ¥,§,#. The cysteine (●) residues are highly conserved among all chymotrypsins.

FIG. 11 is a diagrammatic representation showing design of oligonucleotide primers for amplification of cDNA encoding the NaPI-insensitive chymotrypsins from *H. punctigera*. (A) Comparison of the N-terminal sequence of two NaPI-insensitive chymotrypsins with *Helicoverpa* chymotrypsins predicted from the cDNA clones. The unique regions F1 and F2 are shaded. (B) Oligonucleotide primers complementary to unique regions at the N-terminus of the insensitive chymotrypsin.

FIG. 12 is a diagrammatic representation showing nucleotide sequence and deduced amino acid sequence from the cDNA encoding the insensitive chymotrypsin. The nucleotide sequence of the insensitive chymotrypsin cDNA and deduced amino acid sequence. The amino acid sequence obtained from N-terminal sequence of purified protein is shaded in grey. The putative site for endoproteolytic cleavage by trypsin is shown by the arrow. The double underlined regions in the nucleotide sequence refer to the positions of the degenerate primers used for PCR amplification. The polyadenylation signal sequence is single underlined and an asterisk marks the stop codon. The deduced amino acid sequence of the putative activation peptide is numbered −40 to −1 followed by the mature domain (+1). The three amino acids that correspond to the catalytic residues are marked by the symbol #. The chymotrypsin substrate specificity residue, serine, located at the base of the primary substrate-binding pocket is marked with the symbol §.

FIG. 13 is a representation showing alignment of *H. punctigera* chymotrypsin families showing sequence identity. ClustalW alignment of members from the five families of *H. punctigera* chymotrypsins. Protein sequence is given in single letter code. Identical amino acids are coloured black, similar amino acids are grey. Amino acids are numbered on the right and gaps have been introduced to maximize the alignment. The NaPI-insensitive chymotrypsins are members of family 5 and are characterized by a unique arginine residue (arrowed) at position 185. Human trypsin IV also contains an arginine residue (arrowed) in a similar position.

FIG. 14 is a representation showing alignment of the *H. punctigera* NaPI-insensitive chymotrypsin with a homolog from *H. armigera* that also has an arginine residue at position 185.

FIG. 15 is a representation showing the deduced protein sequences for the insensitive (HpCh5) and sensitive (HpCh2A) chymotrypsins from *H. punctigera* aligned to the bovine chymotrypsin isoforms A and B. *H. punctigera* chymotrypsins HpCh2A and HpCh5 were aligned to the bovine chymotrypsin isoforms A and B using ClustalW. The numbering system (excluding gaps) is according to the nomenclature of Greer, *Proteins* 7: 317-34, 1990 used for bovine chymotrypsin. Dots throughout the sequences represent conserved residues. The regions shaded in grey designate residues that form surface loops that are involved in recognition and binding of substrates or inhibitors. The primary substrate-binding pocket is formed by the regions labeled S1A, S1B and S1C. The S1' site is formed by loops 35 and 60. Black boxes mark residues in the HpF5 sequence that differ significantly to amino acids in the corresponding positions in other chymotrypsins. Using the Greer, 1990, supra nomenclature these residues are Asp36, Arg 63, Thr72, Pro 83, Gly 109, Ileu 120, Glu insertion between 129 and 130, Glu 134, Ser145, Arg 192 and Pro 207. The boxed amino acids are removed from bovine chymotrypsins by autocatalytic cleavage that results in the formation of α-chymotrypsin.

SDS-PAGE gel and stained with Coomassie Blue. Panel 2: Identical sample to Panel 1 transferred to nitrocellulose and immunostained with anti-HpCh2B antibodies. (C) Decreasing amounts (200, 150, 100, 75, 50, 25, 20, 10, 0 ng) of bacterially expressed chymotrypsin HpCh2B separated by SDS-PAGE and stained with silver and a protein blot of an identical gel probed with anti-chymotrypsin HpCh2B antibodies (1/2500). The *H. punctigera* antibody had a detection limit of 20 ng of bacterially expressed protein.

Figure 21:
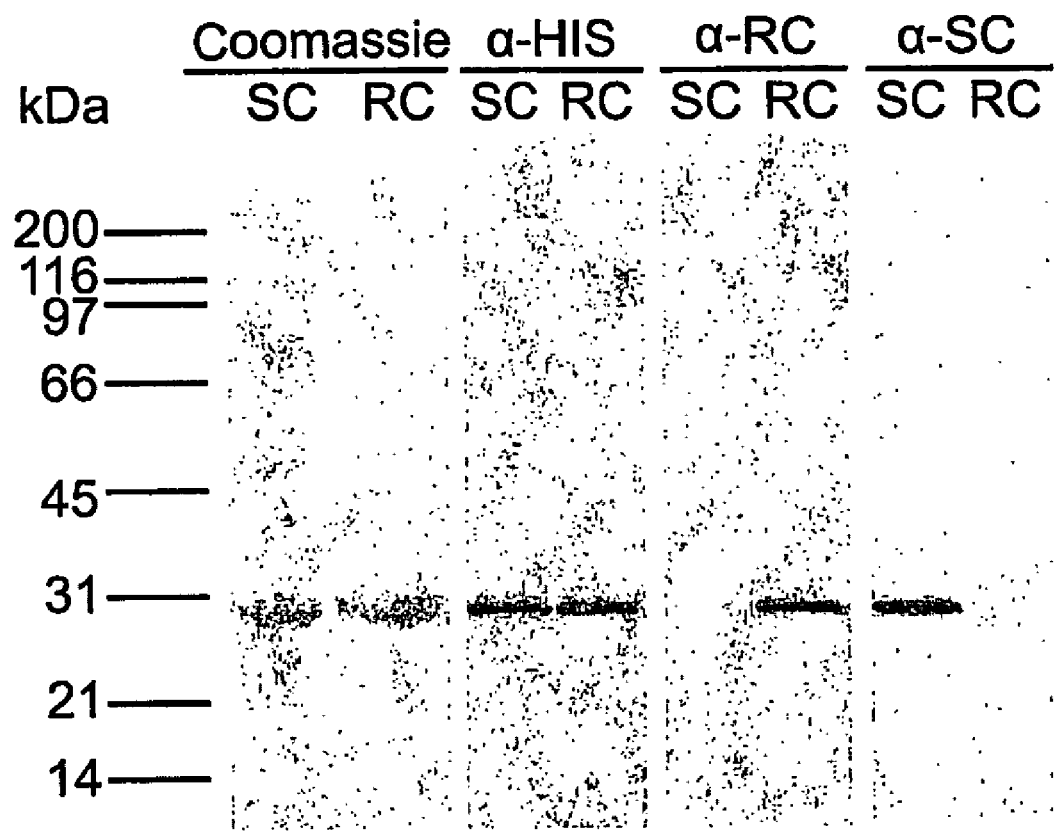

FIG. 21 is a photographic representation showing specificity of antibodies raised against bacterially expressed NaPI-insensitive (HpCh5) and sensitive (HpCh2B) chymotrypsins from *H. punctigera*. Bacterially expressed NaPI-insensitive (R) and sensitive (C) chymotrypsins were separated by SDS-PAGE on 12.5% (w/v) polyacrylamide gels and (A) stained with Coomassie Blue, (B) immunoblotted with an α-His tag antibody, (C) immunoblotted with the antibody to the HpCh2B chymotrypsin (α-RC), and (D) immunoblotted with the antibody to the HpCh5 chymotrypsin (α-SC).

Figure 22A:
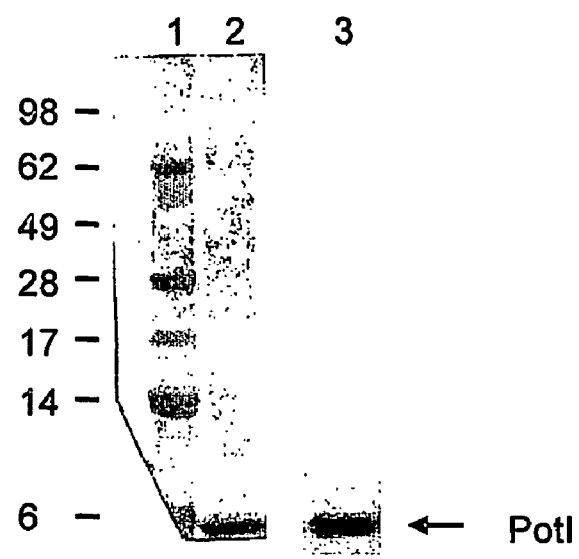
Figure 22B:
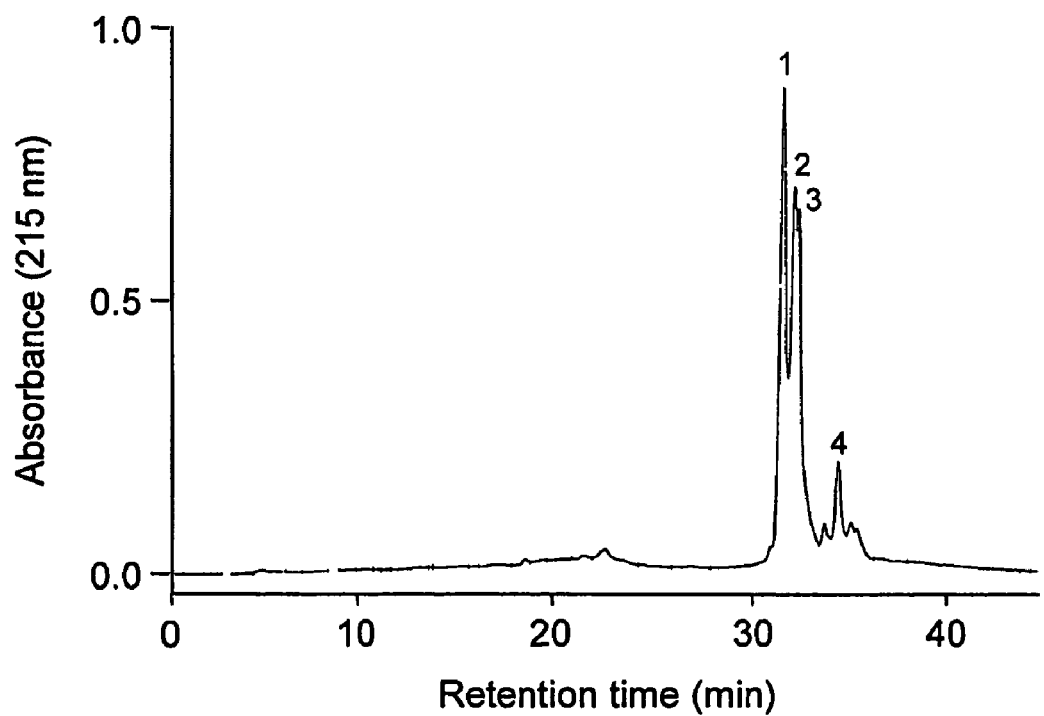

FIG. 22 are representations showing purification of PotI from potato tubers. PotI was purified from potato tubers (Russet Burbank) by acid extraction, ammonium sulphate precipitation and gel filtration. (A) SDS-PAGE stained with silver. lane 1: molecular size markers (kDa), lane 2: pooled PotI containing fractions from G-75 column, lane 3: immunoblot of lane 2 using an antibody raised in rabbits to a commercial preparation of PotI (Calbiochem) linked to keyhole limpet hemocyanin. PotI was identified as a single band with an approximate mass of 6 kDa. (B) RP-HPLC of pooled G-75 fractions from A. Peaks 1, 2 and 3 are PotI isoforms, peak 4 is a contaminating protein.

Figure 23:
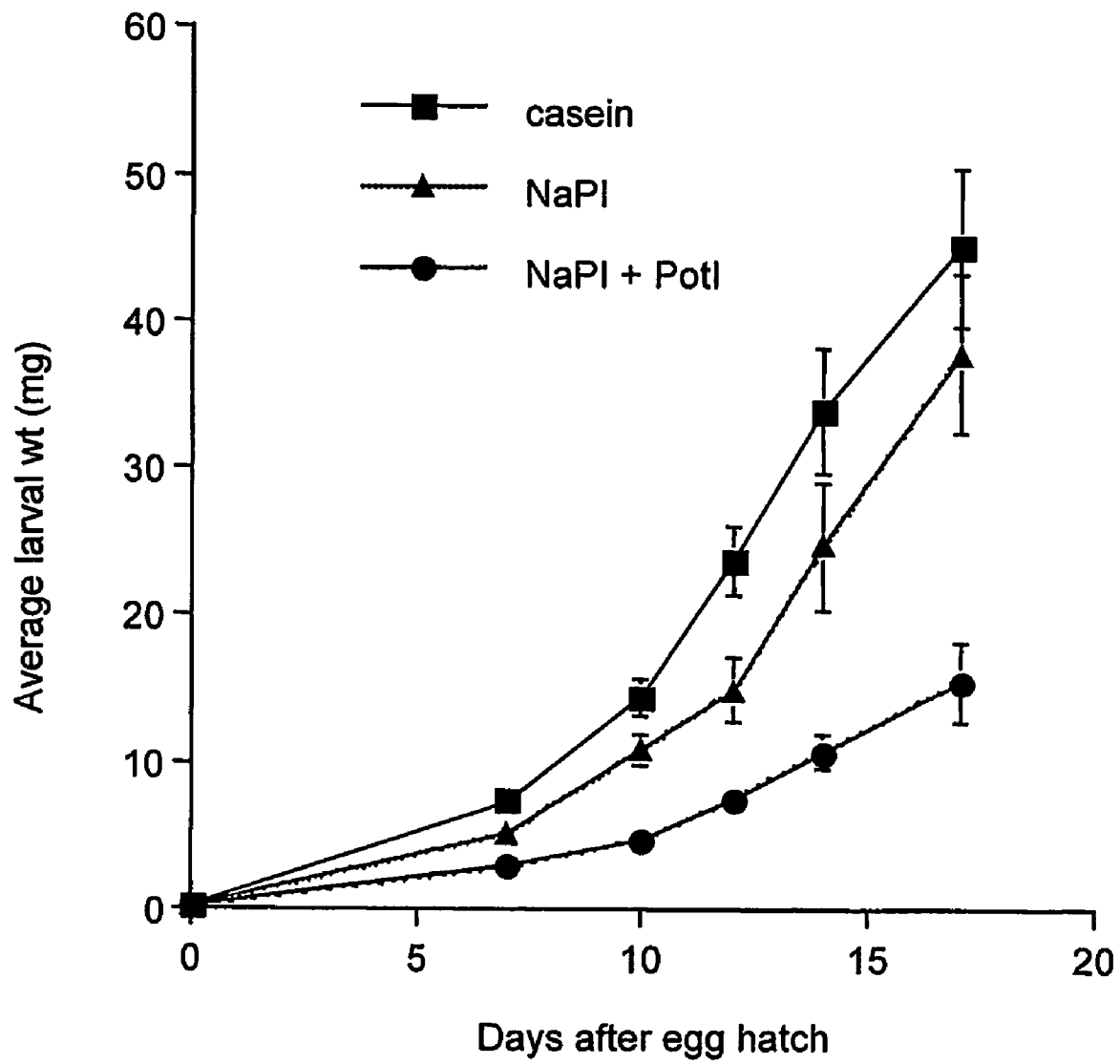

FIG. 23 is a graphical representation showing growth of *H. armigera* larvae on artificial diet containing NAPI and PotI. Growth of *H. armigera* larvae fed on a cotton leaf artificial diet in the presence or absence of 0.26% (w/v) NaPI or 0.26% (w/v) NAPI plus 0.26% (w/v) PotI. The PotI was purified from potato tubers (var Russet Burbank), see FIG. 22. Twenty five larvae were used on each diet. The weight of the larvae was measured at days 7, 10, 12, 14 and 17 post egg hatch. At day 17, larvae fed NaPI alone were 84% of the control and larvae fed NAPI and PotI were 34% of the control. Two larvae fed on the control diet died, seven larvae fed the NaPI diet died and six larvae fed on the NaPI plus PotI diet died.

FIG. 24 is a representation showing the alignment of predicted amino acid sequence of StPotIA and StPotIB with members of the potato Inhibitor I family. ClustalW alignment of several members of the Potato Inhibitor I family. X67950: potato cDNA, (Beuning and Christeller, *Plant Physiol* 102: 1061, 1993), P01052: potato protein (Richardson and Cossins, *FEBS Letters*, 52: 161, 1975), M17108: potato genomic sequence (Cleveland et al., *Plant Mol. Biol.* 8: 199-207, 1987), K03290: tomato (Graham et al., *J. Biol. Chem.*, 260: 6555-6560, 1985) Z12619: tobacco (Lindhorst et al., *Plant Mol. Biol.* 21: 985-992, 1993), X78988: maize (Jose Cordero et al., *Plant J.* 6: 141-150, 1994), EILXCH: leech (See Muller et al., *Hoppe-Seyler's Z. Physiol. Chem.* 358: 1105-1117, 1977). * P1 reactive site. Both StPotIA and StPotIB are similar to other family members from potato. However, StPotIA has an additional four amino acids at position 41 to 44 that are also found in a wound induced PotI from tomato (K03290). StPotIB has a methionine at the PI site which is common for potato isolates. StPotIA has an alanine at the PI site which has not been reported for PotI isolates from potato, but is present in a PotI isolate from maize (X78988).

Figure 25:
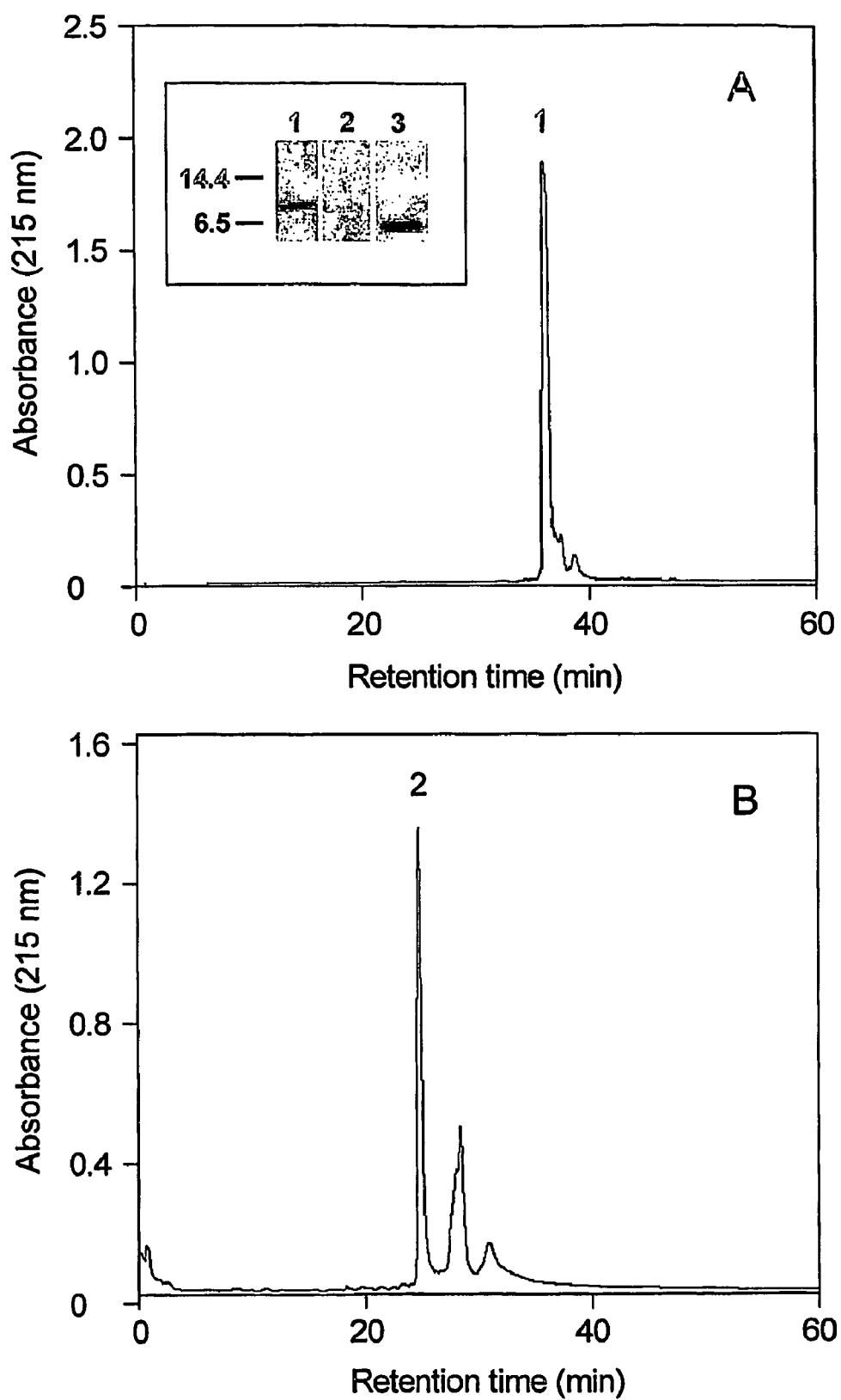

FIG. 25 is a graphical representation showing purification of *E. coli* expressed StPotIA and StPot1B. StPot1A and StPotIB were purified using the N-terminal HIS tag fused to StPot1A and StPotIB and a metal affinity resin followed by RP-HPLC. Profile after separation by RP-HPLC. Protein was eluted with a linear gradient of 0-100% Buffer B (80% (v/v) acetonitrile, 0.1% (v/v) TFA) at a flow-rate of 1 ml/min over 60 min. (A) StPotIA, (B) StPotIB. StPotIA eluted in one major peak at 36 min retention time (60% Buffer B) and StPotIB eluted in one major peak at 25 min retention time (42% Buffer B). The peaks were analyzed by SDS-PAGE and stained with silver (insert in A). Lane 1 is StPotIA (pk1), lane 2 is StPotIB (pk2) and lane 3 is purified PotI from potato tubers. StPotIA and StPotIB have a different apparent mobility (10 kDa) to a mix of PotI isoforms isolated from tubers (6 kDa), due to the additional HIS-tag epitope at the N terminus.

Figure 26:
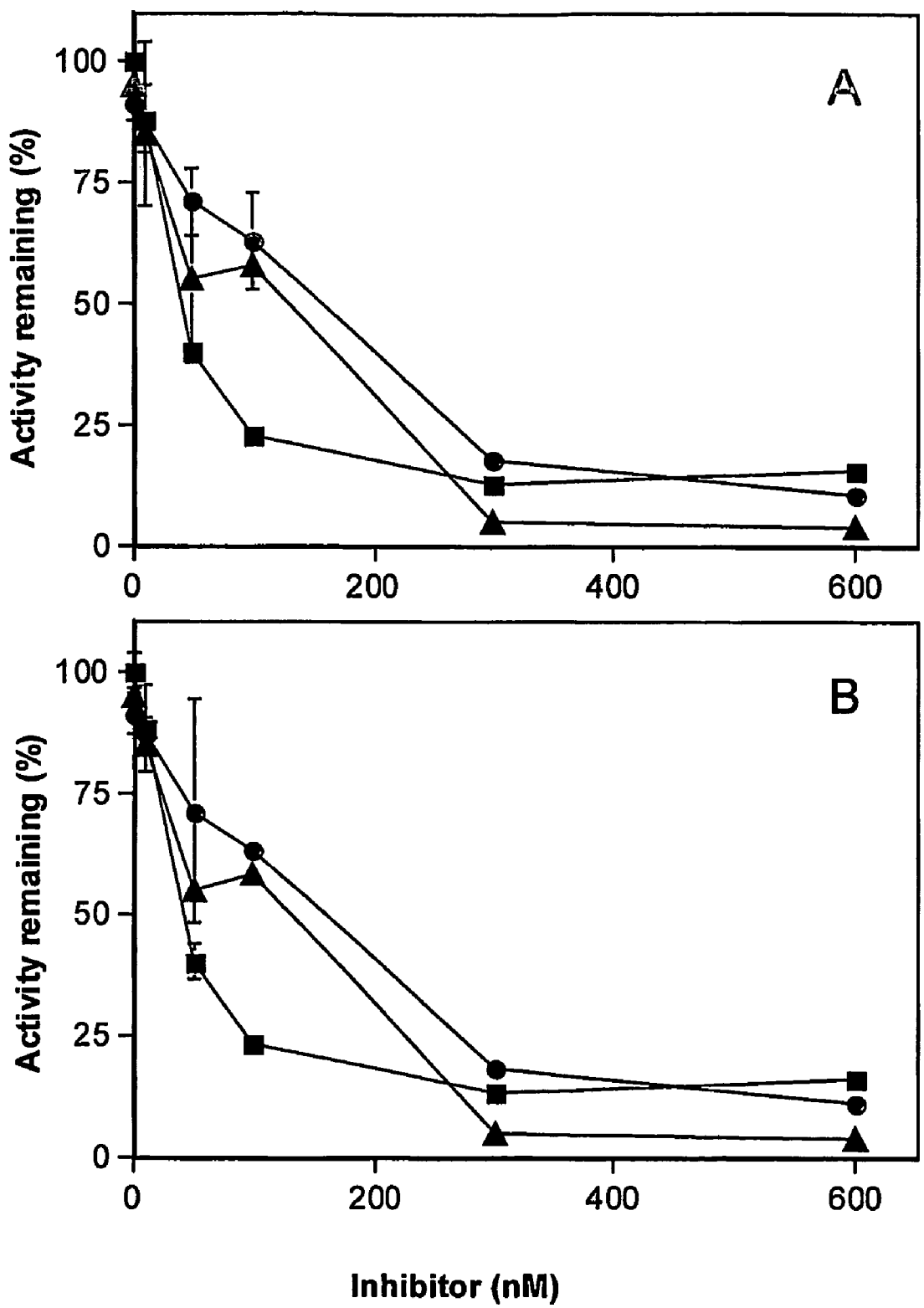

FIG. 26 is a graphical representation showing inhibition of NaPI-insensitive chymotrypsin by bacterially expressed StPotIA and StPotIB. Inhibition of the NAPI-insensitive chymotrypsin from the gut of *H. punctigera* with purified PotI. (A) substrate $SA_2PFpNA$, development time 30 min, (B) substrate $SA_2PLpNA$, 30 min incubation. Mix of PotI isoforms from potato tuber (circle), StPotIA (square), StPotIB (triangle). StPotIA, StPotIB and the PotI from potato tubers were good inhibitors of the NAPI-insensitive chymotrypsin.

Figure 27A:
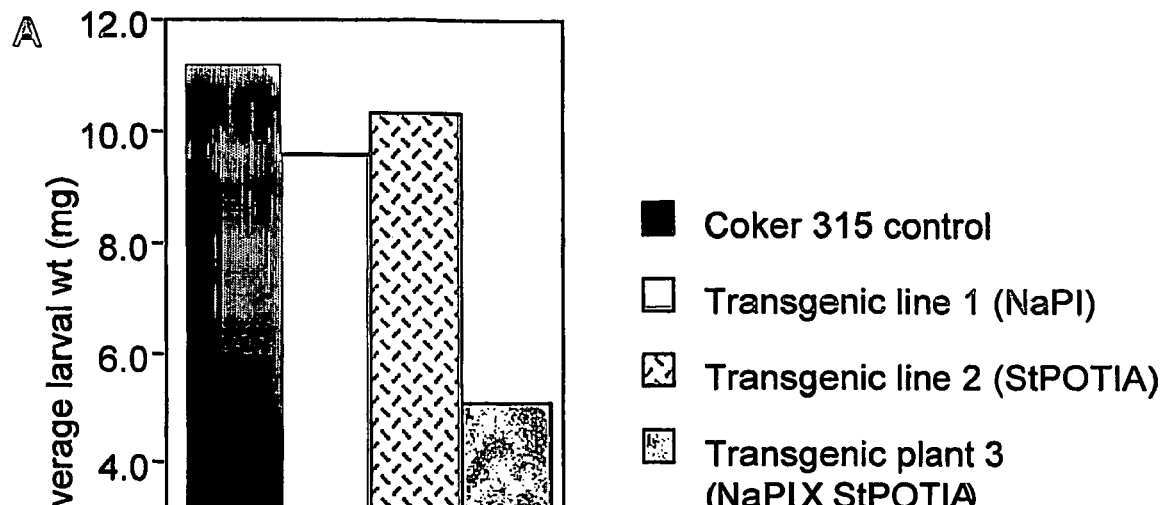
Figure 27B:
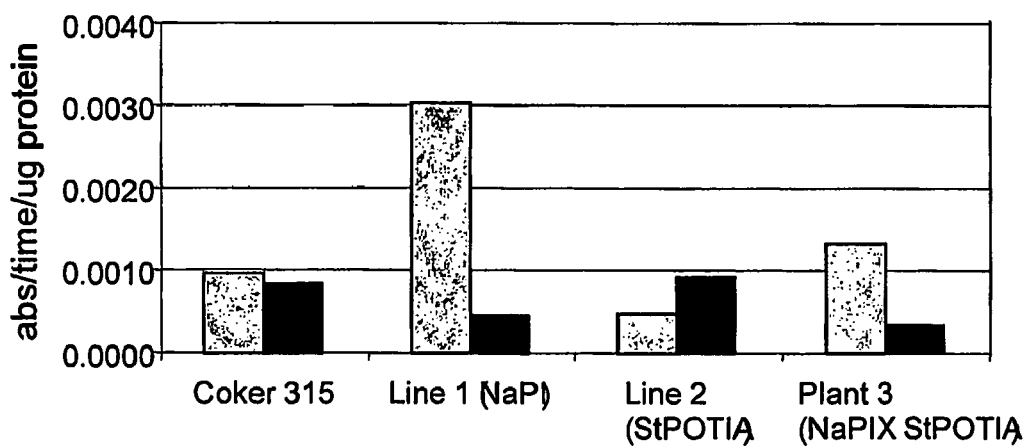

FIG. 27 is a graphical representation showing growth of *H. armigera* larvae on transgenic cotton expressing NaPI and PotI. Transgenic cotton cv Coker 315 was used in bioassays with *H. armigera*. Thirty larvae were fed leaves of either the control untransformed Coker 315, transgenic line 1 (NaPI), transgenic line 2 (StpotIA) or transgenic plant 3 (NaPI× StPot1A). The weight of the larvae was measured at day 7 post-egg hatch. (A) Growth of larvae. At day 7, larvae fed leaves expressing NaPI were 86% of the weight of the control larvae fed untransformed leaves. Larvae fed leaves expressing StPotIA were 92% of the control and larvae fed leaves expressing both NAPI and StPotIA were 46% of the control. (B) The effect of ingestion of NAPI and PotI on gut trypsin and chymotrypsin activity. Gut from the larvae in each experiment were pooled and extracts prepared. All assays were performed in duplicate. Trypsin activity (black) was determined using BApNA substrate and chymotrypsin activity (grey) with $SA_2PFpNA$ substrate. Units of activity are expressed as change in absorbance at 405 nm/min/ug gut extract protein. Trypsin activity was reduced, relative to the control, in the extracts from larvae fed leaves expressing NaPI and NaPI+StPotIA. Chymotrypsin activity was elevated in extracts from larvae fed leaves expressing NAPI or NAPI+ StPotIA and reduced in extracts from larvae fed StPotIA alone.

FIG. 28 diagrammatic representation showing the nucleotide sequence and deduced amino acid sequence from the HpF5 cDNA encoding the NaPI-insensitive chymotrypsin and the location of the oligonucleotide primers used to add an endoplasmic reticulum sequence to HpCh5. The FwBacRECH1 primer was used to add the first half of the ER signal sequence as well as a silent mutation, changing A to G to destroy the BamHI cut site. The FwBacRECH2 primer added the remainder of the coding sequence for the ER signal as well as a BamHI cut site to the 3' end of the sequence. The ER signal was added before the hexahistidine tag to enable purification of the expressed protein by metal affinity chromatography after cellular processing. The added amino acids are shaded in grey.

FIG. 29 is a photographic representation showing expression of the chymotrypsin clone HpF5 in baculovirus infected insect cells. Expressed proteins were separated on 12.5% (w/v) SDS-PAGE gels and subjected to immunoblots with the α-HpCh5-antibody (A) RCDNA. Production of HpCh5 by HIGH FIVE (trademark) insect cells transfected with 20 μl of bacmid DNA. Controls; (pFastBacVector) insect cells transfected with bacmid DNA transposed with pFastBac vector without the HpFSinsert; (blue colony) insect cells transfected with untransposed bacmid DNA; (cells alone) untransfected insect cells; (Cellfectin) insect cells treated with CELFECTIN (registered trademark) alone; The positive control, +is bacterially expressed HpCh5 with a hexahistidine tag. (B) Production of HpCh5 by HIGH FIVE (trademark) insect cells infected with virus. RC 24, 48 and 72. Medium collected 24, 48 and 72 hours after infection with HpF5 recombinant virus. Controls 24, 48 and 72. Medium from cells treated with virus prepared from nontransfected bachmid (blue colony) for 24, 48 and 72 hours. Positive control is bacterially expressed HpCh5 with a hexahistidine tag.

DETAILED DESCRIPTION OF THE INVENTION

The present invention is predicated in part on the identification and cloning of a novel insect chymotrypsin molecule termed "HpCh5". cDNA encoding HpCh5 is referred to herein as "HpF5". The isolation of this molecule permits the identification and design of a range of products which are useful in controlling the growth, development and/or overall biological fitness of *Helicoverpa* spp. and other insects. These products generally act as antagonists of HpCh5 function or HpF5 gene expression and are useful as insect control agents.

The amino acid sequence of HpCh5 is set forth in SEQ ID NO:2. The nucleotide sequence of HpF5 is set forth in SEQ ID NOs:4 and 6.

Reference herein to "HpCh5" should be understood as a reference to all forms of HpCh5 including, for example, any peptide isoforms which arise from alternative splicing of HpF5 mRNA, mutants or polymorphic variants of HpCh5, any post-translation modified forms of HpCh5 or any non-post-translational modified forms of HpCh5 as well as any homolog in other insect species or strains. The term "HpCh5" also encompasses members in a HpCh5 family of chymotrypsin molecules. To the extent that it is not specified, reference herein to HpCh5 includes derivatives, homologs, analogs, chemical equivalents and mimetics thereof. Reference to HpCh5 also refers to any variant having at least 75% amino acid identity to SEQ ID NO:2 after optimal alignment. Examples of variants of HpCh5 include PI-sensitive variants such as those inter alia having an Arg 192 Gln or Arg 192 Asn substitution. Other variants include the N-terminal signal sequence of HpCh5 as defined in SEQ ID NO:3 and which is encoded by the nucleotide sequence set forth in SEQ ID NO:5. Such variants include a signal sequence comprising an amino acid sequence having at least about 75% similarity to SEQ ID NO:3 after optimal alignment or encoded by a nucleotide sequence having at least about 75% identity to SEQ ID NO:5 or a nucleotide sequence capable of hybridizing to SEQ ID NO:5 after optimal alignment.

Reference to "HpF5" should be understood as reference to all forms of HpF5 including any cDNA isoform, genomic forms, mutants and polymorphic variants of HpF5 as well as any homologs from other species or strains of insect. The term "HpF5" also encompasses members of a HpF5 family of genes which encode HpCh5 or HpCh5-type chymotrypsins. To the extent that it is not specified, reference herein to HpF5 includes derivatives of HpF5 as well as a nucleotide sequence having at least about 75% identity to SEQ ID NO:4 or SEQ ID NO:6 or a nucleotide sequence capable of hybridizing to SEQ ID NO:4 or SEQ ID NO:6 or its complementary form under low stringency conditions. The signal sequence of HpF5 as defined in SEQ ID NO:3 and encoded by SEQ ID NO:5 also encompasses variants thereof. As indicated above, such variants include a signal sequence having at least about 75% similarity to SEQ ID NO:3 after optimal alignment and/or being encoded by a nucleotide sequence capable of hybridizing to SEQ ID NO:5 under low stringency conditions and/or a nucleotide sequence having at least about 75% identity to SEQ ID NO:5 after optimal alignment.

Before describing the present invention detail, it is to be understood that unless otherwise indicated, the subject invention is not limited to specific formulations of components, manufacturing methods, administration regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to an "agent" or "antagonist" includes a single agent or antagonist as well as two or more agents or antagonists and so forth.

In describing and claiming the present invention, the following terminology is used in accordance with the definitions set forth below.

The terms "compound", "agent", "active agent" and "active" are used interchangeably herein to refer to a chemical compound which inhibits the activity of HpCh5 or the expression of a genomic gene corresponding to HpF5. The terms also encompass agriculturally or horticultural active ingredients of those active agents specifically mentioned herein including but not limited to salts, esters, amides, prodrugs, active metabolites, analogs and the like. When the term "compound", "agent", "active agent" or "active" is used, then it is to be understood that this includes the agent per se as well as agriculturally or horticulturally acceptable, physiologically active salts, esters, amides, prodrugs, metabolites, analogs, etc. The term "compound" is not to be construed as a chemical compound only but extends to peptides, polypeptides and proteins as well as genetic molecules such as RNA, DNA and chemical analogs thereof.

The present invention contemplates, therefore, compounds useful in down-regulating the activity of HpCh5 or down-regulating expression of a genomic gene corresponding to HpCh5. The term "down-regulating" encompasses inhibition of HpCh5 activity. The inhibition of HpCh5 or reduction in its levels has the effect of reducing or retarding the growth of the insect. The inhibition of HpCh5 activity or HpF5 gene expression may occur by producing an inhibitor in a plant which is then consumed by the insect or the inhibitor may be topically applied to a plant or sprayed or otherwise dispersed to insects or a source of insects. In this regard, the plant may produce a nucleic acid molecule that interferes with HpF5 expression when consumed by the insect. Alternatively, the plant may produce a PI capable of inhibiting HpCh5. Still in a further alternative, the HpCh5 inhibitor is a non-proteinaceous chemical applied to the surface of a plant or taken up by the root system of a plant. Reference herein to a "plant" is not to exclude trees or cultured tissues (e.g. callus) from a plant (or tree).

Reference to compounds, agents and actives also includes combinations of compounds, agents or actives. Such combinations may be formulated in multi-part agricultural or horticultural compositions which are admixed together prior to dispersement or given sequentially.

The terms "effective amount", "insecticidal effective amount" and "insect-static effective amount" of an agent as used herein mean a sufficient amount of the agent to reduce or retard insect growth and development and/or to kill or inhibit the insect.

By "agriculturally acceptable" or "horticulturally acceptable" carrier, excipient or diluent is meant a vehicle comprised of a material that is not environmentally or otherwise undesirable to a plant or non-target insect. Carriers may include excipients and other additives such as diluents, detergents, coloring agents, wetting or emulsifying agents, pH buffering agents, preservatives, and the like.

The terms "treating" and "treatment" as used herein in relation to plants or eradication of insects refer to reduction in severity of symptoms of insect infestation of a plant or the application of the agents to a group of insects resulting in retardation of their growth, development or biological fitness or wellbeing.

The compounds of the present invention may be large or small molecules, nucleic acid molecules (including antisense or sense molecules), peptides, polypeptides or proteins or hybrid molecules such as RNAi- or siRNA-complexes, ribozymes or DNAzymes.

The term "nucleic acid molecule" is also encompassed by the expression "genetic molecule" and includes hairpin constructs such as those which include RNAi-mediated post-transcriptional gene silencing or methylation-mediated silencing.

Accordingly, one aspect of the present invention provides an isolated nucleic acid molecule or derivative, homolog or analog thereof comprising a nucleotide sequence encoding a novel chymotrypsin protein or a derivative, homolog or mimetic thereof wherein said chymotrypsin is insensitive to a PI of *N. alata*.

More particularly, the present invention is directed to a nucleic acid molecule or derivative, homolog or analog thereof comprising a nucleotide sequence encoding, or a nucleotide sequence complementary to a nucleotide sequence encoding, an amino acid sequence substantially as set forth in SEQ ID NO:2 or a derivative, homolog or mimetic thereof or having at least about 75% or greater identity to SEQ ID NO:2 after optimal alignment or a nucleotide sequence set forth in SEQ ID NO:4 or SEQ ID NO:6 or a nucleotide sequence having at least about 75% similarity or greater to SEQ ID NO:4 or SEQ ID NO:6 or a nucleotide sequence capable of hybridizing to SEQ ID NO:4 or SEQ ID NO:6 or its complementary form under low stringency conditions.

Another aspect of the present invention provides an isolated chymotrypsin *Helicoverpa* ssp. wherein said chymotrypsin exhibits resistance to a PI from *N. alata* or a variant, derivative, homolog or analog of said chymotrypsin.

More particularly, the isolated chymotrypsin comprises an amino acid sequence set forth in SEQ ID NO:2 or an amino acid sequence having at least about 75% similarity to SEQ ID NO:2 after optimal alignment.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and amino acid sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as, for example, disclosed by Altschul et al. (*Nucl. Acids Res.* 25: 3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity. The term "similarity" is particularly useful to describe amino acid sequence comparisons. The term "identity" is particularly useful to describe nucleotide sequence comparisons.

Reference to at least about 75% identity or 75% similarity includes percentage identities and similarities greater than 75% such as 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

Reference herein to a low stringency means from at least about 0 to at least about 15% (v/v) formamide (including 1%, 2%, 3%, 4%, 5%, 6%, 7%, 8%, 9%, 10% 11%, 12%, 13% and 14% (v/v) formamide) and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% (v/v) to at least about 30% (v/v) formamide and from at least about 0.5 M to at least about 0.9 M salt for hybridization, and at least about 0.5 M to at least about 0.9 M salt for washing conditions, or high stringency, which includes and encompasses from at least about 31% (v/v) to at least about 50% (v/v) formamide and from at least about 0.01 M to at least about 0.15 M salt for hybridization, and at least about 0.01 M to at least about 0.15 M salt for washing conditions. In general, washing is carried out $T_m = 69.3 + 0.41$ (G+C) % (Marmur and Doty, *J. Mol. Biol.* 5: 109, 1962). However, the $T_m$ of a duplex DNA decreases by 1° C. with every increase of 1% in the number of mismatch base pairs (Bonner and Laskey, Eur. *J. Biochem.* 46.: 83, 1974). Formamide is optional in these hybridization conditions. Accordingly, particularly preferred levels of stringency are defined as follows: low stringency is 6×SSC buffer, 0.1% (w/v) SDS at 25-42° C; a moderate stringency is 2×SSC buffer, 0.1% (w/v) SDS at a temperature in the range 20° C. to 65° C.; high stringency is 0.1×SSC buffer, 0.1% (w/v) SDS at a temperature of at least 65° C.

A further aspect of the present invention contemplates a nucleic acid molecule or derivative, homolog or analog thereof comprising a nucleotide sequence substantially as set forth in SEQ ID NO:4 or SEQ ID NO:6 or a nucleotide sequence having at least 75% or greater similarity to SEQ ID NO:4 or SEQ ID NO:6 or a derivative, homolog or analog thereof, or capable of hybridizing to SEQ ID NO:4 or SEQ ID NO:6 or its complementary form under low stringency conditions and which encodes an amino acid sequence substantially as set forth in SEQ ID NO:2 or a derivative, homolog or mimetic thereof or having at least 75% or greater identity to SEQ ID NO:2 after optimal alignment which nucleic acid molecule encodes a chymotrypsin which is insensitive to a proteinaceous inhibitor of *N. alata*.

Yet another aspect of the present invention contemplates nucleic acid molecule comprising a sequence of nucleotides substantially as set forth in SEQ ID NO:4 or SEQ ID NO:6. The nucleic acid molecule encoding HpCh5 is preferably a sequence of deoxyribonucleic acids such as a cDNA sequence or a genomic sequence. A genomic sequence may also comprise exons or introns. A genomic sequence may also include a promoter region or other regulatory regions. The present invention further contemplates isolated introns and exons of HpF5 such as those involved in genetic networking within a plant cell.

The nucleic acid molecule according to this aspect of the invention corresponds herein to HpF5. This cDNA has been determined, in accordance with the present invention, to encode a protein that defines a new family of chymotrypsins, family 5, within the group of chymotrypsin gene families, and this protein is referred to herein as HpCh5. Reference to "HpF5" also includes a genomic form of the gene. Within the *Helicoverpa punctigera* chymotrypsin gene families, there are varying levels of homology as shown in Table 2. Family 5 is exemplified by HpF5, and is most similar to family 2A at 73% and least similar to family 4 at <20%. Without intending to limit the instant invention in any way, HpCh5 is exemplified by two unique stretches of sequence in the N-terminal (F1 and F2) and by six amino acid substitutions relative to NaPI sensitive chymotrypsins. Five of these substitutions did not appear to fall into functionally significant regions, whereas the sixth substitution is associated with one of the β-strands that forms a wall of the primary substrate-binding pocket. The location of this substitution and conversion to an arginine, from glutamine, is highly unusual for the S1 domain that is predominantly lined with non-polar residues that define chymotrypsin specificity

TABLE 2

Percentage protein sequence identity between members of the *H. punctigera* chmotrypsin gene family

| H. punctigera chymotrypsin families | HpCh1AI | HpCh1BI | HpCh2A | HpCh2B | HpCh3A | HpCh3B | HpCh4AI | HpCh5 |
|---|---|---|---|---|---|---|---|---|
| HpCh1AI |  | 90 | 54 | 53 | 58 | 59 | <20 | 57 |
| HpCh1BI |  |  | 51 | 51 | 56 | 56 | <20 | 55 |
| HpCh2A |  |  |  | 94 | 83 | 87 | <20 | 73 |
| HpCh2B |  |  |  |  | 82 | 82 | <20 | 72 |
| HpCh3A |  |  |  |  |  | 92 | <20 | 70 |
| HpCh3B |  |  |  |  |  |  | <20 | 72 |
| HpCh4AI |  |  |  |  |  |  |  | <20 |

The present invention provides, therefore, an isolated protein having chymotrypsin activity which is not substantially inhibited by a PI from *N. alata*. Accordingly, another aspect of the present invention is directed to an isolated protein selected from the list consisting of:

(i) a novel chymotrypsin protein or a derivative, homolog or mimetic thereof wherein said chymotrypsin is insensitive to the proteinase inhibitors of *N. alata*;

(ii) a protein having an amino acid sequence substantially as set forth in SEQ ID NO:2 or a derivative, homolog or mimetic thereof or having at least 75% or greater identity to SEQ ID NO:2 after optimal alignment;

(iii) a protein encoded by a sequence of nucleotides substantially as set forth in SEQ ID NO:4 or SEQ ID NO:6 or a derivative, homolog or analog thereof or a nucleotide sequence having at least 75% similarity to SEQ ID NO:4 or SEQ ID NO:6 or a sequence encoding an amino acid sequence substantially as set forth in SEQ ID NO:2 or a derivative, homolog or mimetic thereof or having at least 75% or greater similarity to SEQ ID NO:2 after optimal alignment;

(iv) a protein encoded by a nucleic acid molecule or derivative, homolog or analog thereof comprising a nucleotide sequence substantially as set forth in SEQ ID NO:4 or SEQ ID NO:6 or a derivative, homolog or analog thereof, or capable of hybridizing to SEQ ID NO:4 or SEQ ID NO:6 under low stringency conditions and which encodes an amino acid sequence substantially as set forth in SEQ ID NO:2 or a derivative, homolog or mimetic thereof or having at least 75% or greater similarity to SEQ ID NO:2 after optimal alignment.

(v) a novel chymotrypsin protein or a derivative, homolog or mimetic thereof that has an arginine substituted for an asparagine or glutamine in the primary substrate-binding pocket.

The present invention discloses the amino acid, and corresponding cDNA sequence of a novel chymotrypsin that is insensitive to the Type II serine proteinase inhibitors produced by solanaceous species such as *N. alata*. Therefore, this may be used as a target for agents to control insects carrying this insensitive proteinase. A number of compounds have been shown to inhibit the activity of HpCh5, and a list of these compounds as preferred embodiments is found in Table 3.

Figure 16:
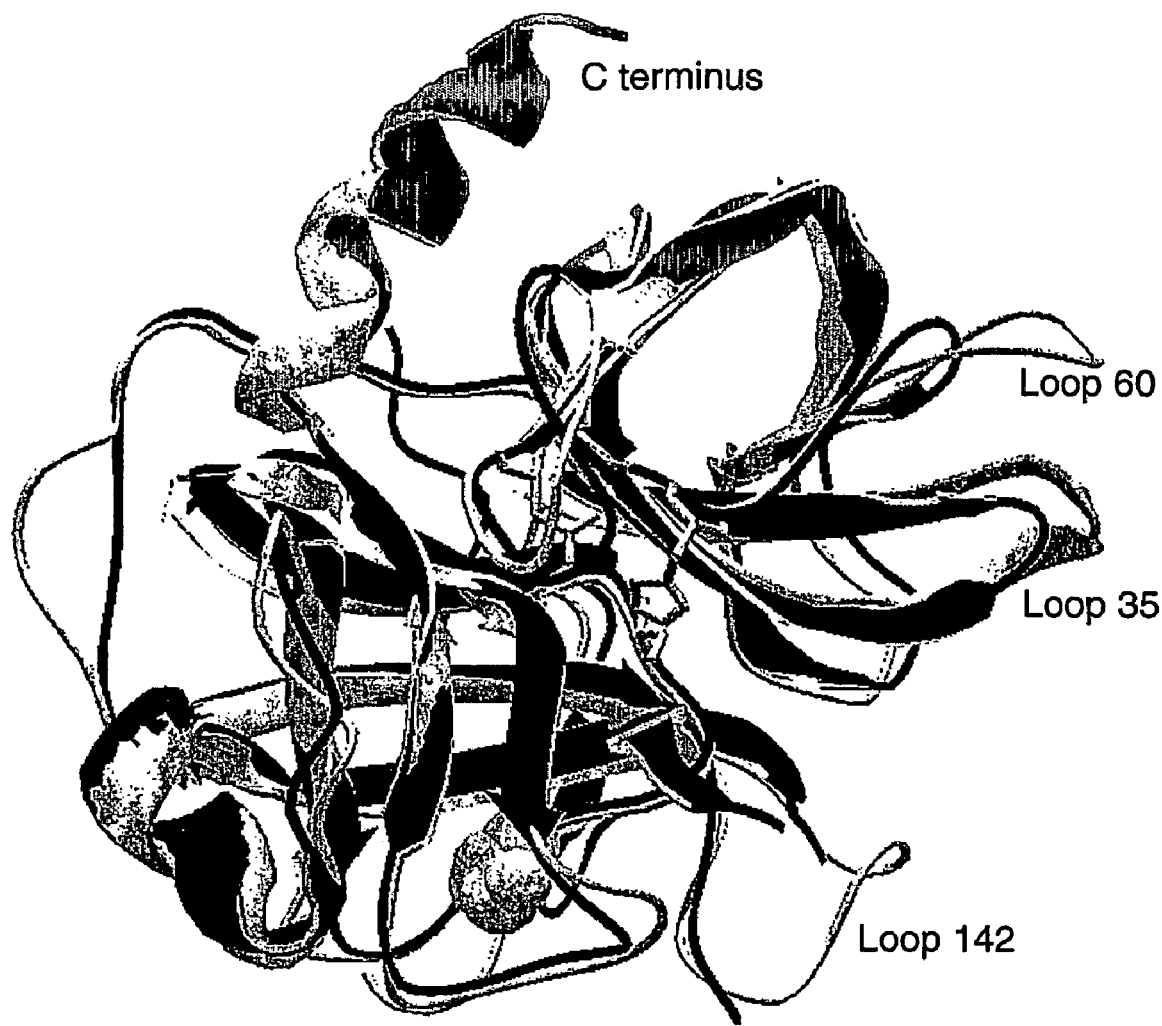
FIG. 16 is a diagrammatic representation showing several surface loops in the structural model of *H. punctigera* chymotrypsin HpCh2A are larger than the cognate loops in bovine chymotrypsin. The structural model of *H. punctigera* F2A chymotrypsin (grey) was superimposed onto the structure of alpha-chymotrypsin from *Bos taurus* (black). Surface loops 60, 35, and 142 that are implicated in substrate recognition are larger in the insect chymotrypsin model. The chymotrypsin substrate specificity residue, serine 189, positioned at the base of the primary substrate-binding pocket is viewed as a space filled representation of the van der Waals radius.

*Biol.* 298: 895-901, 2000 ) was required to help refine the orientation of these surface loops in the *Helicoverpa* chymotrypsin models. Two surface loops, 60 and 142 are considerably larger in the *H. punctigera* chymotrypsins (FIGS. 15, 16).

C1 was modeled in complex with NaPI-sensitive and NaPI-insensitive chymotrypsins to investigate what residues in the NaPI-insensitive chymotrypsin might be involved in the loss of inhibitor binding. The structure of the chymotrypsin inhibitor C1 was previously determined by $^1$H NMR (Nielson et al., 1994, supra) but has not been determined in a proteinase complex. Therefore the related proteinase inhibitor PCI-1 from *Solanum tuberosum* in complex with Proteinase B from *Streptomyces griseus* (Greenblatt et al., *J. Mol. Biol.* 205: 201, 1989) provided an appropriate basis guiding the alignment of the complexes. Energy minimization of the C1-chymotrypsin complexes revealed Arg192 (chymotrypsin numbering system) as the only likely candidate to cause such resistance from a possible 24 putative contact residues. The NaPI-insensitive chymotrypsin containing the Arg192 (Greer nomenclature, Greer, *Proteins* 7:317-34, 1990. FIG. 15) residue in complex with C1 could not be properly energy minimized due to steric contacts between Arg192 and C1 whereas the Gln192 residue in the Na-PI sensitive chymotrypsin in complex with C1 caused no such problems due to its much

TABLE 3

Effect of various proteinase inhibitors on the activity of the NaPI-insensitive chymotrypsins from *H. punctigera* and bovine chymotrypsin

| Inhibitor | Maximum concentration tested | | % Inhibition | | IC50 | |
|---|---|---|---|---|---|---|
| | Insensitive µM | BC µM | Insensitive | BC | Insensitive µM | BC µM |
| NaPI | 10 | 4 | 0% | 100% | >10 | 0.04 |
| Chymostatin | 0.05 | 0.1 | 100% | 100% | 0.004 | 0.004 |
| Pot I | 5 | 5 | 100% | 100% | 0.12 | 0.02 |
| Bowman Birk | 10 | 5 | 100% | 100% | 0.24 | 0.06 |
| Lima bean | >20 | 5 | 89% | 100% | 3 | 0.2 |
| SBTI | >20 | >20 | 82% | 94% | 33 | 13 |
| PMSF | 1000 | 2000 | 100% | 100% | 33 | 13 |
| Leupeptin | >4000 | >4000 | 96% | 52% | 140 | 2400 |

SBTI, soybean trypsin inhibitor; PMSF, phenylmethyl sulphonyl fluoride; Bowman Birk, soybean Bowman Birk inhibitor; lima bean, lima bean trypsin inhibitor (Sigma); Pot I, potato proteinase inhibitor Type I. Bovine chymotrypsin (BC).

Without limiting the mode of action of any of these compounds to any one activity, 3-D modeling is used to investigate the binding ability of PotI and the peptide encoded by the C1 domain of NaPI to both NaPI-insensitive and NaPI-sensitive insect chymotrypsins.

Figure 17:
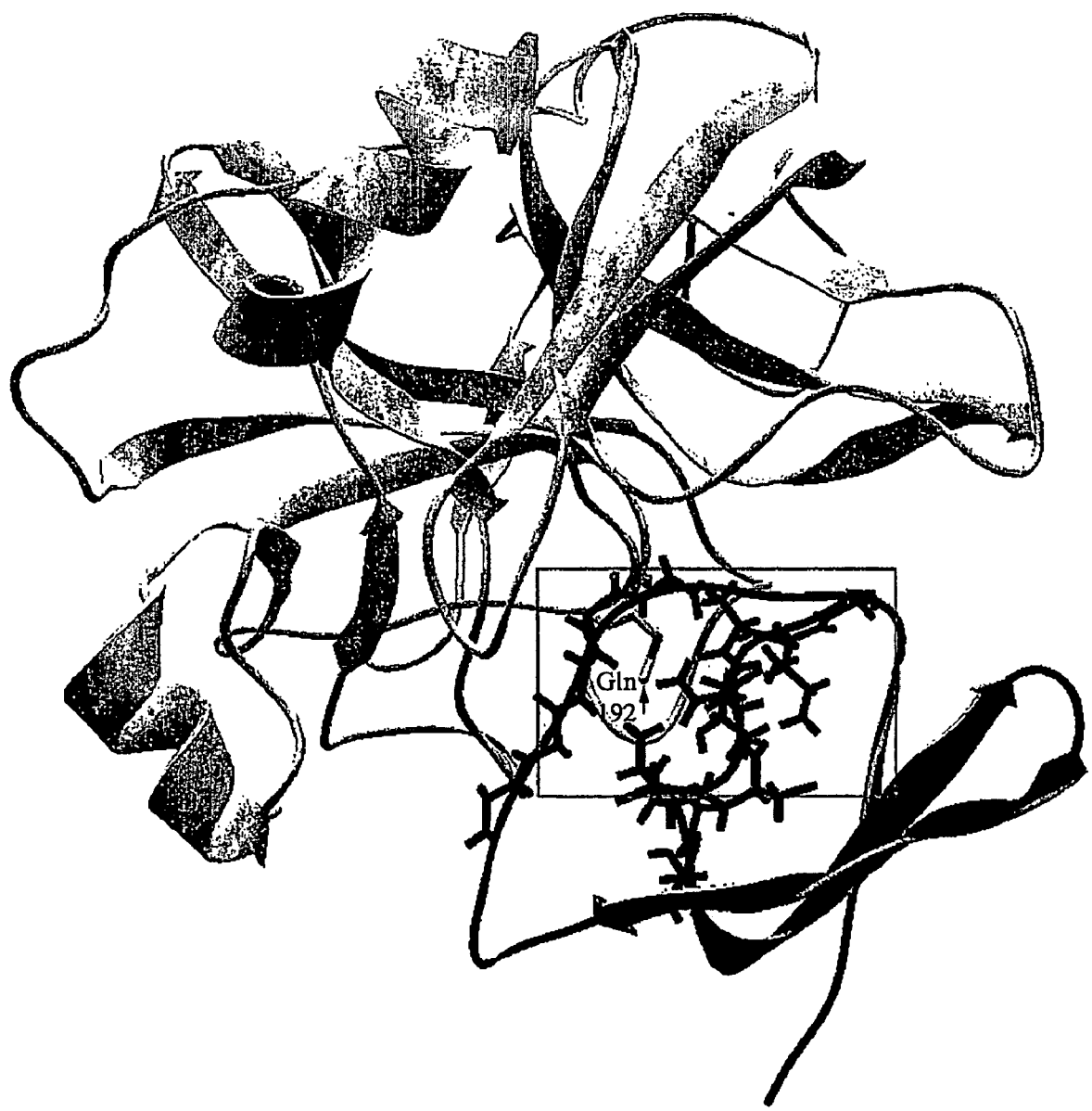
FIG. 17 is a representation showing glutamine 192 (Greer, 1990, supra nomenclature, FIG. 15) of the sensitive chymotrypsin HpCh2A appears easily accommodated when modeled in complex with C1. Structural model of the sensitive chymotrypsin HpCh2A (grey) in complex with the proteinase inhibitor C1 (black). The side chain of glutamine 192 is arrowed The residues of C1 in the vicinity of Gln 192 are represented in stick configuration (black).
Figure 18A:
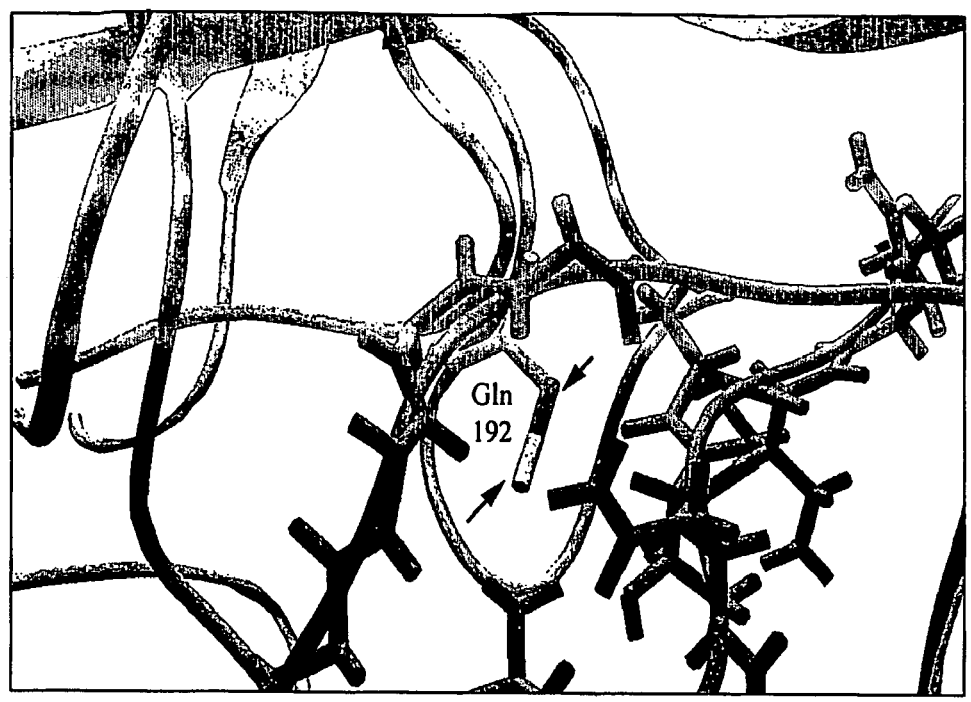
FIG. 18 is a diagrammatic representation showing comparison of the environment surrounding residue 192 of the sensitive and insensitive chymotrypsin complexed to C1.Enlarged view of the boxed area shown in FIG. 17. Arginine 192 of the insensitive chymotrypsin (B) appears to clash with residues of the C1 inhibitor, in contrast there is no apparent conflict with glutamine 192 of the sensitive chymotrypsin (A).
Figure 18B:
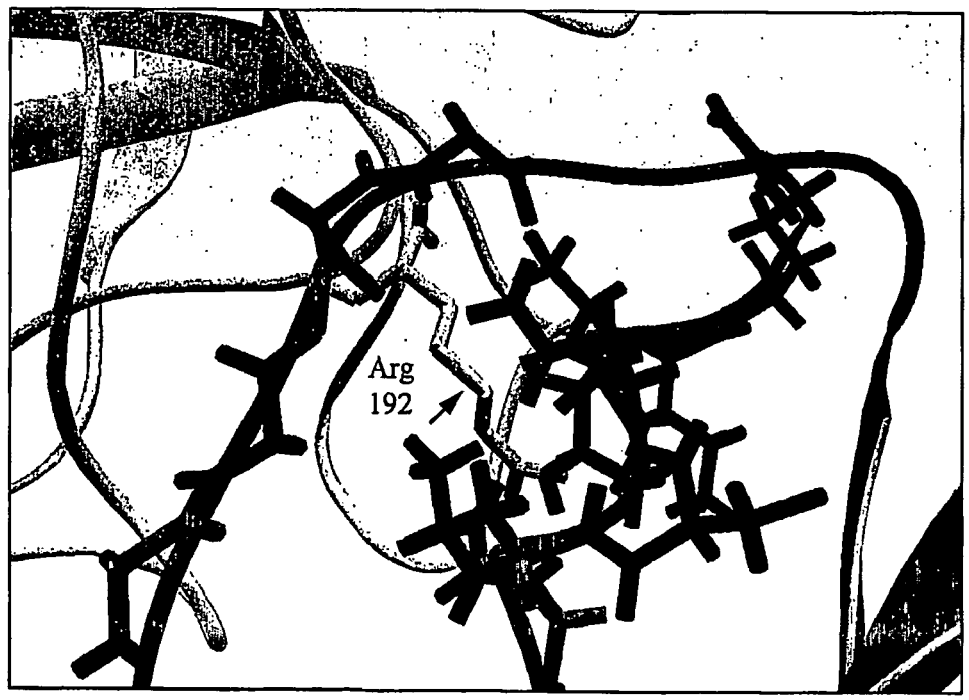
Figure 19A:
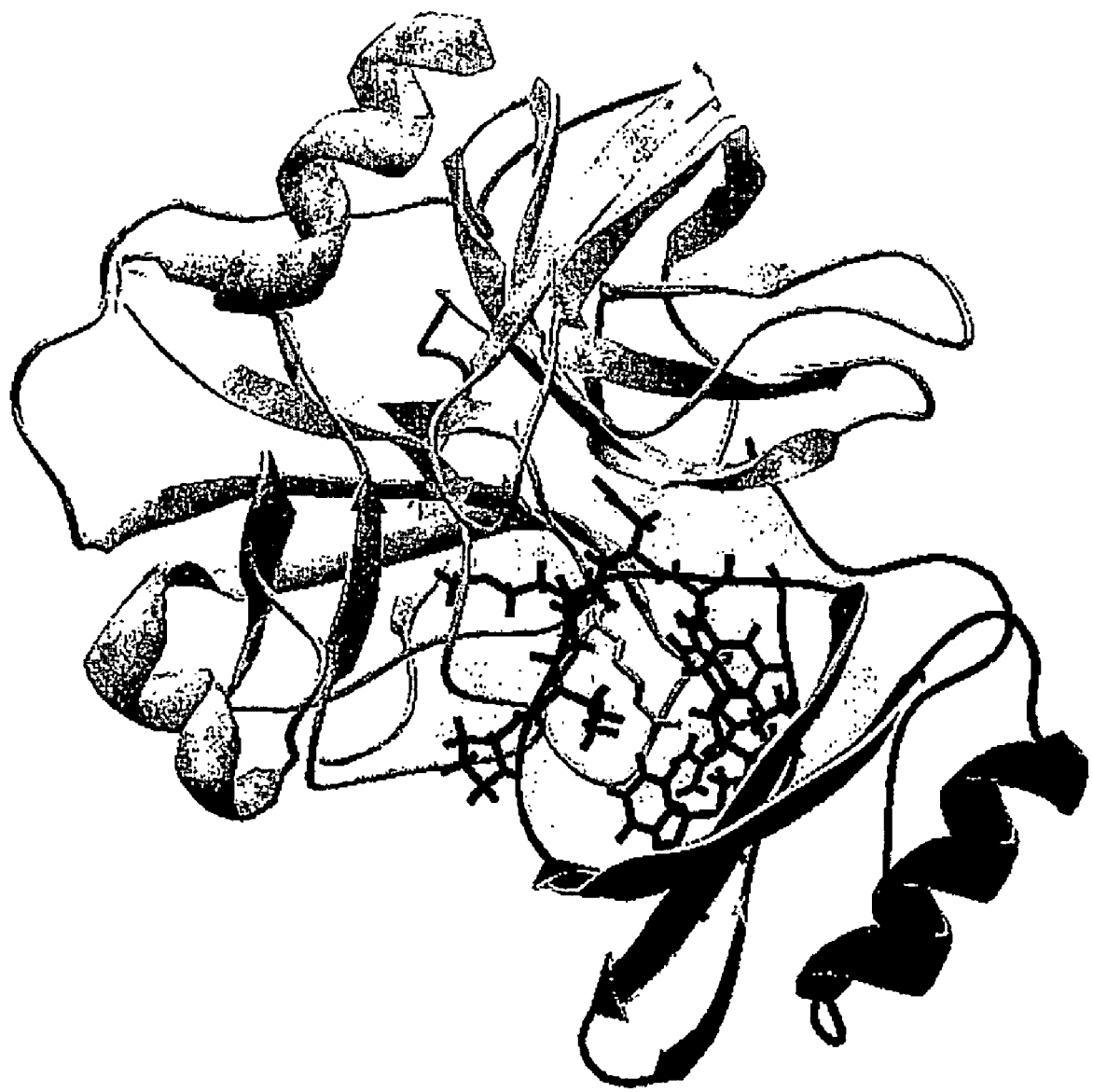
FIG. 19 is a diagrammatic representation showing the environment surrounding arginine 192 when the insensitive chymotrypsin is complexed to the Type 1 potato proteinase inhibitor (PotIB, FIG. 24). (A) Structural model of the insensitive chymotrypsin HpCh5 (grey) in complex with the potato type I proteinase inhibitor PotI (black). (B) Enlarged view of the region around Arg 192 (boxed area in B). The side chain of arginine 192 is labeled. The residues of PotI in the vicinity of Arg 192 are represented in stick configuration (black).
Figure 19B:

The deduced amino acid sequences from the cDNA clones HpF2A (NaPI-sensitive) and HpF5 (NaPI-insensitive) were modeled on the structures of the *Solenopsis invicta* (fire ant) and *Bos taurus* (cow) chymotrypsins obtained from the Research Collaboratory for Structural Bioinformatics (RCSB) Protein Data Bank. The *Helicoverpa* chymotrypsins are predicted to adopt similar structures to those reported for all the chymotrypsin structures available in the data bank. The modeled structures have the classic serine protease fold consisting of two, six-stranded anti-parallel beta barrels with the catalytic triad located between the two domains. Certain surface loops are cleaved in the mammalian chymotrypsins (loop 142), but remain intact within insect chymotrypsins. Therefore, the fire ant chymotrypsin structure (Botos et al., *J. Mol.* smaller size. FIG. 17 shows a close up view of the binding region surrounding Gln192 in the C1-HpF2A chymotrypsin complex. It is clear that Gln192 is not in conflict with any regions on the inhibitor molecule. However, comparison to the cognate Arg residue in the C1-HpCh5 chymotrypsin model demonstrates there is not enough space to accommodate this much larger residue (FIG. 18) making contact with Thr5 and Ala9 in C1. Furthermore, modeling the StPot1A inhibitor into HpCh5 revealed that the NaPI-insensitive chymotrypsin could accommodate the Arg192 residue consistent with the inhibition of this chymotrypsin by StPot1A (FIG. 19).

In summary, the NaPI-insensitive chymotrypsin from *Helicoverpa* species has an arginine in place of an asparagine or glutamine at position 192 that extends into the S1 binding pocket and appears to interfere with C1 binding. Furthermore, it is clear that this Arg residue does not interfere with PotI binding, consistent with the observation that PotI is a much more efficient inhibitor of insect chymotrypsins than the NaPI inhibitors. Large quantities of the PotI inhibitor were purified from potato tubers (FIG. 22) to evaluate the combined effect of NaPI and PotI on the growth of *H. armigera* larvae (FIG. 23). Bioassays confirmed that PotI significantly enhances the activity of the NaPI inhibitors. Caterpillars fed NAPI and PotI in combination (0.26 and 0.34% (w/v), respectively) were 34% the size of control larvae at the fifth instar stage of development whereas caterpillars feeding on NaPIs alone were about 84% the size of the controls.

Therefore, another aspect of the present invention provides a method for modulating activity of the HpCh5 or a homolog or variant thereof in an insect, said method comprising contacting the HpCh5 protein or its homolog or variant with an effective amount of an agent for a time and under conditions sufficient to decrease or increase HpCh5 activity.

Yet another aspect of the present invention provides a method for modulating expression of HpF5 or homolog or variant in an insect, said method comprising contacting HpF5 or its homolog or variant with an effective amount of an agent for a time and under conditions sufficient to decrease or increase HpF5 expression.

The preferred insects targeted in accordance with these and other aspects are species of *Helicoverpa* and other *Lepidopteran* species. In addition, plants to be protected include those sensitive to *H. armigera, H. punctigera, H. zea* and *H. virescens*. Such plants include the *H. armigera* sensitive plants such as cotton, sweet corn, tomato, tobacco, piniento, potato, sunflower, citrus, plums, sorghum, leeks, soybean, alfalfa, beans, pidgeon peas, chick peas, artichokes, curcurbits, lettuce, *Dianthus* (an ornamental plant), geraniums, cape gooseberry, maize, flax and linseed, alfalfa, lupins, broad beans, garden peas, peanuts, canola, snapdragons, cherry, sunflower, pot marigolds and *Helichrysum* (an ornamental plant)

Other plants contemplated herein include cereals (such as wheat, barley, oats, triticale, etc.), horticultural plants (e.g. apples, carrots, onions, etc.), ornamental plants (such as orchids, roses, petunias, etc.) and trees.

The present invention contemplates, therefore, methods of screening for compounds which inhibit or act as antagonists of HpCh5 activity or HpF5 gene expression. For example, one method involves contacting a candidate compound with HpCh5. The screening procedure includes assaying (i) for the presence of a complex between the compound and HpCh5, or (ii) an alteration in the expression levels of HpF5 cDNA or genomic DNA. One form of assay involves competitive binding assays. In such competitive binding assays, HpCh5 is typically labeled. Free HpCh5 is separated from any putative complex and the amount of free (i.e. uncomplexed) label is a measure of the binding of the agent being tested to bind to HpCh5. One may also measure the amount of bound, rather than free, HpCh5. It is also possible to label the compound rather than HpCh5 and to measure the amount of compound binding to target in the presence and in the absence of the compound being tested. Such compounds may inhibit HpCh5. A similar approach may be adopted for compounds which bind to and inhibit HpF5 or mRNA transcripts thereof.

Another technique for agent screening provides high throughput screening for compounds having suitable binding affinity to HpCh5 and is described in detail in Geysen (International Patent Publication No. WO 84/03564). Briefly stated, large numbers of different small peptide test compounds are synthesized on a solid substrate, such as plastic pins or some other surface. The peptide test compounds are reacted with HpCh5 and washed. Bound HpCh5 molecules are then detected by methods well known in the art. This method may be adapted for screening for non-peptide, chemical entities. This aspect, therefore, extends to combinatorial approaches including phage display to screen for HpCh5 antagonists.

Purified HpCh5 can be coated directly onto plates for use in the aforementioned agent screening techniques. However, non-neutralizing antibodies to HpCh5 may also be used to immobilize HpCh5 on the solid phase.

Live animals such as *H. armigera* and/or *H. punctigera* may also be used in feeding trials to find potential inhibitors.

The present invention also contemplates the use of competitive agent screening assays in which neutralizing antibodies capable of specifically binding HpCh5 compete with a test compound for binding to HpCh5 or fragments thereof. In this manner, the antibodies can be used to detect the presence of any peptide which shares one or more antigenic determinants of HpCh5.

Yet another useful source of analogs of compounds which are chemically modified may be used to induce feed-back inhibition of biochemical or genetic pathways for generating authentic HpCh5.

Analogs of HpCh5 contemplated herein include but are not limited to modification to side chains, incorporating of unnatural amino acids and/or their derivatives during peptide, polypeptide or protein synthesis and the use of crosslinkers and other methods which impose conformational constraints on HpCh5.

Examples of side chain modifications of HpCh5 contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH4.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 4.

TABLE 4

Codes for non-conventional amino acids

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-Nmethylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |

TABLE 4-continued

Codes for non-conventional amino acids

| Non-conventional amino acid | Code |
| --- | --- |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)car-bamylmethyl)glycine | Nnbhe |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogs by introducing covalent bonds such as forming an amide bond between the N and C termini, between two side chains or between a side chain and the N or C terminus.

Such analogs, especially if they retain activity or even the HpCL5 molecule itself may have indistinct applications such as in washing powder or as in a stain removal formulation.

Another aspect of the present invention contemplates any compound which binds or otherwise interacts with HpCh5 or its derivatives or variants or which induces feed-back inhibition of HpCh5 synthesis resulting in down-regulation of HpCh5 activity or levels.

The present invention is also useful for screening for other compounds which reduce expression of HpF5. A variety of agent screening techniques may be employed such as those described herein and in International Publication No. WO 97/02048.

A compound antagonist includes a variant of HpCh5 such as a variant comprising an analog amino acid residue as indicated above. In one embodiment, the target is the HpCh5 polypeptide. The term "polypeptide" refers to a polymer of amino acids and its equivalent and does not refer to a specific length of the product, thus, peptides, oligopeptides and proteins are included within the definition of a polypeptide. This term also does not exclude modifications of the polypeptide, for example, glycosylations, acetylations, phosphorylations and the like. Included within the definition are, for example, polypeptides containing one or more analogs of an amino acid (including, for example, unnatural amino acids such as those given in Table 4) or polypeptides with substituted linkages.

A substance identified as an antagonist of HpCh5 function or HpFS gene activity may be a peptide or non-peptide in nature. Non-peptide "small molecules" are often preferred for many agricultural or horticultural purposes due to their perceived stability.

There are several steps commonly taken in the design of a mimetic-type antagonist of HpChS from a compound. First, the particular parts of the compound that are critical and/or important in determining the target property are determined. In the case of a peptide, this can be done by systematically varying the amino acid residues in the peptide, e.g. by substituting each residue in turn. Alanine scans of peptides are commonly used to refine such peptide motifs. These parts or residues constituting the active region of the compound are known as its "agrichemicaphore".

Once the agrichemicaphore has been found, its structure is modeled according to its physical properties, e.g. stereochemistry, bonding, size and/or charge, using data from a range of sources, e.g. spectroscopic techniques, x-ray diffraction data and NMR. Computational analysis, similarity mapping (which models the charge and/or volume of a agrichemicaphore, rather than the bonding between atoms) and other techniques can be used in this modeling process.

In a variant of this approach, the three-dimensional structure of HpCh5 and a compound binding it. This can be especially useful where HpCh5 or its antagonist change conformation on binding, allowing the model to take account of this in the design of the mimetic. Modeling can be used to generate inhibitors which interact with the linear sequence or a three-dimensional configuration.

A template molecule is then selected onto which chemical groups which mimic the pharmacophore can be grafted. The template molecule and the chemical groups grafted onto it can conveniently be selected so that the agrichemicaphore is easy to synthesize and is likely to be agriculturally or horticulturally acceptable. Alternatively, where the agrichemicaphore is peptide-based, further stability can be achieved by cyclizing the peptide, increasing its rigidity. The agrichemicaphore or agrichemicaphores found by this approach can then be screened to see whether they have HpCh5 antagonistic property, or to what extent they exhibit it. Further optimization or modification can then be carried out to arrive at one or more final agents for testing.

Yet another aspect of the present invention provides a method for detecting an agent capable of binding or otherwise associating with a HpCh5 binding site or functional equivalent thereof said method involving the use of in-silico 3-D modeling to identify compounds that bind to HpCh5 and specifically, are not interfered with by Arginine 192.

The goal of rational HpCh5 antagonist design is to produce structural analogs of HpCh5 or of small molecules with which HpCh5 interacts (e.g. an antagonist or inhibitor) in order to fashion agents which are, for example, more inhibitory of HpCh5. See, e.g. Hodgson (*Bio/Technology* 9: 19-21, 1991). In one approach, one first determines the three-dimensional structure of HpCh5 by x-ray crystallography, by computer modeling or, most typically, by a combination of approaches. Useful information regarding the structure of a polypeptide may also be gained by modeling based on the structure of chymotrypsins. An example of rational drug design is the development of HIV protease inhibitors (Erickson et al., *Science* 249: 527-533, 1990). In addition, target molecules may be analyzed by an alanine scan (Wells, *Methods Enzymol.* 202: 2699-2705, 1991). In this technique, an amino acid residue is replaced by Ala and its effect on the peptide's activity is determined. Each of the amino acid residues of the peptide is analyzed in this manner to determine the important regions of the peptide.

In addition, compounds including antagonists may be directed to particular locations or regions or domains or HpCh5.

It is also possible to isolate a HpCh5-specific antibody and then to solve its crystal structure. In principle, this approach yields an agricore upon which subsequent agent design can be based. It is possible to bypass protein crystallography altogether by generating anti-idiotypic antibodies (anti-ids) to a functional antibody. As a mirror image of a mirror image, the binding site of the anti-ids is expected to be an analog of the original receptor. The anti-id could then be used to identify and isolate peptides from banks of chemically or biologically produced banks of peptides. Selected peptides would then act as the agrichemicaphore.

Figure 20A:
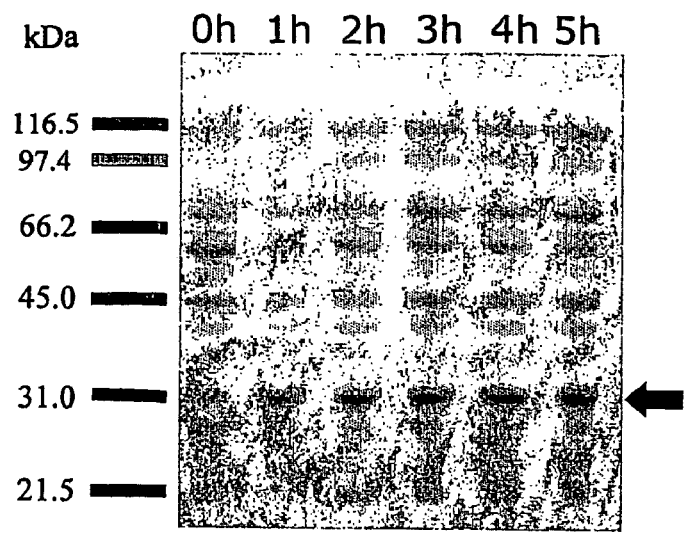
FIG. 20 is a photographic representation showing expression of the chymotrypsin clone HpF2B in *E. coli* cells for the production of a polyclonal antibody. (A) The separation of total cell lysates taken at time points 0-5 hr after induction of HpCh2B on a 12.5% (w/v) SDS-PAGE gel stained with Coomassie Blue. The lanes are marked by the number of hours after induction and the arrow indicates the position of the induced protein with the correct predicted molecular mass. (B) Panel 1: Bacterially expressed HpCh2B purified on Talon resin (BD Biosciences Clontech), separated on a 15% (w/v)
Figure 20B:
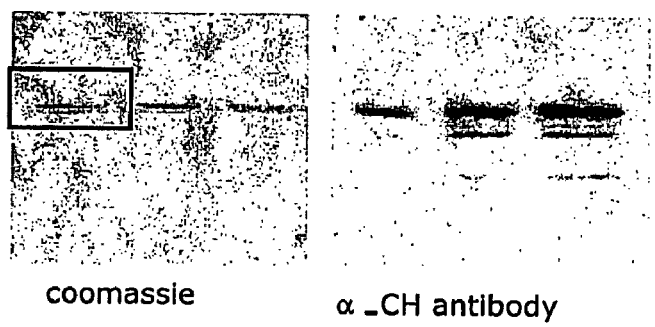
Figure 20C:
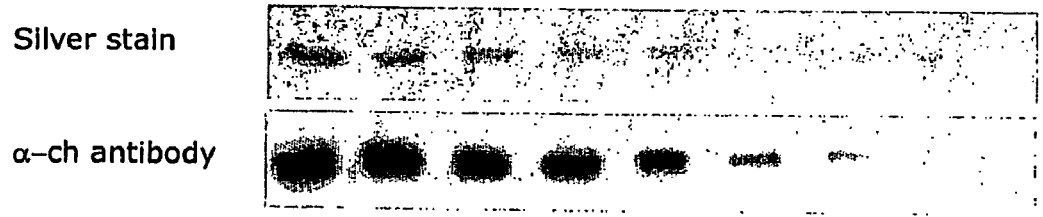

Chymotrypsin clone HpF2B is expressed in *E. coli* fused to a six histidine (6.H) tag at the C-terminus and is purified to homogeneity on Talon metal affinity resin (FIG. 20) for injection into a rabbit for production of polyclonal antibodies. N-terminal sequencing of the purified product confirmed the expression of the chymotrypsin HpCh2B. After the fourth boost with antigen, the serum is collected and tested on protein blots of bacterially expressed protein and unfractionated gut extracts. The antibody detected the full-length recombinant chymotrypsin at a dilution of 1 in 2500 as well as several break-down products. Unfractionated gut extract and a sample of protein bound to the C1 affinity column were also stained with the anti-HpCh2B antibody which detected the mature native form of the enzyme.

Purified 6H.HpCh2B is used to test the detection limit of anti-HpCh2B antibody by comparison of immunoblots to silver stained SDS-PAGE gels. The antibody detected 20 ng of bacterially expressed chymotrypsinogen and also recognized the mature form of the native chymotrypsin isolated from gut of *H. punctigera*.

The cDNA (HpF5) encoding the NaPI-insensitive chymotrypsin (HpCh5) is expressed in *E. coli* in a similar manner except the six-histidine tag is fused to the N-terminus of the expressed protein. The polyclonal antiserum that is raised against the bacterially expressed chymotrypsin HpCh2B did not cross react with bacterially expressed NAPI- insensitive chymotrypsin (HpCh5) on protein blots (FIG. 21). Likewise the antiserum raised against HpCh5 did not bind to HpCh2B. This indicates that these antisera can be used to specifically distinguish between and monitor levels of the NaPI-insensitive and sensitive chymotrypsins in unfractionated gut extracts Accordingly, still another aspect of the present invention is directed to antibodies to HpCh5 and HpCh2B including catalytic antibodies.

In another aspect of the present invention, a method is provided for the isolation of and separation of individual isoforms of chymotrypsin, said method consisting of:
  (i) affinity chromatography of insect gut extracts initially with benzamidine-sepharose to bind trypsins;
  (ii) further affinity chromatography of the unbound proteins using immobilized *N. alata* serine proteinase inhibitor C1 to bind all NAPI inhibitable chymotypsins; and
  (iii) affinity chromatography of the eluate from (ii) with immobilized PotI and PotII or chymostatin to bind the remainder. The putative NaPI-insensitive chymotrypsins are then eluted with 8 M urea.

The present invention extends to a genetic approach to down-regulating expression of an HpF5 or its homologs or variants. Such an approach uses nucleic acid molecules or molecules having a genetic component (e.g. RNAi) to induce pre- or post-transcriptional gene silencing.

The terms "nucleic acids", "nucleotide" and "polynucleotide" include RNA, cDNA, genomic DNA, synthetic forms and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog (such as the morpholine ring), internucleotide modifications such as uncharged linkages (e.g. methyl phosphonates, phosphotriesters, phosphoamidates, carbamates, etc.), charged linkages (e.g. phosphorothioates, phosphorodithioates, etc.), pendent moieties (e.g. polypeptides), intercalators (e.g. acridine, psoralen, etc.), chelators, alkylators and modified linkages (e.g. α-anomeric nucleic acids, etc.). Also included are synthetic molecules that mimic polynucleotides in their ability to bind to a designated sequence via hydrogen binding and other chemical interactions. Such molecules are known in the art and include, for example, those in which peptide linkages substitute for phosphate linkages in the backbone of the molecule.

Antisense polynucleotide sequences, for example, are useful in silencing transcripts of HpF5. Furthermore, polynucleotide vectors containing all or a portion of HpF5 gene locus may be placed under the control of a promoter in either the sense or antisense orientation and introduced into a cell. Expression of such a sense or antisense construct within a cell interferes with target transcription and/or translation. Furthermore, co-suppression (i.e. using sense-suppresion) and mechanisms to induce RNAi or siRNA may also be employed. Alternatively, antisense or sense molecules may be directly administered. In this latter embodiment, the antisense or sense molecules may be formulated in a composition and then administered by any number of means to target cells.

A variation on antisense and sense molecules involves the use of morpholinos, which are oligonucleotides composed of morpholine nucleotide derivatives and phosphorodiamidate linkages (for example, Summerton and Weller, *Antisense and Nucleic Acid Drug Development* 7: 187-195, 1997). Such compounds are injected into embryos and the effect of interference with mRNA is observed.

In one embodiment, the present invention employs compounds such as oligonucleotides and similar species for use in modulating the function or effect of nucleic acid molecules encoding HpCh5, i.e. the oligonucleotides induce transcriptional or post-transcriptional gene silencing. This is accomplished by providing oligonucleotides which specifically hybridize with one or more nucleic acid molecules encoding the inhibitor. The oligonucleotides may be provided directly to a cell or generated within the cell. As used herein, the terms "target nucleic acid" and "nucleic acid molecule encoding HpCh5" have been used for convenience to encompass DNA encoding the inhibitor, RNA (including pre-mRNA and mRNA or portions thereof) transcribed from such DNA, and also cDNA derived from such RNA. The hybridization of a compound of the subject invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired.

"Complementary" as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid. One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products.

In the context of the subject invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (D)NA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those herein described.

The open reading frame (ORF) or "coding region" which is known in the art to refer to the region between the translation initiation codon and the translation termination codon, is a region which may be effectively targeted. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns", which are excised from a transcript before it is translated. The remaining (and, therefore, translated) regions are known as "exons" and are spliced together to form a continuous mRNA sequence. Targeting splice sites, i.e. intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside.

For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may, therefore, fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

For topical delivery of antisense compounds, these oligonucleotides may contain modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

In an alternative embodiment, genetic constructs including DNA "vaccines" are used to generate antisense or sense molecules in plant cells. Furthermore, many of the preferred features described above are appropriate for sense nucleic acid molecules.

A further aspect of the present invention relates to a method for control of insect populations, said method comprising administering to insects an effective amount of an agent for a time and under conditions sufficient to inhibit the expression of HpF5 or sufficient to inhibit the activity of HpCh5, wherein said modulation results in reduction of the biological fitness of said insects.

In one preferred embodiment of the present invention, the agent is one that can bind to the primary substrate binding pocket of HpCh5, and not be interfered with by the arginine residue found at position 192.

Reference to a "reduction of biological fitness" should be understood to be changes in the insect including, but not limited to, changes in body mass and/or viability. Preferably, these changes are understood as reductions in both body mass and/or viability. A reduction in biological fitness, therefore, includes a reduction in their growth and development.

In yet another aspect the present invention provides a method for detecting an agent capable of modulating the function of HpCh5 or functional equivalent or derivative thereof, said method comprising administering to an insect containing said HpCh5 or functional equivalent or derivative thereof with a putative agent and detecting an altered activity phenotype associated with modulation of function of HpCh5 or its functional equivalent or derivative.

Reference to "administration" of the modulator to HpCh5 refers to delivery of the modulating agent in any convenient means. In the agricultural setting this is likely to include, but not be limited to:

(i) the delivery of the agent as the active ingredient in a spray or powder formulation; or (ii) the production of the agent either as a protein or the product of a metabolic pathway in a plant.

In a preferred embodiment of the invention, the administration of the agent is via the introduction of a nucleic acid encoding said agent into a plant for subsequent expression and production of the agent. Another preferred embodiment is the formulation of a spray or powder with said agent as the active ingredient.

"Introduction" of the agent is to be understood to cover all means known to those in the art of making genetic changes in a plant. These include, but are not limited to plant transformation methods such as particle bombardment, *Agrobacterium*-mediated transformation, electroporation and viral transfection; plant-breeding techniques and mutagenesis of native plant genes.

Accordingly, in the context of the present invention, nucleic acid molecules encoding an antisense or sense form of HpF5 or encoding an inhibitor of HpCh5 activity or HpF5 expression is operably linked to a promoter, generally in a vector or other suitable medium for introduction to a plant genome. Alternatively, an existing PI may be cloned and modified to render it active against HpCh5.

The present invention further provides a genetically modified plant comprising cells which are capable of producing an antagonist of HpCh5 or HpF5 gene expression. In one particularly useful example, cotton or other crop plants are engineered to produce PotI or a combination of PotI and NAPI. Reference herein to "PotI" and "NaPI" includes reference to derivatives, variants and homologs including modifications to one or more domains in PotI or NAPI.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5', or a structural gene region, the expression of which it regulates. Furthermore, the regulatory elements comprising a promoter are usually positioned within 2 kb of the start site of transcription of the gene.

In the present context, the term "promoter" is also used to describe a synthetic or fusion molecule, or derivative which confers, activates or enhances expression of a nucleic acid molecule in a cell.

Preferred promoters may contain additional copies of one or more specific regulatory elements, to further enhance expression of the sense molecule and/or to alter the spatial expression and/or temporal expression of said sense molecule. For example, regulatory elements which confer copper inducibility may be placed adjacent to a heterologous promoter sequence driving expression of a sense molecule, thereby conferring copper inducibility on the expression of said molecules.

Placing a nucleic acid molecule under the regulatory control of a promoter sequence means positioning the said molecule such that expression is controlled by the promoter sequence. Promoters are generally positioned 5' (upstream) to the genes that they control. In the construction of heterologous promoter/structural gene combinations, it is generally preferred to position the promoter at a distance from the gene transcription start site that is approximately the same as the distance between that promoter and the gene it controls in its natural setting, i.e. the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e. the genes from which it is derived. Again, as is known in the art, some variation in this distance can also occur.

The promoter may regulate the expression of HpF5 or its variant or homolog constitutively, or differentially with respect to cell, the tissue or organ in which expression occurs or, with respect to the developmental stage at which expression occurs, or in response to external stimuli such as physiological stresses, or pathogens, or metal ions, amongst others.

Preferably, the promoter is capable of regulating expression of a nucleic acid molecule in a plant cell, tissue or organ, at least during the period of time over which the target gene is expressed therein and more preferably also immediately preceding the commencement of detectable expression of the HpF5gene in said cell, tissue or organ.

Accordingly, strong constitutive promoters are particularly useful for the purposes of the present invention or promoters which may be induced by virus infection or the commencement of HpF5 gene expression.

Plant-operable promoters are particularly preferred for use in the construct of the present invention. Examples of suitable promoters include pCaMV 35S (Fang et al., *Plant Cell* 1: 141-150, 1989), PGEL1 (Hajdukiewicz et al., *Plant Mol. Biol.* 25: 989-994, 1994), class III chitinase (Samac and Shah, *Plant Cell* 3: 1063-1072, 1991), pin2 (Keil et al., *EMBO J* 8: 1323-1330, 1989), PEP carboxylase (Pathirana et al., *Plant J.* 12: 293-304, 1997; MAP kinase (Schoenbeck et al., *Molec. Plant-Microbe Interact,* 1999), MSV (Legavre et al., In: Vth International Congress of Plant Molecular Biology, Singapore, 1997), pltp (Hsu et al., *Plant Sci.* 143: 63-70, 1999), pmpi (Cordero et al., In: General Meeting of the International Program on Rice Biotechnology of the Rockefeller Foundation, Malacca, Malaysia, 1997) or glutamin synthase (Pujade-Renaud et al., *Plant Physiol. Biochem.* 35: 85-93, 1997).

In the present context the terms "in operable connection with" or "operably under the control" or similar shall be taken to indicate that expression of the nucleic acid molecule is under the control of the promoter sequence with which it is spatially connected; in a cell, tissue, organ or whole plant.

The construct preferably contains additional regulatory elements for efficient transcription, for example, a transcription termination sequence.

The term "terminator" refers to a DNA sequence at the end of a transcriptional unit which signals termination of transcription. Terminators are 3'-non-translated DNA sequences generally containing a polyadenylation signal, which facilitates the addition of polyadenylate sequences to the 3'-end of a primary transcript. Terminators active in plant cells are known and described in the literature. They may be isolated from bacteria, fungi, viruses, animals and/or plants or synthesized de novo.

As with promoter sequences, the terminator may be any terminator sequence which is operable in the cells, tissues or organs in which it is intended to be used.

Examples of terminators particularly suitable for use in the synthetic genes of the present invention include the SV40 polyadenylation signal, the HSV TK polyadenylation signal, the CYC1 terminator, ADH terminator, SPA terminator, nopaline synthase (NOS) gene terminator of *Agrobacterium tumefaciens,* the terminator of the cauliflower mosaic virus (CaMV) 35S gene, the zein gene terminator from *Zea mays,* the Rubisco small subunit gene (SSU) gene terminator sequences, subclover stunt virus (SCSV) gene sequence terminators, any rho-independent *E. coli* terminator, or the lacZ alpha terminator, amongst others.

In a particularly preferred embodiment, the terminator is the SV40 polyadenylation signal or the HSV TK polyadenylation signal which are operable in animal cells, tissues and organs, octopine synthase (OCS) or nopaline synthase (NOS) terminator active in plant cells, tissue or organs, or the lacZ alpha terminator which is active in prokaryotic cells.

Those skilled in the art will be aware of additional terminator sequences which may be suitable for use in performing the invention. Such sequences may readily be used without any undue experimentation.

Means for introducing (i.e. transfecting or transforming) cells with the constructs are well-known to those skilled in the art.

The constructs described supra are capable of being modified further, for example, by the inclusion of marker nucleotide sequences encoding a detectable marker enzyme or a functional analogue or derivative thereof, to facilitate detection of the synthetic gene in a cell, tissue or organ in which it is expressed. According to this embodiment, the marker nucleotide sequences will be present in a translatable format and be expressed.

Those skilled in the art will be aware of how to produce the constructs described herein and of the requirements for obtaining the expression thereof, when so desired, in a specific cell or cell-type under the conditions desired. In particular, it will be known to those skilled in the art that the genetic manipulations required to perform the present invention may require the propagation of a genetic construct described herein or a derivative thereof in a prokaryotic cell such as an *E. coli* cell or a plant cell or an animal cell.

The constructs of the present invention may be introduced to a suitable cell, tissue or organ without modification as linear DNA, optionally contained within a suitable carrier, such as a cell, virus particle or liposome, amongst others. To produce a genetic construct, a nucleic acid (e.g. HpF5) is inserted into a suitable vector or episome molecule, such as a bacteriophage vector, viral vector or a plasmid, cosmid or artificial chromosome vector which is capable of being maintained and/or replicated and/or expressed in the host cell, tissue or organ into which it is subsequently introduced.

Accordingly, a further aspect of the invention provides a genetic construct which at least comprises a genetic element as herein described and one or more origins of replication and/or selectable marker gene sequences.

Usually, an origin of replication or a selectable marker gene suitable for use in bacteria is physically-separated from those genetic sequences contained in the genetic construct which are intended to be expressed or transferred to a plant cell, or integrated into the genome of a plant cell.

As used herein, the term "selectable marker gene" includes any gene which confers a phenotype on a cell on which it is expressed to facilitate the identification and/or selection of cells which are transfected or transformed with a genetic construct of the invention or a derivative thereof.

Suitable selectable marker genes contemplated herein include the ampicillin-resistance gene ($Amp^r$), tetracycline-resistance gene ($Tc^r$), bacterial kanamycin-resistance gene ($Kan^r$), the zeocin resistance gene (Zeocin is a drug of the bleomycin family which is trade mark of InVitrogen Corporation), the A URI-C gene which confers resistance to the antibiotic aureobasidin A, phosphinothricin-resistance gene, neomycin phosphotransferase gen (nptII), hygromycin-resistance gene, β-glucuronidase (GUS) gene, chloramphenicol acetyltransferase (CAT) gene, green fluorescent protein-encoding gene or the luciferase gene, amongst others.

Preferably, the selectable marker gene is the nptII gene or $Kan^r$ gene or green fluorescent protein (GFP)-encoding gene.

Those skilled in the art will be aware of other selectable marker genes useful in the performance of the present invention and the subject invention is not limited by the nature of the selectable marker gene.

The present invention extends to all genetic constructs essentially as described herein, which include further genetic sequences intended for the maintenance and/or replication of said genetic construct in prokaryotes or eukaryotes and/or the integration of said genetic construct or a part thereof into the genome of a eukaryotic cell or organism.

Standard methods described supra may be used to introduce the constructs into the cell, tissue or organ, for example, liposome-mediated transfection or transformation, transformation of cells with attenuated virus particles or bacterial cells, cell mating, transformation or transfection procedures known to those skilled in the art.

Additional means for introducing recombinant DNA into plant tissue or cells include, but are not limited to, transformation using $CaCl_2$ and variations thereof, direct DNA uptake into protoplasts, PEG-mediated uptake to protoplasts, microparticle bombardment, electroporation, microinjection of DNA, microparticle bombardment of tissue explant or cells, vacuum-infiltration of tissue with nucleic acid, or in the case of plants, T-DNA-mediated transfer from *Agrobacterium* to the plant tissue.

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 1 to 5 μm gold spheres. The DNA construct may be deposited on the microparticle by any suitable technique, such as by precipitation.

In a further embodiment of the present invention, the genetic constructs described herein are adapted for integration into the genome of a cell in which it is expressed. Those skilled in the art will be aware that, in order to achieve integration of a genetic sequence or genetic construct into the genome of a host cell, certain additional genetic sequences may be required. In the case of plants, left and right border sequences from the T-DNA of the *Agrobacterium tumefaciens* Ti plasmid will generally be required.

The present invention further extends to an isolated cell, tissue or organ comprising the constructs or parts thereof. The present invention extends further to regenerated tissues, organs and whole organisms derived from said cells, tissues and organs and to propagules and progeny thereof as well as seeds and other reproductive material.

For example, plants may be regenerated from transformed plant cells or tissues or organs on hormone-containing media and the regenerated plants may take a variety of forms, such as chimeras of transformed cells and non-transformed cells; clonal transformants (e.g. all cells transformed to contain the expression cassette); grafts of transformed and untransformed tissue (e.g. a transformed root stock grafted to an untransformed scion in citrus species). Transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques.

Plants contemplated herein include cotton, sweet corn, tomato, tobacco, piniento, potato, sunflower, citrus, plums, sorghum, leeks, soybean, alfalfa, beans, pidgeon peas, chick peas, artichokes, curcurbits, lettuce, Dianthus (an ornamental plant), geraniums, cape gooseberry, maize, flax and linseed, lupins, broad beans, garden peas, peanuts, canola, snapdragons, cherry, sunflower, pot marigolds, Helichrysum (an ornamental plant), wheat, barley, oats, triticale, carrots, onions, orchids, roses and petunias Another aspect of the present invention relates to the insensitive chymotrypsin as a selectable marker for the transformation of insects. At present, methods for the germ-line transformation of insects involves injection of insect embryos with a genetic construct comprising a transposable element, the gene of interest and a selectable marker. Somatic transformation of insects can also be achieved using viral vectors that include the gene of interest and a selectable marker (Peloquin et al., *J. Cot. Sci.* 5: 114-120, 2001). Presently, most insect transformation is done using white-eye mutants of the insect, to allow the detection of the commonly used selectable markers. Typically, selectable markers are genes that complement the white-eye mutation or Enhanced Green Fluorescent Protein (EGFP). In *Drosophila,* the white eye mutation is caused by mutant alleles such as the $\overline{\omega}^{1118}$ allele. These individuals can be returned to normal (red) eye pigmentation via the introduction of an allele conferring normal eye pigmentation such as white (Lidholn et al., *Genetics* 134: 859-868, 1993) or miniwhite (Lozovskaya et al., *Genetics* 142: 173-177, 1996). The reversion of $\overline{\omega}^{1118}$ mutants to normal eye pigmentation acts as the marker for introduction of the vector. In a similar way, EGFP has been used to indicate the presence of a vector. Again, insects with non-pigmented eyes are used, and EGFP expression is detected in the eyes of these insects (Hediger et al., *Insect Mol. Biol.* 10: 113-119, 2001).

The selectable markers commonly used in the art require dissection of the insects to examine the eyes for either pigmentation or EGFP fluorescence, which is time consuming and requires destructive sampling of the insects. The present invention provides a means for the selection of transformed individuals without the need for insect dissection or inspection of individual insects. This would allow the recovery of live transformants and provides a non-laborious means of screening large numbers of putative transformants at one time. In addition, the present invention provides a means for the selection of transformants that does not rely on the availability of white-eye mutants.

The present invention contemplates the use of HpF5 or a derivative, homolog or analog thereof encoding a NaPI-insensitive chymotrypsin, as a selectable marker in an insect transformation vector. This vector, comprising HpF5, would have utility for the selection of transformants for any insect that is susceptible to the C1 serine proteinase inhibitor of *N. alata*. The contemplated insects may be naturally resistant to C1, or may be NaPI-susceptible mutants or genetically modified NaPI susceptible strains of naturally NaPI-resistant insects. In a particularly preferred embodiment of the invention the insect host of the said vector would be Lepidopteran. HpF5 or a derivative, homolog or analog thereof encoding an NaPI-insensitive chymotrypsin could be incorporated into any insect transformation vector using common molecular biology techniques known to those in the art. Upon transformation the insect would transcribe HpF5 and produce HpCh5, the NaPI-insensitive chymotrypsin. Transformed individuals could then be selected by incorporation of the C1 proteinase inhibitor of *N. alata* into the diet of the insects. In this case individuals that did not carry the insensitive chymotrypsin encoded by HpF5 in the vector would die, and those that did carry the vector encoding HpF5 would be insensitive to C1.

Accordingly the present invention provides insect transformation vectors including baculovirus vectors comprising HpF5 or a derivative, homolog or analog thereof, as a selectable marker. The vector may be used for any purpose in the insect. Non-limiting examples include: gene cloning, gene expression and gene knockouts. Specific examples of insect transformation vectors into which HpF5 could be incorporated as a selectable marker include, but are not limited to: those that utilize the piggyBac mobilizable element (Hediger et al., 2001, supra); P-element based vectors (Cripps et al., *J. Cell Biol.* 126: 689-699, 1994); hobo element based vectors (Lozovskaya et al., 1996, supra); mariner element based vectors (Lidholm et al., 1993, supra); and viral vectors such as pTE/3'2J (Peloquin et al., 2001, supra).

The present invention is further described by the following non-limiting Examples.

EXAMPLE 1

Effect of Ingestion of the *N. alata* Proteinase Inhibitors on Growth and Development of *Helicoverpa* species The effect of the *N. alata* PIs is examined on the digestive enzymes and the growth and development of *Helicoverpa punctigera* and *Helicoverpa armigera* larvae (Heath et al., *J. Insect Physiol.* 43: 833-842, 1997). The PIs suppressed total gut protease activity by 73% in an in vitro assay using $^{14}$C-casein as substrate. When incorporated into an artificial diet the PIs retarded the growth and development of both *H. punctigera* (Heath et al., 1997, supra) (FIGS. 2A and 2B) and *H. armigera*. Similar results are obtained when larvae from both species were fed on transgenic tobacco (*N. tabacum*) expressing the *N. alata* PIs at levels of 0.2% -0.5% soluble protein (Heath et al., 1997, supra).

Ingestion of NaPIs (C1, C2 and T1-T4) changes the relative activity of the trypsins and chymotrypsins in the gut and faeces of *H. punctigera* larvae. Trypsin activity in the gut and the faeces is substantially lowered or abolished after exposure to NaPIs, whereas chymotrypsin activity is often unaffected or enhanced (FIGS. 2C and 2D). The lack of trypsin activity in the faeces of the NaPI fed larvae was not due to decreased production of trypsin. Indeed protein blots were used to demonstrate that these insects had overproduced trypsin in response to the PIs, but it had been totally inactivated (FIG. 2E).

Interestingly, the chymotrypsin produced after ingestion of NaPIs was not inhibitable by the NaPIs, whereas some of the chymotrypsin produced by control insects (not exposed to NaPIs) was inhibitable (FIG. 2F). In control insects the degree of inhibition varied between individuals, and ranged from about 75% to no inhibition at all. This suggested that *Helicoverpa* larvae produce different classes of chymotrypsins; some that are inhibitable by the NaPIs (PI-sensitive) and some that are not inhibitable (PI-insensitive). Thus, it appears ingestion of NaPIs inhibits the trypsin activity in the gut of *Helicoverpa* larvae, but larvae may not be severely impacted if they produce NaPI-insensitive chymotrypsins. In a subsequent experiment, the gut contents were removed from *H. punctigera* larvae that had been raised on a haricot bean diet without added proteinase inhibitors. The gut chymotrypsin activity was inhibited about 80% by the NaPI inhibitors (C1, C2, T1-T4) and 70% by C1 alone (FIG. 3). The Bowman Birk and trypsin inhibitors from Soybean and the lima bean trypsin inhibitor also failed to abolish all the chymotrysin activity, whereas activity was totally inhibited by the potato PotI inhibitor and chymostatin. Using this information a series of affinity columns were prepared for identification and purification of the NaPI-insensitive and -sensitive chymotrypsins from the gut of *H. punctigera* larvae.

Bioassays with *Helicoverpa* larvae on Artificial Diets

Haricot Bean Diet

*Helicoverpa* punctigera larvae were raised on artificial diets based on Haricot beans (Teakle et al., *Journal of Invertebrate Pathology* 46: 166-173, 1985). One liter of diet was composed of 58.5 g Haricot beans, 14 g agar, 700 ml water, 35 g Tortula yeast, 50 g wheatgerm, 3.5 g ascorbic acid, 1.1 g sorbic acid, 2.2 g p-hydroxybenzoic acid methyl ester, 0.2 g ampicillin, 0.2 g streptomycin, 16 mg prochloraz. The beans were soaked overnight in water, drained and homogenized to a fine paste. Wheatgerm, yeast and 300 ml of water were added. The agar was dissolved in 400 mL of boiling water and added to the mixture. The mixture was cooled to 50° C. before the addition of the remaining ingredients. The blended diet was poured into trays and after setting was used immediately or stored at −20° C. for no longer than two weeks. The test diet was supplemented with the NAPI (0.26% (w/v)) and the control diet had an equivalent amount of casein. Twenty newly emerged neonates were added to each diet and mortality was recorded every two days. Weight gain was recorded at the sixth day and then every second day thereafter. The larvae were reared in 1.5 ml eppendorf microfuge tubes (one larva/tube) until day eight when they were transferred to individual plastic containers with lids (SOLO [trademark] plastic portion cups, 28 mL). Larvae were fed small amounts of diet (40 mg) initially that was replaced as required to provide a continuous supply. The larvae were kept in a temperature controlled room at 25±1° C., 16:8 (L:D).

Cotton Leaf Diet

Cotton leaf artificial diet was prepared from fresh young leaves from cotton plants (cultivar Coker 315) which were grown in an insect-free and insecticide-free temperature controlled cabinet at 26° C. (±2° C.) with a light regime of 16:8 (L:D). Following picking, the leaves were immediately frozen in liquid nitrogen and freeze dried. After drying, the leaves were ground to a fine powder in a mortar and pestle. The cotton leaf artificial diet was prepared in the same manner as haricot bean artificial diet using a recipe modified from potato leaf artificial diet (Gatehouse et al., *J. Insect Physiol.* 45 (6), 545-558, 1999). One hundred grams of cotton leaf artificial diet contained 3 g of cotton leaf powder, 0.08 mL linseed oil, 2 g yeast, 0.016 mL wheatgerm oil, 2.4 g wheat germ, 0.028 g ampicillin, 3.2 g ascorbic acid, 0.028 g streptomycin, 0.08 g sorbic acid, 3.2 g agar, 0.16 g paraben (mould inhibitor) plus NaPI or casein to required % ((w/v)).

Preparation of Individual Gut and Frass Extracts

All work was performed at 4° C. Each gut was dissected from the larva and placed in a 1.5 mL microfuge tube containing 500 μL of ice-cold 10 mM Tris-HCl, pH 8. Gut and contents were homogenized using a micropestle (Eppendorf). Insoluble material was removed by centrifugation at 13,000 g for 4 min and the supernatant was stored at −80° C. Frass extracts were prepared in the same manner using 200 mg frass/mL buffer. Total protein concentration was determined using the Bradford method (Bradford, *Anal Biochem* 72: 248-254, 1976) with reagents from Bio-Rad and BSA as a standard.

Trypsin and Chymotrypsin Activity

Gut proteinase activity was determined at pH 10 in 50 mM 3-(cyclohexylamino)-1-propanesulfonic acid (CAPS buffer) using the chromogenic substrate N-benzoyl-DL-arginine-p-nitroanilide (BApNA) for trypsin and N-succinyl-L-alanine-alanine-proline-phenylalanine-p-nitroanilide ($SA_2PFpNA$) for chymotrypsin activity. Substrates were freshly prepared as 1 mM solutions in 10% ((w/v)) N,N-dimethylformamide (DMF), 50 mM CAPS buffer, pH 10. The assays were performed in duplicate or triplicate following the method of Heath et al, Eur.J.Biochem.230 (1): 250-257. Blanks, without enzyme, were used to account for any spontaneous breakdown of substrates. The release of p-nitroanilide was recorded at 405 nm after 30 min at 30° C. on a SpectraMax 250 microtitre plate reader (Molecular Devices).

Inhibition of Trypsin and Chymotrypsin Activity by NAPI

Trypsin and chymotrypsin inhibition assays were conducted using the standard trypsin and chymotrypsin assays described above except samples were pre-incubated with T1 or C1 inhibitor (80 nM) for 30 min at 30° C. prior to the addition of substrate to initiate the reaction. NAPI monomers T1 and C1 were HPLC purified as described by Heath et al., 1999, supra.

Chymotrypsin Assays in the Presence and Absence of Proteinase Inhibitors

Preparation of Gut Extracts

Fourth-instar larvae were killed using ethyl-acetate prior the removal of individual gut which were then homogenized in a mortar and pestle in an equal amount [(w/v)] of 50 mM Tris-HCl, pH 8.0 containing 100 μM benzamidine. Insoluble material was removed by centrifugation at 20,000 rpm for 15 min at 4° C. and total protein concentration determined using the Bradford method (Bradford, *Anal Biochem* 72: 248-254, 1976) with reagents from BioRad and BSA as a standard.

Assays

Unfractionated gut extract containing approximately 1 μg of buffer soluble protein was added to 10 μL CAPS buffer (0.5 M, 3-[cyclohexylamino]-1-propane-sulfonic acid, pH 10) and made to a final volume of 100 μL in individual wells of a 96 well microtiter plate. Proteinase inhibitors were added over a range of concentrations and incubated for 15 min at 25° C. Bovine chymotrypsin (100 ng) was used as a positive control, both for activity and inhibition. The chromogenic artificial substrate SAAPFpNA (N-Succinyl-L-alanyl-L-alanyl-L-prolyl-L-phenylalanine 4-nitroanilide) was then added to a final concentration of 1 mM and hydrolysis of the substrate was measured at 405 nm using the SpectraMax 250 microtiter plate reader (Molecular Devices).

Proteinase Inhibitors

Lima bean trypsin inhibitor (LBTI), soybean trypsin inhibitor (SBTI), soybean Bowman-Birk inhibitor (SBBI) and chymostatin were all purchased from Sigma-Aldrich Pty.Ltd. Potato Inhibitor I was purchased from Calbiochem-Novabiochem or purified from potato tubers (Example 6). A crude mixture of Potato inhibitor I and II was also obtained from potatoes. *N. alata* proteinase inhibitors (NaPIs) were purified as described by Atkinson et al., 1993, supra and Heath et al., 1995, supra. The chymotrypsin inhibitor C1 was purified from bacterial expression cultures. The purity of the inhibitors was assessed by SDS-PAGE and silver staining.

EXAMPLE 2

Isolation of NAPI Sensitive and Insensitive Chymotrypsins from *H. punctigera* gut Most published work on *Helicoverpa* chymotrypsins has focused on cDNA clones or the measurement of enzyme activity in unfractionated gut extracts. There are few reports on purification of chymotrypsins from *Helicoverpa* or other lepidopteran species. Johnston and coworkers (1995, supra) described partial purification of chymotrypsins from *H.armigera* that employed ion exchange techniques. Peterson and coworkers (*Insect Biochem. Mol. Biol.* 25: 765-774, 1995) purified a chymotrysin from the midgut of the lepidopteran *Manduca sexta* by affinity chromatography on tryptophan methyl ester and Valiatis et al., *Insect Biochemistry and Molecular Biology* 29: 405-415, 1999 used immobilized potato proteinase inhibitor I (PotI) to isolate a chymotrypsin from the Western Spruce budworm. No one has described a procedure that separates individual chymotrypsin isozymes from one another and there is no description of the isolation of two chymotrypsins from a single species where one isozyme is inhibitable by a certain proteinase inhibitor while another is not inhibitable.

Preparation of Pure Enzymes and N-Terminal Sequencing

Figure 1:
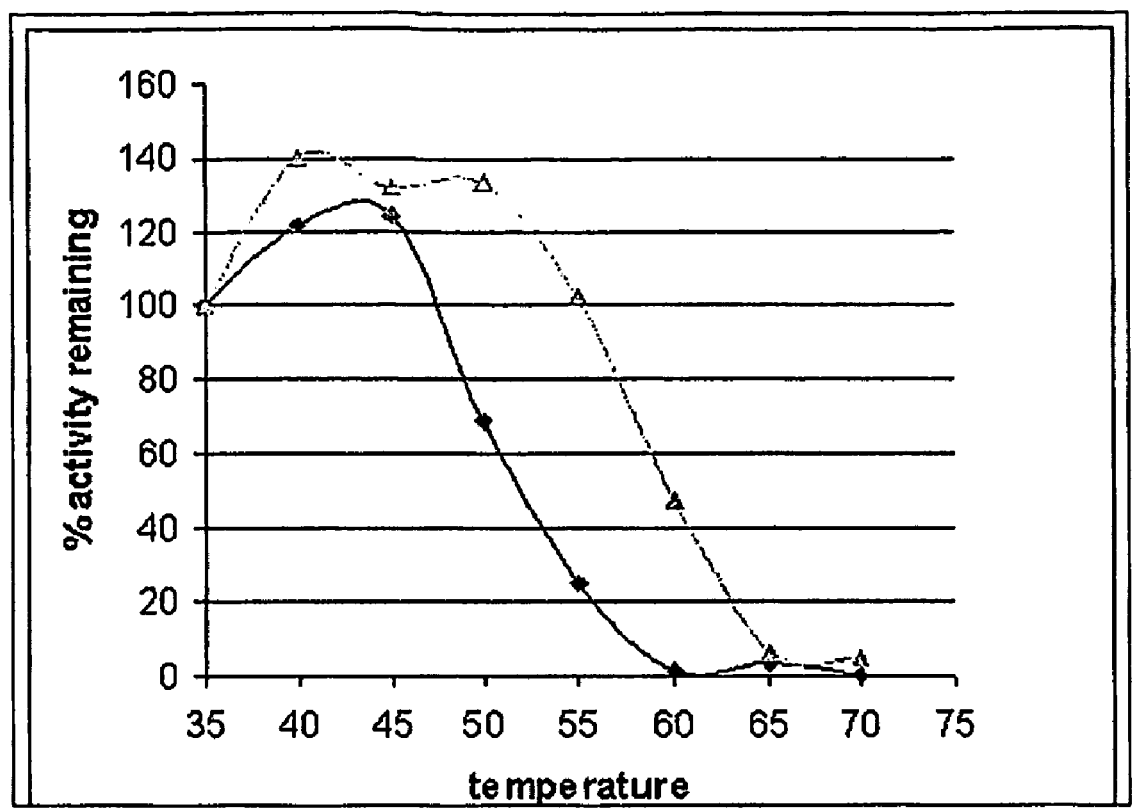
FIG. 1 is a graphical representation showing temperature stability of baculovirus expressed *H. punctigera* chymotrypsin. Bovine chymotrypsin (♦) and HpF5 (▲) in 50 mM Na acetate were compared by incubating 100 μL aliquots at 5° C. intervals between 40° C. and 70° C. After chilling the heated samples on ice, duplicate activity assays were performed by incubating 10 μL of be or 50 μL of HpF5 with substrate at 30° C. Residual activity was presented as a percentage of the activity of the untreated control.
Figure 2B:
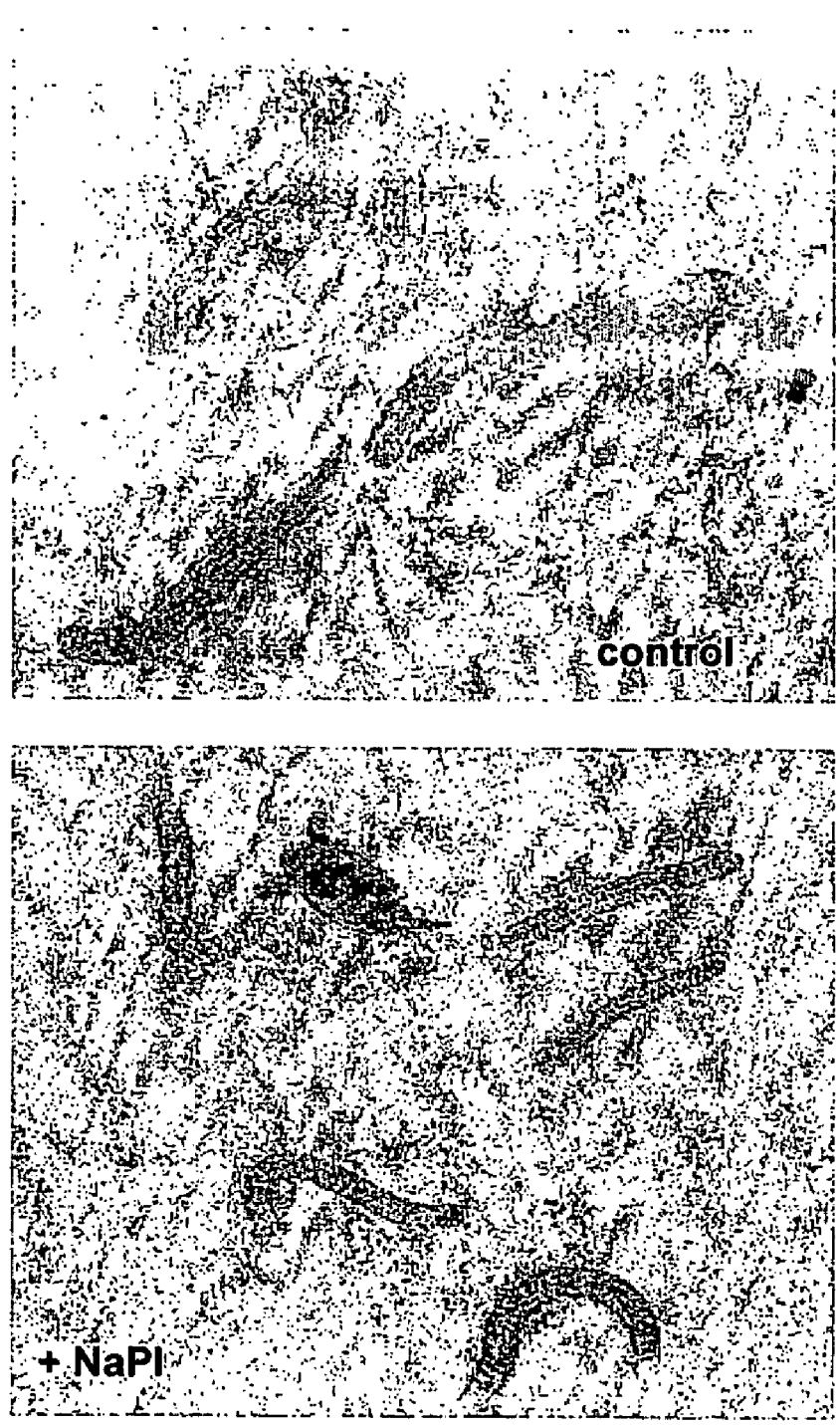
FIG. 2 is a graphical representation showing growth of *H. punctigera* larvae fed on either low protein haricot bean artificial diet or cotton leaf artificial diet, in the presence or absence of 0.26% (w/v) NaPIs. Weight gain (mg) was monitored for 21 days. Larvae grew at a similar rate on both artificial diets and growth was retarded in the presence of NaPIs. (A) Growth of larvae. (B) Relative size of larvae at 21 days after feeding on cotton artificial diet, in the presence or absence of 0.26% NaPIs. Only five of the 20 larvae fed on NaPI survived and all five weighed less than control larvae after 21 days. (C) The effect of NaPIs on gut trypsin and chymotrypsin activity. When each *H. punctigera* larva reached the late fourth/early fifth instar stage of development, the gut was removed and gut extract prepared prior to assays for trypsin and chymotrypsin activity. Extracts from individual larvae fed on control cotton-leaf artificial diet (CC) are indicated in grey and larvae fed on the same diet containing 0.26% ((w/v)) NaPI (NC) are indicated in black. Only four test larvae survived to fifth instar, whereas most control larvae survived. All assays were performed in duplicate. Trypsin activity was determined using BApNA substrate and chymotrypsin activity with SAAPFpNA substrate. Units of activity are expressed as change in absorbance at 405 nm/min/mg gut extract protein (±standard deviation). Trypsin activity was almost abolished, relative to controls, in extracts from NaPI-fed larvae, while chymotrypsin activity was low in two of the four NaPI-fed larvae. (D) The effect of NaPIs on trypsin and chymotrypsin activity in the frass. Frass was collected from each larva fed on the cotton leaf artificial diet and faecal extracts were prepared. Trypsin and chymotrypsin activity in extracts from larvae fed on the control diet (CC) are indicated in grey and larvae fed on the same diet containing 0.26% ((w/v)) NaPI (NC) are indicated in black. Note that frass of larvae CC16 and NC13 were included in this analysis but excluded from FIG. 2C because the gut were damaged during preparation of extracts. All assays were performed in duplicate. Trypsin activity was determined using BApNA substrate and chymotrypsin activity with SAAPFpNA substrate. Units of activity are expressed as change in absorbance at 405 nm/min/mg faecal extract protein (±standard deviation). Negligible trypsin activity was evident in extracts from NaPI-fed larvae, while chymotrypsin activity was elevated, relative to controls. (E) Levels of trypsin in the frass of control and NaPI fed larvae. Frass extracts were analysed on 15% ((w/v)) SDS-PAGE and transferred to nitrocellulose. The nitrocellulose filter was probed with rabbit anti-HpTRY1 serum (1 in 2000 dilution) as the primary antibody, followed by the secondary antibody, donkey anti-rabbit IgG-horse radish peroxidase conjugate (1 in 2000 dilution). Immuno-reactive proteins were visualized using Enhanced Chemiluminescence (ECL) reagents and HyperfilmECL X-ray film. The trypsin in the frass of larvae that consumed NaPIs (NC) was significantly increased relative to controls (upper panel) but inactive (lower panel), presumably because it was in complex with the NaPIs. In comparison, trypsin was active in the frass of the control larvae (CC) even though the amount present was below the detection level of the antibody. (F) Production of NaPI-insensitive proteases in the gut of NAPI fed larvae. The gut extracts of the larvae were subjected to inhibition assays to identity NaPI-insensitive trypsins and chymotrypsins. Each extract was pre-incubated for 30 min at 30° C. in the presence or absence of 80 nM NaPI inhibitor (T1 monomer for trypsin assays and C1 monomer for chymotrypsin assays), prior to the addition of substrate to initiate the reaction. Results from extracts assayed without inhibitor are indicated in grey(control larvae) and black (NaPI-fed larvae). Results from extracts assayed with inhibitor are stippled. All assays were performed in duplicate. Units of activity are expressed as substrate hydrolysis at 405 nm/min/mg extract protein (±standard deviation). (A) Inhibition of trypsin activity by T1. Trypsin activity was determined using BApNA substrate. (B) Inhibition of chymotrypsin activity by C1. Chymotrypsin activity was determined with SAAPFpNA substrate. T1 almost totally inhibited trypsin activity in the extracts of control larvae, indicating these larvae did not produce NaPI-insensitive trypsins. The extracts from NaPI-fed larvae contained negligible trypsin activity, but this activity could not be inhibited by T1. C1 did not inhibit chymotrypsin activity in the extracts of six control larvae and only partially inhibited the gut chymotrypsins in the rest of the controls indicating the control insects contained a C1-insensitive chymotrypsin. Most of the chymotrypsin activity in extracts from NaPI-fed larvae can be attributed to NaPI-insensitive chymotrypsins. When extracts from control and NaPI-fed larvae were pre-incubated with 80 nM chymostatin, all chymotrypsin activity was abolished.
Figure 2D:
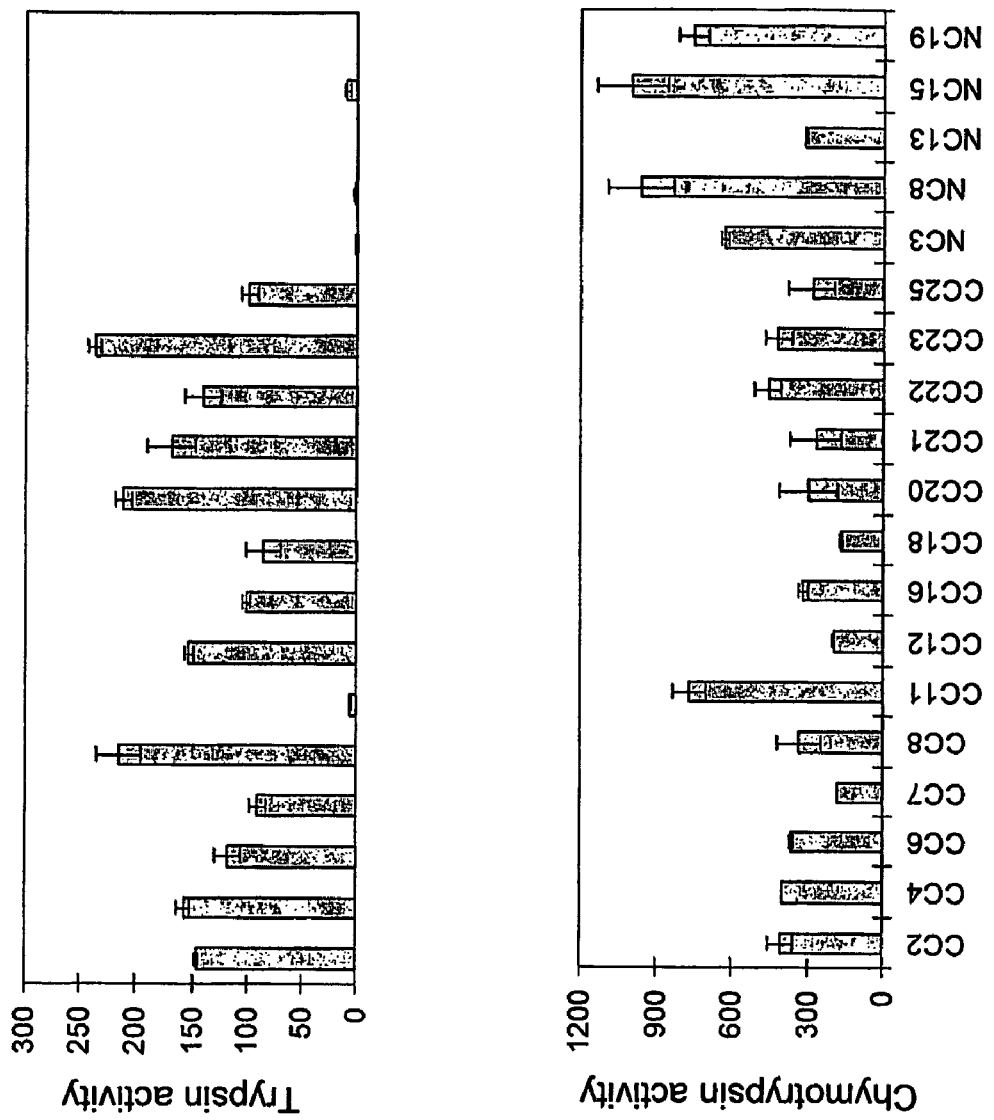
Figure 2E:
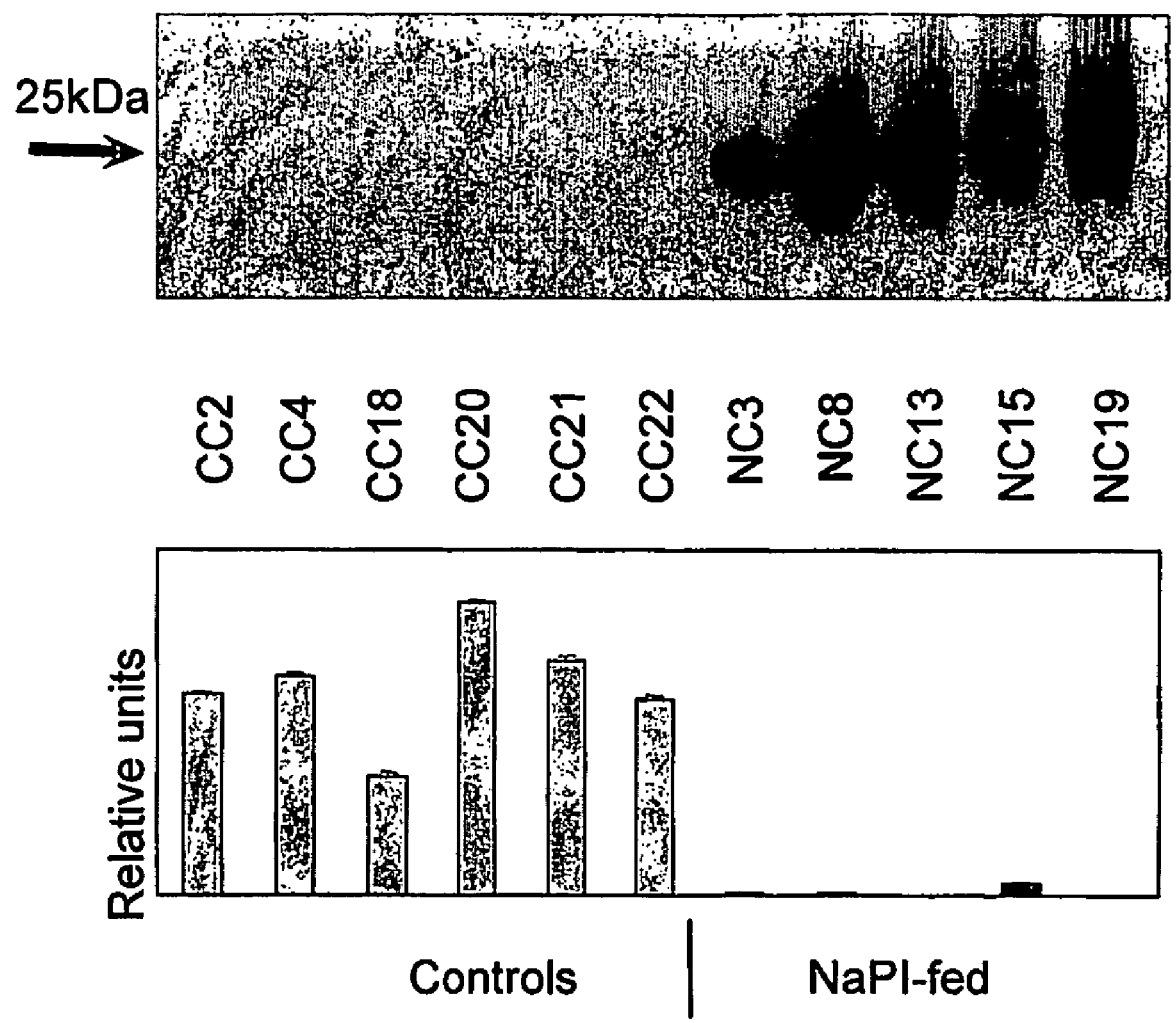
Figure 3:
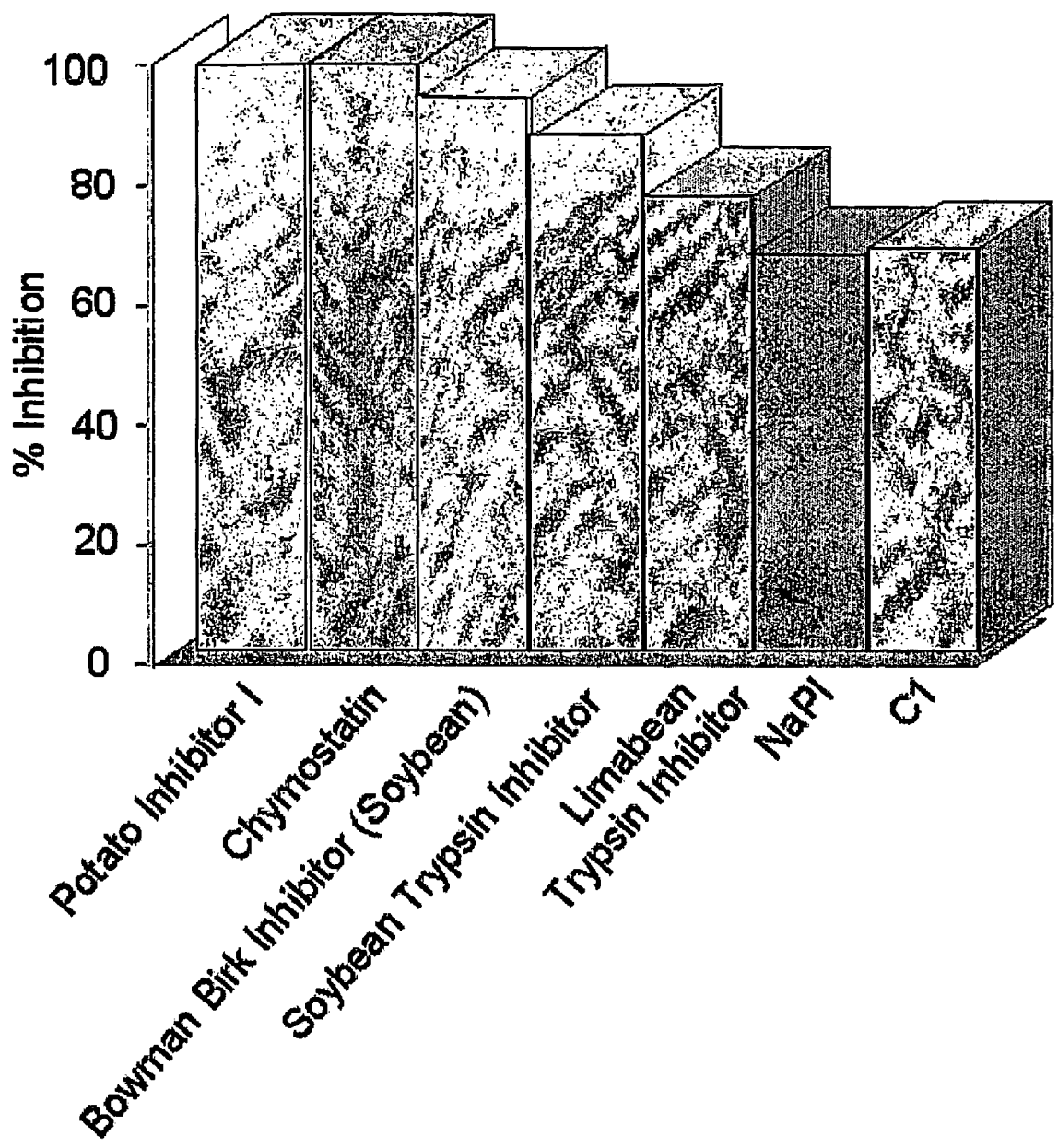
FIG. 3 is a graphical representation showing the effect of various proteinase inhibitors on the chymotrypsin activity in unfractionated gut extracts from *H. punctigera*. Proteinase inhibitors were mixed with 1 μg of protein from an unfractionated gut extract before incubation with the chymotrypsin substrate N-succinyl-Ala-Ala-Pro-Phe-p-nitroanilide. Inhibition is expressed as a percentage of the total activity in the control samples.

The midgut was dissected from 80 fourth instar larvae and buffer soluble extracts were prepared. The gut extract was depleted of trypsins by repeated passage through a benzamidine-Sepharose affinity column. The unbound protein was collected and applied to an affinity column composed of the immobilized chymotrypsin inhibitor C1 (FIG. 1) that had been produced using a bacterial expression system. This column was expected to specifically bind NaPI-sensitive chymotrysins. Proteins that did not bind to this column were applied to a third affinity column composed of either immobilized Potato Type I (PotI) and Type II inhibitors (PotII) or chymostatin. This column was designed to capture the chymotrypsins that did not bind to the C1 column, that is, the NaPI-insensitive chymotrypsins. Proteins that bound to the affinity columns were eluted with 8 M urea and were subjected to electrophoresis through an SDS-polyacrylamide gel before transfer to a PVDF membrane for N-terminal sequencing (FIGS. 4 and 5).

Figure 5:
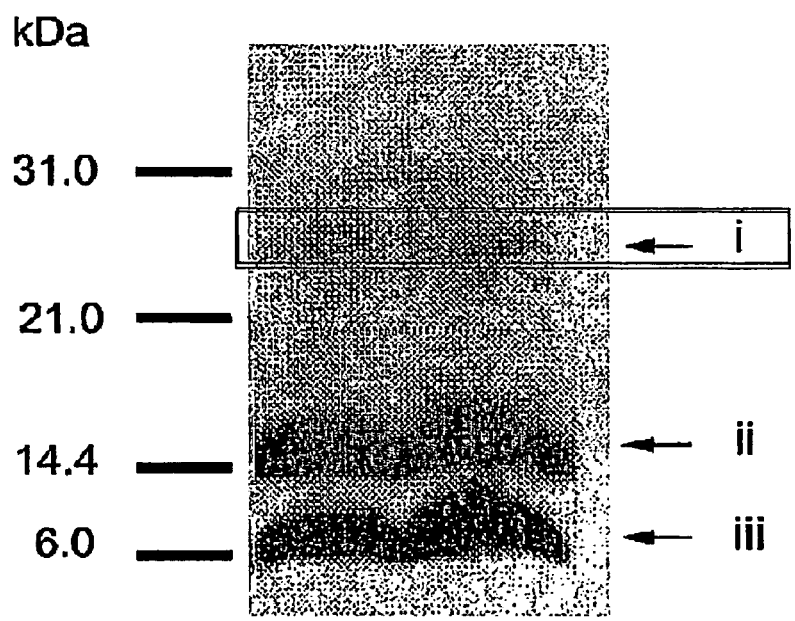
FIG. 5 is a diagrammatic representation showing purification and N-terminal sequence of an NaPI-insensitive chymotrypsin from *H. punctigera*. (A) PVDF blot of chymotrypsin (i) eluted from potato inhibitor column. Potato Inhibitor II (ii) and potato inhibitor I (iii) both co-eluted from the matrix under denaturing conditions. (B) N-terminal amino acid sequence obtained from PVDF blot. Rechla was the most abundant of the four sequences obtained.

About 30 amino acids of N-terminal sequence were obtained that confirmed that the proteins were indeed. chymotrypsins, and that the sensitive and insensitive chymotrypsins were products of different genes (FIGS. 4 and 5).

Figure 6:
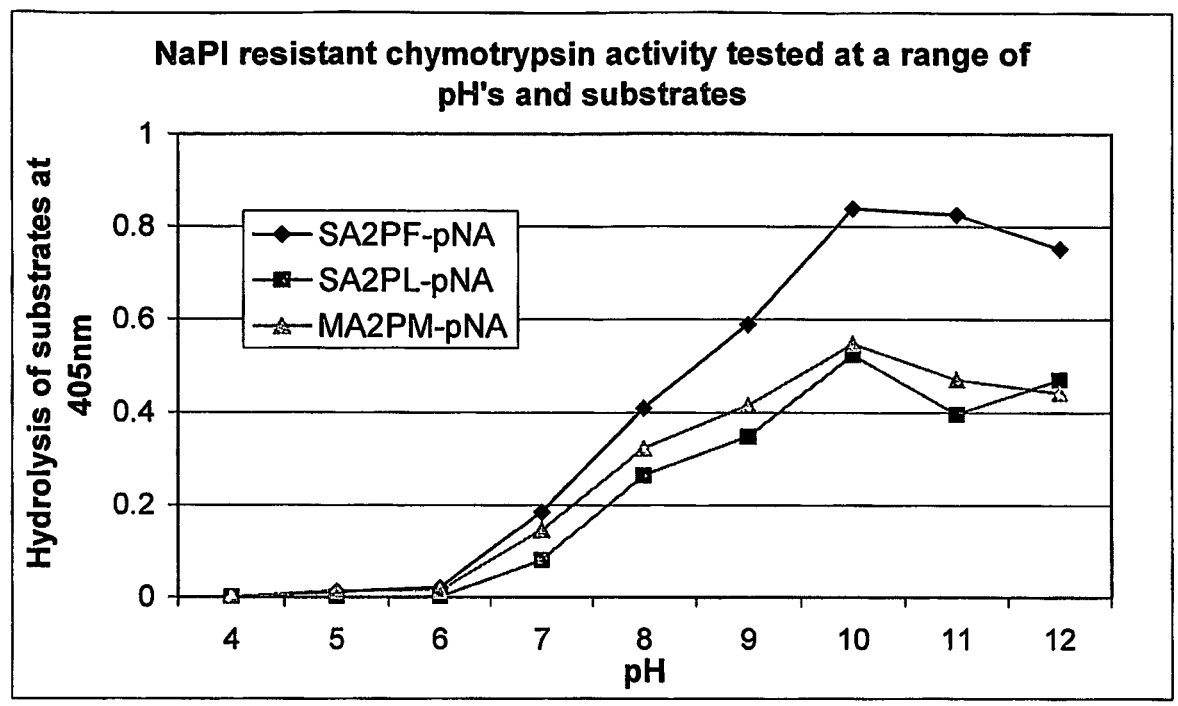
FIG. 6 is a graphical representation showing the effect of pH and a range of substrates on the activity of the NaPI-insensitive chymotrypsin from *H. punctigera* midgut. $SA_2PF$-pNA, N-succinyl-Ala-Ala-Pro-Phe-p-nitroanilide; $SA_2PL$-pNA, N-succinyl-Ala-Ala-Pro-Leu-p-nitroanilide; $MA_2PM$-pNA, N-methoxysuccinyl-Ala-Ala-Pro-Met-p-nitroanilide.

Preparation of NaPI-Insensitive Chymotrypsin Depleted of Trypsins and NaPI Sensitive Chymotrypsins for Biochemical Analysis The midgut was dissected from 100 fourth instar larvae and buffer soluble extracts were prepared. The gut extract was depleted of NaPI-sensitive proteases by passage through an affinity column composed of immobilized NAPI protein (C1, C2, T1-T4). All trypsins and NaPI-sensitive chymotrypsins bound to the column and the NaPI-insensitive chymotrypsin was unbound. This preparation of unbound material was used to study the pH optimum, substrate preference and effect of a range of proteinase inhibitors on the activity of the NaPI-insensitive proteinase. The effect of pH on activity of the insensitive chymotrypsins is illustrated in FIG. 6. The enzyme is inactive below pH6 and is most active at pH10-12 consistent with its role in the alkaline midgut of larvae. The best substrate for enzyme assays was determined using seven different commercial substrates. The best substrate was N-succinyl-Ala-Ala-Pro-Phe-p-nitroanilide (sAAPF-pNA) followed by N-succinyl-Ala-Ala-Pro-Leu-p-nitroanilide (sAAPL-pNA) and N-methoxysuccinyl-Ala-Ala-Pro-Met-p-nitroanilide (mAAPM-pNA). N-succinyl-Ala-Ala-Ala-p-nitroanilide (sAAA-pNA), benzoyl-tyr-p-NA, Ac-Pro-Leu-Ser-p-NA and Ac-Asn-Gly-Ile-Pro-p-NA were not substrates.

Several proteinase inhibitors were tested for their ability to inhibit the activity of the insensitive chymotrypsins. The buffer used for all assays was 500 mM CAPS, 75 mM NaCl, 2.5 mM $MgCl_2$ at pH 10. The inhibitors were preincubated with 100 ng of bovine. chymotrypsin or the amount of the gut chymotrypsin required to produce the same absorbance as 100 ng of bovine chymotrypsin (note that the *Helicoverpa* enzyme has been depleted of trypsins and sensitive chymotrypsins, but still contains other gut proteins) for 30 min at 30° C. before the addition of substrate. The incubation was continued for a further 30 min at room temperature before absorbance was measured at 405 nm. PotI was the best of the proteinaceous inhibitors and NAPI did not inhibit (Table 3).

Experimental Protocols

Benzamidine Column

Benzamidine-agarose (1 mL; was purchased from ICN Biomedicals) and contained 35 umoles benzamidine per ml of gel.

Production of the C1-Affinity Column

DNA encoding the C1 domain of NaPI (FIG. 1, Atkinson et al., 1993, supra) was amplified from the pNa-PI-2-cDNA (Atkinson et al., 1993, supra) using oligonucleotide primers that incorporated BamH1 (5' GACCAGCCGGATC-CGATCGGATAT GCACCAAC) [SEQ ID NO:7] and HindIII (3' GGAGCCAAGCCAAGCTTTGAACGCG GGCAAACTC) [SEQ ID NO:8] sites for cloning into a pQE expression vector (Qiagen). The PCR product was subcloned into the pCR (registered trademark) 2.1-TOPO vector (Invitrogen) then excised with BamHI and HindIII and ligated into the pQE-30 vector. The expression vector incorporated a hexahistidine tag at the N-terminus of the expressed protein for metal affinity purification. The C1/pQE-30 construct was transformed into the chemically competent *E. coli* strain M15 (Qiagen) prepared according to the method of Inoue et al., *Gene* 96: 23-28, 1990. Bacterial expression cultures were grown and induced according to the procedures outlined in the QiaExpress manual (Qiagen). Expression of the 6H.C1 recombinant protein was achieved by induction with 1 mM of IPTG. Samples (1 ml) were removed from the culture at hourly intervals, collected by centrifugation and resuspended in 1×SDS loading buffer (100 µL) for SDS-PAGE analysis.

Recombinant C1 inhibitor was purified under denaturing conditions using Talon Metal Affinity Resin (2 mL) (BD Biosciences Clontech) according to the manufacturer's protocol. C1 was eluted from the affinity matrix and examined using SDS-PAGE to confirm purity. Subsequent rounds of expression were conducted under the same conditions and C1 from a total of 2L of culture was purified using the Talon resin. After washing to remove unbound proteins the C1 inhibitor remained bound to the Talon resin which was then used as the affinity column to purify chymotrypsins from gut preparations.

Potato Inhibitor I and Potato Inhibitor II Affinity Column

Cyanogen bromide-activated Sepharose 4B (1 g) was swollen and washed according to the manufacturer's protocol. A mixture of potato I and II Inhibitors (10 mg) was dissolved in coupling buffer [0.1 M $NaHCO_3$, 0.5 M NaCl, pH 8.3], combined with the gel suspension and incubated over night at 4° C. in an end-over-end mixer. The gel was rinsed several times in blocking buffer [0.1 M Tris-HCl, pH 8.0] to remove excess ligand. Following the washes the conjugated Sepharose was mixed with fresh blocking buffer and incubated overnight at 4° C. The gel slurry was transferred to a column (Amersham Biosciences) and washed alternately (×3) with five column volumes of coupling buffer then five column volumes of rinse buffer [0.1 M NaOAc, 0.5 M NaCl, pH 4.0]. Finally the matrix was extensively washed with coupling buffer and stored in 20% (v/v) ethanol at 4° C.

Chymostatin Affinity Column

Chymostatin (Sigma-Aldrich) was immobilized on EAH Sepharose4B (1.5 ml; Sigma-Aldrich) according to the manufacturer's instructions. Chymostatin (10 mg) was dissolved in 500 µL of glacial acetic acid then 1 mL of distilled water was added and the pH adjusted to 4.5 with dilute NaOH. The gel suspension and chymostatin solution were combined before EDC [N-ethyl-N'-(3-dimethylaminopropyl) carbodiimide] was slowly added to a final concentration of 0.1 M. The gel suspension was mixed overnight at 4° C. before the gel was washed with Milli-Q filtered water to remove excess ligand and unreacted carbodiimide and the gel matrix was stored at 4° C. in 20% [(v/v)] ethanol.

Purification of NaPI-Sensitive and Insensitive Chymotrypsins

Eighty gut from fifth instar larvae that had been stored at −80° C. were homogenized using a mortar and pestle in 10 ml of gut extraction buffer (20 mM CAPS pH 10, 350 mM NaCl). The gut extract was centrifuged at 15,000 g for 15 min at 4° C. and the supernatant was filtered through a syringe filter (0.45 µM; Millipore) then briefly stored on ice before application to the benzamidine affinity column.

The filtered gut extract was passed through the benzamidine column five times to remove the trypsins. The unbound fraction (10 mL) was passed through the C1 affinity column (×3) before the column was washed with 20mL of extraction buffer and bound proteins were eluted with 8 M urea, pH 8.0 (5 mL). Proteins that did not bind to the C1 column were applied to the Potato Inhibitor I and II affinity column prior to washing with 10 column volumes of buffer [20 mM CAPS pH 10, 0.5 M NaCl] and elution of bound proteins with 8 M urea, pH 8.0 (5 mL).

Analysis of Affinity Purified Gut Proteins: SDS-PAGE

Samples of gut proteins (5-10 µg) were concentrated using TCA precipitation and resuspended in 0.2 M NaOH (10 µL).

SDS-PAGE sample buffer (50 mM Tris-HCl, pH 6.8, 2% (w/v) SDS, 10% (v/v) glycerol, 5% (v/v) β-mercaptoethanol, 0.1% (w/v)] bromophenol blue) was added and samples were heated to 100° C. for 5 min prior to separation on 12.5% (w/v) reducing polyacrylamide gels using the MiniProtean II Electrophoresis apparatus (Bio-Rad) at 200 Volts. Broad range or peptide molecular size markers (Bio-Rad) were used to estimate relative molecular masses. Following electrophoresis the proteins were visualized by staining with Coomassie Brilliant Blue R-250 (0.1% (w/v) in 40% (v/v) methanol, 10% (v/v) acetic acid) for 60 min followed by destaining in 40% (v/v) methanol, 10% (v/v) acetic acid or were transferred to either nitrocellulose (0.22 µM pore size; Micron Separations Inc.) or Sequi-Blot Polyvinylidene Fluoride membrane (PVDF; Bio-Rad).

Immunoblotting and N-Terminal Sequencing

After electrophoresis gels were equilibrated in transfer buffer (192 mM glycine, 48 mM Tris-base, 20% (v/v) methanol) for 10 min prior to the transfer of proteins to a nitrocellulose membrane (0.22 µM pore size; Micron Separations Inc.) using the Mini Trans-Blot apparatus (BioRad) at 100 V for 60 min. Membranes were briefly washed in TBS (20 mM Tris-HCl, 150 mM NaCl, pH 7.5) then stained with amido black (1:50 dilution of 0.1% (w/v) amido black, 40% (v/v) methanol, 10% (v/v) acetic acid) to confirm transfer of the proteins and to visualize the molecular size markers. Blots were then blocked by incubation with 3% (w/v) skim milk powder (Dutchjug) in TBST [0.1% (w/v) Tween-20 in TBS] for 1 h at RT, followed by a 1 h incubation with the α-chymotrypsin antibody (HpCH2B; 1:5000 dilution in 3% (w/v) skim milk powder in TBST). The nitrocellulose blots were then rinsed three times (5 min) in TBST and incubated for 1 hour at RT with the secondary antibody (anti-rabbit IgG conjugated to horseradish peroxidase diluted 1:5000 in TBST; Amersham Biosciences). Membranes were washed three times (5 min) with TBST and immunoreactive proteins were visualized with Enhanced Chemiluminescence (ECL) reagents and Hyperfilm ECL X-ray film (Amersham Biosciences) according to the manufacturer's instructions.

To obtain N-terminal sequence, samples were transferred to Sequi-Blot PVDF membrane (BioRad) equilibrated in electroblotting buffer (10 mM CAPS, 10% (v/v) methanol, 0.01% (w/v) SDS, pH 11) using the Mini Trans-Blot cell (BioRad) at 100 V for 45 minutes. Following transfer, the membrane was briefly rinsed in Milli-Q water, stained with Coomassie Brilliant Blue (0.1% Coomassie Blue R-250, 1% (v/v) acetic acid, 40% (v/v) methanol) and then destained (50% (v/v) methanol). Finally the membrane was rinsed with water and dried before excision of the appropriate proteins for N- terminal sequencing.

EXAMPLE 3

Cloning cDNAs Encoding Gut Chymotrypsins from *H. punctigera* cDNAs encoding the *H. punctigera* chymotrypsins were obtained using two approaches. Both approaches employed PCR amplification of cDNA produced from midgut mRNA extracted from *H. punctigera* larvae at the late fourth and early fifth instar stage of development.

Isolation of Chymotrypsin Clones Using Oligonucleotides Complimentary to Highly Conserved Regions in *H. armigera* Chymotrypsins Bown and colleagues (1997, supra) have described several cDNA clones encoding *H.armigera* chymotrypsins. FIG. 7 shows the predicted proteins and the regions complementary to the oligonucleotides (FIG. 8) chosen for PCR amplification of chymotrypsin cDNAs from *H. punctigera*. The PCR products were cloned and sequenced, and five distinct chymotrypsin sequences were obtained (F1Apcr, F1Bpcr, F2Bpcr, F3pcr and F4pcr, FIG. 9). These PCR products were used to screen a cDNA library prepared from midgut mRNA isolated from late fourth instar and early fifth instar larvae. Seven distinct cDNA clones were isolated encoding chymotrypsins that were divided into four families based on sequence identity (FIG. 10, Table 2). These chymotrypsins share high sequence identity with the *H. armigera* chymotrysins described by Bown et al., 1997, supra and with the small number of chymotrypsin sequences reported for *H. virescens* and *H. zea* (Table 6). The chymotrypsins encoded by the full length clones presented in FIG. 10 characteristically encode zymogens of approximately 292-295 amino acids, including putative amino-terminal signal peptides of 16-17 residues predicted by the signal peptide prediction program PSORTII. The presence of the residues IVGG (positions 62-65) at the N-terminus of several active chymotrypsins results in the prediction of activation peptides ranging from 35-44 residues in length on the zymogens predicted from the cDNA clones. Furthermore these activation peptides consistently have the dipeptide arginine-isoleucine at their C-termini suggesting a role for trypsin in activating the chymotrypsins. The sequence identities for the mature domains of each translated protein are presented in Table 2. Family 4 was most divergent with less than 20% identity with the other families, while families 2 and 3 shared most similarity with scores of about 85%. The N-terminal sequence obtained from the NaPI inhibitable chymotrypsin (FIG. 4) matched the N-terminal sequence predicted from the cDNA clones encoding chymotrypsins from family 2. The N-terminal sequence of the NaPI-insensitive chymotrypsins was not represented in the 4 families of chymotrypsins represented by the cDNA clones.

TABLE 5

Protein sequence identity (%) betweeen members of the *H. punctigera* chymotrypsin gene family (mature chymotrypsin domain only)

| H. punctigera chymotrypsin families | HpCh1AI | HpCh1BI | HpCh2A | HpCh2B | HpCh3A | HpCh3B | HpCh4AI | HpCh5 |
|---|---|---|---|---|---|---|---|---|
| HpCh1AI |  | 90 | 54 | 53 | 58 | 59 | <20 | 57 |
| HpCh1BI |  |  | 51 | 51 | 56 | 56 | <20 | 55 |
| HpCh2A |  |  |  | 94 | 83 | 87 | <20 | 73 |
| HpCh2B |  |  |  |  | 82 | 82 | <20 | 72 |
| HpCh3A |  |  |  |  |  | 92 | <20 | 70 |
| HpCh3B |  |  |  |  |  |  | <20 | 72 |
| HpCh4AI |  |  |  |  |  |  |  | <20 |

TABLE 6

*H. punctigera chymotrypsins are closely related to chymotrypsins from other Helicoverpa species*

| Helicoverpa punctigera chymotrypsins | GenBank accession | Species | % amino acid sequence identity |
|---|---|---|---|
| HpCh1AI | Y12273 | Helicoverpa. armigera | 92 |
|  | AF237417 | Heliothis virescens | 86 |
| HpCh1BI | Y12273 | H. armigera | 91 |
|  | AF237417 | H. virescens | 88 |
| HpCh2A | Y12287 | H. armigera | 97 |
|  | Y12280 | H. armigera | 95 |
|  | Y12281 | H. armigera | 95 |
|  | AF233734 | H. zea | 94 |
| HpCh2B | Y12287 | H. armigera | 92 |
|  | Y12280 | H. armigera | 91 |
|  | Y12281 | H. armigera | 90 |
| HpCh3 | Y12279 | H. armigera | 96 |
|  | Y12287 | H. armigera | 82 |
| HpCh4I | Y12272 | H. armigera | 89 |
| HpCh5 | AAO75039 | Spodoptera frugiperda | 80 |
|  | Y12281 | H. armigera | 74 |

Protein sequences most similar to *H. punctigera* were obtained using the BLAST search engine. Genbank accession numbers are listed. The mature activated proteins were compared and percentage of protein sequence identity determined.

The N-terminal region of the insensitive chymotrypsins had two unique stretches of sequence, designated F1 and F2 that were used to design oligonucleotides for PCR amplification of DNA encoding one of the insensitive chymotrypsins (FIG. 11) A 641 bp fragment of DNA was obtained with the F1 oligonucleotide that encompassed most of the protein-coding region. This PCR product was used to screen for a full length clone in the *H. punctigera* midgut library. Approximately 0.2% of the 50,000 plaques screened hybridized strongly to the PCR product. Ten plaques were selected and and a full length clone was identified and sequenced (FIG. 12). The 921 bp clone had an open reading frame of 828 bp and residues 41-76 of the deduced protein were an identical match to the N-terminal sequence obtained from the purified protein (FIG. 12). The clone lacked the 5' signal peptide sequence, but comparison to the other chymotrypsin clones indicated the activation peptide was full length. The active enzyme is predicted to be 236 aa in length, with a mass of 24.2 kda. Protein sequence homology was determined by comparing the mature domains of each of the *H. punctigera* cDNAs. Family 2 and family 3 were most similar to HpCh5 (Rechla), with about 72 and 70% identity respectively. Family 1 members shared 53-57% identity while Family 4 had about 20% identity with HpCh5. Comprehensive Blast searches at the NCBI facility of both translated and protein databases produced no significant matches. The insensitive chymotrypsin belongs to a new family of *Helicoverpa* chymotrypsins designated Family 5 (FIG. 13). A blast search performed on a *Helicoverpa armigera* midgut EST database matched a clone with over 97% sequence identity and 100% sequence similarity FIG. 14.

Bovine chymotrypsins. A and B and the NaPI-sensitive chymotrypsin (HpCh2A) were compared to the insensitive chymotrypsin (HpCh5) to identify regions of variability that may be involved in low affinity binding to C1 (FIG. 15).

Ten substitutions identified in the alignment did not appear to fall into functionally significant regions, whereas the eleventh substitution was associated with one of the β-strands that forms a wall of the primary substrate-binding pocket. The location of this substitution and conversion to an arginine is highly unusual for the S1 domain that is predominantly lined with non-polar residues that define chymotrypsin specificity.

Experimental Protocols

Preparation of RNA

Fifty late fourth and early fifth instar larvae were cold anaesthetized before the gut was removed and snap frozen in liquid nitrogen. The 50 gut were ground to a fine powder in the presence of liquid $N_2$ using a mortar and pestle and were stored at −70° C. The gut tissue (100 mg) was added to 1 mL of TRIZOL (trademark) reagent (Life Technologies) and total RNA was purified and quantified according to the manufacturer's protocol.

RT-PCR Amplification of Chymotrypsin Genes

Chymotrypsin genes from *Helicoverpa armigera* were aligned using ClustalW and regions of high conservation were identified for design of chymotrypsin specific primers. Primers were individually designed to the *H. armigera* clone (CAA72951) due to the high level of divergence to the other chymotrypsin sequences. Forward primers were used in combination with RVG4 to amplify the gene fragments using reverse transcriptase polymerase chain reaction (RT-PCR; Superscript Preamplification System, Gibco BRL) with the protocols supplied. The PCR products were gel purified (Qiagen gel extraction kit), sub-cloned into TOPO PCR2.1 TA cloning vector (Invitrogen) and transformed into chemically competent *E. coli* XL1-Blue cells (Stratagene) prepared according to the method of (Inoue et al., 1990, supra). Plasmid DNA was prepared using the QIAprep (registered trademark) Spin Miniprep Kit (Qiagen).

Production and Screening of a *H. punctigera* gut cDNA library: Library Preparation PolyA+ mRNA was isolated from the RNA (1.0 mg) using conventional protocols. A biotinylated oligonucleotide (dT) primer that binds to the polyA tail tags the transcripts that are subsequently captured on streptavidin paramagnetic particles (PolyATract (registered trademark), mRNA Isolation Systems, Promega). Purified mRNA (5 μg) was used to construct a cDNA library with the Lambda ZAP-cDNA synthesis kit and the Zap-cDNA GigapackIII Gold packaging extract (Stratagene) following the manufacturer's instructions. The amplified library titre was $2.8\times10^{10}$ pfu/mL.

Labeling Probes

RT-PCR products (50 ng) were individually labelled with [$\alpha$-$^{32}$P] dCTP (Amersham Life Sciences) using the MEGAPRIME (trademark) DNA labeling system labeling (Amersham Life Sciences). Unincorporated radiolabeled nucleotides were removed using the Micro Bio-spin P-30 chromatography columns (BioRad) according to the manufacturer's protocol. The double stranded labelled probes were denatured by boiling (5 min), cooled on ice, and then added to the hybridization solution (as below).

Screening the cDNA Library

The primary screen was performed using ten (15 cm) Petri dishes per probe, with about 50,000 phage per plate. Preparation of the plates for subsequent plaque lifts and treatment of the membranes prior to hybridization was performed according to instructions provided with the Lambda Zap cDNA synthesis kit (Stratagene). The membranes (Hybond-N; Amersham Biosciences) were prehybridized in 50 ml of 2×PIPES (0.8 M NaCl, 16 mM Piperazine-1,4-bis(2-ethanesulphonic acid) pH 6.5) 50% (v/v) formamide, 0.5% (w/v)

SDS and 100 µg/mL Herring sperm DNA (Boehringer Manningham) at 42° C. for 3 hours. Following prehyridization, the incubation solution was replaced with 50 ml of 50% (v/v) formamide, 2×PIPES buffer, 0.5% (w/v) SDS and 100 µg/mL denatured herring sperm DNA containing the labeled probe and left overnight at 42° C. The hybridization membranes were washed three times in 2×SSPE/0.1% (w/v) SDS at room temperature and twice in 0.2×SSPE/0.1% (w/v) SDS at room temperature, before they were blotted on 3 mm Whatman paper and exposed to X-ray film (Kodak XAR-5) for 48 hours at -70° C with intensifying screens.

Due to crowding and hence overlapping between positive clones and non-specific plaques a secondary screen was conducted to isolate individual clones. Two 8.5 cm plates each with 50 plaques were used for each probe. The secondary screen was conducted as described for the primary screen.

At least 50 positive plaques of varying intensities were selected from each screen probed with an individual RT-PCR product. Each plaque was transferred to a 1.5 mL microfuge tube containing 1 mL of SM buffer (0.1 M NaCl, 8 mM MgSO$_4$.7H$_2$0, 50 mM Tris-HCl, pH 7.5, 0.01% (w/v) gelatin) and chloroform (20 µL) and stored at 4° C. Initially 10 plaques for each probe were excised and converted into pBluescriptII SK(–) phagemids using the ExAssist/SOLR system (Stratagene). The excised phagemids were transformed into the chemically competent E. coli strain XL1-Blue cells and plasmid DNA was prepared and sequenced.

DNA Sequencing and Analysis

The cDNA clones were grouped on the basis of restriction fragment patterns obtained using combinations of the endonucleases BamHI, XhoII, KpnI, SacI, SacII, and SalI (Promega). RT-PCR products and cDNA inserts were sequenced in both directions using M13 universal primers at either Micromon sequencing facility at Monash University (Melbourne) or SUPAMAC at the Royal Prince Alfred Hospital in Sydney. The sequence data was edited using the BioEdit v5.0.9.1 software written by Tom Hall, North Carolina State University freely available at the web address: mbio.ncsu.edu/BioEdit/bioedit. Sequence homologies were assessed using the BLASTN search facility at National Centre for Biotechnology Information (NCBI) and further multiple sequence alignments were performed using ClustalW version 1.4. at the Network Protein Sequence Analysis facility (Combet et al., *TIBS*. 25: 147-150, 2000).

The web based program 'PSORT II' available at the Human Genome Centre at the University of Tokyo, was used to predict signal peptide cleavage points. UTRscan was used to detect functional elements in the 3' untranslated regions of the cDNA clones [Pesole, *Trends Genet*, 15: 378, 1999].

Isolation of a Partial cDNA Clone Encoding a NaPI—Insensitive Chymotrypsin

A sample of RNA previously purified for the production of the CDNA library was thawed and used as template for the following RT-PCR reaction. Two 5' degenerate primers (5) were designed to unique regions of the N-terminal amino acid sequence and used in combination with the 3' primer RVG4. First strand cDNA synthesis was achieved using the SuperScriptII Preamplification system from Stratagene and was followed by PCR amplification of the target cDNA using the Perkin Elmer thermocycler [25 cycles for 1 min at 94° C., 1 min at 48° C. and 1 min at 72° C. then 7 mins at 72° C]. PCR products were separated on 1% (w/v) agarose gel (SEAKEM (registered trademark); Bio Whittaker Molecular Applications) and a band of approximately 650 bp was excised and purified using the Concert purification system (Gibco). The partial cDNA was cloned into the TOPO PCR2.1-TA vector (Invitrogen) and transformed into E. coli strain XL-BL1 (Stratagene).

Isolation of the Insensitive Chymotrypsin cDNA clone

The cDNA library prepared from fourth instar larval gut was screened using a partial fragment cloned according to the techniques described above

EXAMPLE 4

Homology Modeling of the *H. punctigera* Chymotrypsins

The deduced amino acid sequences from the cDNA clones HpF2B (sensitive) and HpF5 (insensitive) were modeled on the structures of the *Bos taurus* (bovine) and fire ant chymotrypsins, obtained from the Research Collaboratory for Structural Bioinformatics (RCSB) Protein Data Bank site. The *Helicoverpa* chymotrypsins are predicted to adopt similar structures to those reported for all the chymotrypsin structures available in the PDB databank. The modeled structure consists of the classic serine protease fold consisting of two, six-stranded anti-parallel β barrels with the catalytic triad located between the two domains. Two surface loops, 60 and 142 are considerably larger in the *H. punctigera* chymotrypsins (FIGS. 15 and 16). Due to the limitations of modelling, a small amount of ambiguity was present in several surface loops, some of which are cleaved in mammalian chymotrypsins (loop 142), but remain intact within insect chymotrypsins. The only reported crystal structure of an insect chymotrypsin is from the fire ant, *Soenopsis invicta* (Botos et al., *Journal of Molecular Biology* 298: 895-901, 2000) and this was used to help refine the orientation of the surface loops on the model of the *Helicoverpa* chymotrypsin.

C1 was modeled in complex with sensitive and insensitive chymotrypsins to investigate whether substitution of glutamine (or asparagine) 192 (Greer nomenclature, FIG. 15) with an arginine would affect the binding capacity of the *Helicoveipa* chymotrypsins. The structure of the chymotrypsin inhibitor (C1) was previously determined by 1H NMR (Nielson et al., 1994, supra). No structures of C1 complexes have been solved and therefore the related proteinase inhibitor PCI-1 from *Solanum tuberosum* in complex with Proteinase B from *Streptomyces griseus* (Greenblatt et al., 1989, supra) provided a basis for structural modeling. FIG. 17 illustrates the binding region surrounding Gln 192 in the C1-HpF2B chymotrypsin complex. The predicted model of HpF2B and C1 shows that glutamine 192 is not in conflict with any regions on the inhibitor molecule. Comparison to the cognate arginine residue in the insensitive chymotrypsin however suggests there is limited space to accommodate this much larger residue (FIG. 18). The modeling viewing program 'Spdbv', predicted Arg 192 to be in direct conflict with threonine 5 of C1. PotI has been identified as a strong inhibitor of the insensitive chymotrypsin from *H. punctigera* and was, therefore, modelled in complex with the insensitive chymotrypsin (FIG. 19). Unlike C1, PotI easily accommodates arginine 192 upon binding to the insensitive chymotrypsin.

In summary, the NaPI-insensitive chymotrypsin from *Helicoverpa* species has an arginine in place of an asparagine or glutamine at position 192 that extends into the S1 binding pocket and appears to interfere with C1 binding. Furthermore, it is clear that this arginine residue does not interfere with PotI binding, consistent with the observation that PotI is a much more efficient inhibitor of insect chymotrypsins than the NaPI inhibitors.

EXAMPLE 5

Production and Characterization of Polyclonal Antisera to the NaPI Inhibitable and NaPI—Insensitive Chymotrypsins from *H. punctigera*

Chymotrypsin clone HpF2B was expressed in *E. coli* fused to a six histidine (6.H) tag at the C-terminus and was purified to homogeneity on Talon metal affinity resin (FIG. 20) for injection into a rabbit for production of polyclonal antibodies. N-terminal sequencing of the purified product confirmed the expression of the NaPI inhibitable chymotrypsin (HpCh2B). After the fourth boost with antigen, the serum was collected and tested on protein blots of bacterially expressed protein and unfractionated gut extracts. The antibody detected the full-length recombinant chymotrypsin at a dilution of 1 in 2500 as well as several break-down products. Unfractionated gut extract and a sample of protein bound to the C1 affinity column were also stained with the anti-HpCh2B antibody which detected the mature native form of the enzyme.

Purified 6H.HpCh2B was used to test the detection limit of anti-HpCh2B antibody by comparison of immunoblots to silver stained SDS-PAGE gels. The antibody detected 20 ng of bacterially expressed chymotrypsinogen and also recognized the mature form of the native chymotrypsin isolated from gut of *H. punctigera*.

The cDNA (HpF5) encoding the NaPI-insensitive chymotypsin (HpCh5) was expressed in *E. coli* in a similar manner except the six.histidine tag was fused to the N-terminus of the expressed protein. The polyclonal antiserum that was raised against the bacterially expressed NaPI inhibitable chymotrypsin (HpCh2B) did not cross-react with bacterially expressed NaPI-insensitive chymotrypsin (HpCh5) on protein blots (FIG. 21). Likewise the antiserum raised against HpCh5 did not bind to HpCh2B. This indicates that these antisera can be used to specifically distinguish between and monitor levels of the NAPI-insensitive and sensitive chymotrypsins in unfractionated gut extracts.

Experimental Protocols

Preparation of Antigen for Immunization

The cDNA clone 'HpF2B' which encodes an NaPI sensitive chymotrypsin (FIG. 11) was amplified by polymerase chain reaction (PCR) using two oligonucleotides (Table 7) that incorporated NcoI and BglII restriction sites at the 5' and 3' ends of the cDNA respectively.

TABLE 7

Degenerate primers designed to two unique regions in the N-terminus of the insensitive chymotrypsin protein. Primer positions are shown in the amino acid sequence by matching typeface
N-terminal sequence of NaPI-insensitive chymotrypsin
IVGGSLSSVGQIPYQAGL*VIDLAGG*QAVCGSLISA
[SEQ ID NO:9]

| Primer Name | Oligonucleotide sequence 5'-3' |
|---|---|
| Fw2ResChy | TC(AGCT) GT(AGCT) GG(AGCT) CA(AG) AT(ACT) CC<br>[SEQ ID NO:10] |
| FwResChym | GT(AGCT) AT(ACT) GA(CT) CT(AGCT) GC(AGCT) GG(AGCT) GG<br>[SEQ ID NO:11] |

TABLE 8

PCR amplification primers for bacterial expression of chymotrypsin HpF2B

| Primer Name | Restriction site | Sequence |
|---|---|---|
| 5' Hc35PQE-60Fw | NcoI | TTA ACC ATG GTG ATC GAC CTC<br>[SEQ ID NO:12] |
| Hc35PQE-60Rv | BglII | GAT GAG ATC TGA GAC GTT GGT TG<br>[SEQ ID NO:13] |

The amplified region consisted of the pro-peptide and mature domain of the chymotrypsinogen, but lacked the putative secretion signal. Digests using NcoI and BglII enzymes (Promega) were performed on the PCR amplified product and the pQE-60 expression vector (Qiagen). The pQE-60 vector provides a His-tag at the C-terminus of the expressed protein. Each restriction digest was purified using WIZARD (registered trademark) DNA clean up system (Promega) and the vector and chymotrypsin insert were subsequently ligated using standard molecular biology techniques (Sambrook and Russell, Molecular Cloning: A Laboratory Manual, Cold Spring Harbor Laboratory Press, 3rd edition 2001) The ligation mix was heated at 65° C. for 10 min before being transformed into the *E. coli* strain XL1-Blue. Plasmid DNA was prepared for sequencing and subsequent transformation into the *E. coli* cell line M15 (Qiagen) using the QIAPREP (registered trademark) Spin Miniprep Kit (Qiagen).

Expression and purification of the recombinant chymotrypsinogen was performed under denaturing conditions according to the methods detailed in the QiaExpress manual (Qiagen). The purity of the expressed chymotrypsinogen was assessed by SDS-PAGE and the identity of the recombinant protein confirmed by N-terminal sequencing. Preparation of the chymotrypsin for injection consisted of removal of the urea by dialysis against 50 mM Tris-HCl pH 8.0. During this process most of the protein aggregated. The aggregated protein was collected by centrifugation and resuspended in 1 mL of 50 mM Tris-HCl, pH 8.0 for injection. The protein concentration was approximated by the comparison of a 10 μL sub-sample to a series of bovine trypsin standards (Sigma) using SDS-PAGE and Coomassie staining.

The cDNA clone 'HpF5' which encodes the NaPI-insensitive chymotrypsin (FIG. 12) was PCR amplified essentially as described for clone HpF2B above except the forward primer (FwpMalRECH ) incorporated a Histidine tag at the N-terminus of the expressed protein and the reverse primer (RvRECH) contained a stop codon and thus prevented incorporation of a Histidine tag at the C-terminus from the pQE-60 expression vector.

EXAMPLE 6

Bioassays with PotI Inhibitor and *Helicoverpa* larvae

Large quantities of the PotI inhibitor were purified from potato tubers to evaluate the combined effect of NaPI and PotI on the growth of *H.armigera* larvae. Bioassays confirmed that addition of PotI significantly enhances the activity of the NaPI inhibitors. Caterpillars fed NAPI and PotI in combination (0.26 and 0.34% (w/v), respectively) were 34% the size of control larvae at the fifth instar stage of development whereas caterpillars feeding on NaPIs alone were about 84% the size of the controls. Based on these results we decided to clone genes encoding the PotI inhibitors for transfer into cotton plants. Two PotI genes (PotIA and PotIB) were isolated using mRNA isolated from potato tubers and wounded potato leaves. These cDNA clones were used to construct vectors for bacterial expression of the Pot proteins. The bacterially produced PotI proteins totally inhibited the NaPI-insensitive chymotrypsin isolated from *H. punctigera* larvae. Both PotI genes were incorporated into constructs for cotton transformation. Purified PotI inhibitor from potato tubers was used to generate specific antibodies that were used to monitor levels of PotI produced by transgenic plants.

Experimental-Protocols

Purification of PotI Inhibitor from Potato Tubers

Potato tubers (2 Kg, *Solanum tuberosum* var Russet Burbank) were diced and soaked overnight at 4° C. in two liters of 50 mM $H_2SO_4$. The tissue was homogenized in a blender and insoluble material was removed by filtration through two layers of Miracloth followed by centrifugation (13,000 rpm, 15 min, 4° C.). The supernatant was adjusted to pH 7.8 with 10 M NaOH, heated for 30 min in boiling water and cooled before precipitated material was separated by centrifugation (13,000 rpm, 12 min, 4° C.). Soluble proteins were precipitated with ammonium sulphate (80% saturation), collected by centrifugation and redissolved in gel filtration buffer (150 mM KCl, 10 mM Tris-HCl, pH 8) before they were applied to a Sephadex G75 column (85×2.54 cm). Elution fractions (50 mL) containing PotI were identified using SDS-polyacrylamide gel electrophoresis and inhibition assays with bovine chymotrypsin. PotI containing fractions were pooled, dialysed and freeze dried. The protein in these pooled fractions was examined by reverse phase -HPLC on a system Gold HPLC (Beckman, Fullerton, Calif.) coupled to a 166 detector (Beckman). The analytical RP-HPLC was conducted on a Brownlee Aquapore RP300 C8 column (4.6×100 mm; Perkin-Elmer). The protein was eluted with a linear gradient of 0-100% (v/v) buffer B (60%[v/v] acetonitrile in 0.089% [v/v] trifluoroacetic acid) at a flow rate of 1 mL min-1 over 40 min (FIG. 22). The identity of the PotI proteins was confirmed by N-terminal sequencing and mass spectrometry and at least two PotI isoforms were identified.

Growth of *H. armigera* larvae on Artificial Diet Containing NAPI and PotI

PotI protein isolated from potato tubers and NAPI peptides isolated from *N. alata* stigmas, were incorporated into a cotton leaf based artificial diet and fed to *H.armigera* neonates (FIG. 23). PotI had an additive affect on larval growth. Larvae fed NaPI only were inhibited in growth by 16% compared to control larvae while larvae fed both NAPI and PotI were inhibited in growth by 75% compared to control larvae (FIG. 23).

Isolation of cDNAs Encoding Potato Proteinase Inhibitor I (Pot1)

Potato proteinase inhibitor I cDNA was synthesized using reverse transcriptase-PCR and total RNA from potato tubers or wounded potato leaves. First strand cDNA was prepared using Thermoscript RT-PCR with Oligo $(dT)_{20}$ primers (Life Technologies). PotI cDNA sequences were subsequently amplified using gene specific primers 5° CGG-GAT-CCA-TGG-AGT-CAA-AGT-TTG-C-3' [SEQ ID NO:14] (sense) and 5'-GCG-TCG-ACG-CTT-AAG-CCA-CCC-TAG-G-3' [SEQ ID NO: 15] (antisense) that were designed to anneal to the 5' and 3' ends of the open reading frame of the published PotI genomic sequence M17108 (Cleveland et al., *Plant Mol. Biol.* 8: 199-207, 1987) and included restriction sites Bam HI and Sal I respectively.

Two PotI homologs were isolated. StPotIA was derived from wounded leaf RNA and StPotIB was derived from tuber RNA. StPotIA and StPotIB cDNA share 92.6% nucleic acid sequence identity and share 86% amino acid sequence identity (FIG. 25).

The predicted amino acid sequence and comparison to other members of the Potato Inhibitor I family are presented in FIG. 24. StPotIB is very similar to published PotI sequences from potato tuber and shares a methionine at the PI reactive site. In contrast, StPotIA contains an alanine residue at PI and also has an additional four amino acids at positions 41 to 44. Additional amino acids in this position have not been reported for other potato PotI isolates although they have been found in a wound induced PotI from tomato.

Expression of StPotIA4 and StPotIB in *E. coli*

DNA encoding PotI without the endoplasmic reticulum signal sequence (amino acids 37-111 in StPotIA and 37-107 in StPotIB) was amplified by PCR. Primers used were 5'-CGG-GAT-CCA-AGG-AAT-CGG-AAT-CTG-3' [SEQ ID NO:16] (StPotIA sense), 5'-CGG-GAT-CCA-AGG-AAT-TTG-AAT-GC-3' [SEQ ID NO:17] (StPotIB sense) and 5'-CGA-GCT-CTT-AAG-CCA-CCC-TAG-G-3' [SEQ ID NO:18] (StPotIA/B antisense). PCR products were initially cloned into the pGEM T-Easy vector (Promega) before they were excised with BamHI and SacI and ligated into the bacterial expression vector pQE30 (Qiagen) which provides a 6x His-tag at the N-terminus of the expressed protein.

The His-tagged PotI proteins were expressed in *E. Coli* (BR21 DE3 Codon Plus strain (Stratagene) for StPotIA and M15 strain (Qiagen) for StPotIB). Cells were induced with 1 mM IPTG, harvested by centrifugation and lysed in 8 M urea, 0.1 M $NaH_2PO_4$, 0.01 M Tris-HCl, pH 8.0. Cell debris was removed by centrifugation at 10,000 g for 5 min and the His-tagged PotI was purified from the supernatant by metal-affinity chromatography on Talon resin (Clontech). Bound protein was eluted from the resin with 8 M urea, 0.1 M $NaH_2PO_4$, 0.01 M Tris-C1, pH 4.0 and elution was monitored by SDS-PAGE. The StPotIA and StPotIB proteins were purified further by RP-HPLC (FIG. 25) their identity was confirmed by N-terminal sequencing and mass spectrometry.

Inhibition of the NaPI-Insensitive Chymotrypsins from *H. punctigera* by StPotIA and StPotIB The inhibitory activity of StPotIA and StPotIB against the NaPI-insensitive chymotrypsins from *H punctigera* was determined by preincubating the NaPI-insensitive protease (10 µL) with varying amounts of StPotIA and StPotIB (0-600 nM) in 133 mM CAPS buffer, pH 10.0 at 30° C. in 96 well microtitre plates. After the 30 min preincubation, the incubation was started by the addition of substrate ($SA_2PFpNA$, SA₂PLpNA or SA₂PMpNA) to a final concentration of 1 mM in a final volume of 100 μL. Absorbance was measured at 405 nm after 30 or 60 min.

StPotIA, StPotIB and the mix of PotI isoforms isolated from potato tuber inhibited the NaPI-insensitive chymotrypsin in the *Helicoverpa punctigera* gut extract (FIG. 26). At least 75% of SA₂PFpNA or SA₂PLpNA hydrolysis by the NaPI-insensitive chymotrypsin was inhibited by the addition of 300 nM of StPotIA, StPotIB or a mix of PotI isoforms isolated from tuber. Inhibition of SA₂PMpNA hydrolysis was lower (40%).

Production of Transgenic Cotton Expressing NaPI and StPotIA

Two gene constructs (pHEX2 and pHEX6) were prepared for transformation of cotton (*Gossypium hirsutum*). pHEX2 consists of a 35S promoter driving the NaPI gene with a 35S terminator, inserted into the binary vector pBIN 19 (Bevan, *Nucl. Acids Research*, 12: 8711-8721, 1984). pHEX6 consists of a 35S promoter driving the StPotIA gene with a 35S terminator inserted into the binary vector pBIN 19.

Transgenic cotton was produced using the method of Umbek et al., *Biotechnology*, 5: 263-266, 1987) with modifications. Hypocotyl sections of cotton Cv Coker 315 were co-cultivated with *Agrobacterium tumefaciens* strain LBA 4404 containing the required binary vector. Callus was induced on media consisting of MS salts, B5 vitamins, 3% glucose, 0.9 g/L MgCl₂ (hexahydrate), 1.9 g/L potassium nitrate, 2 g/L Gelrite, 0.1 mg/L Kinetin, 0.1 mg/L 2,4-D, 500 mg/L carbenicillin, 35 mg/L Kanamycin. Embryogenic callus was induced by growing the callus on the same media but without hormones. Embryos were excised and incubated on media in petri dishes (Stewart and Hsu, *Planta* 137: 113-117, 1977). Germinated embryos that had produced roots and true leaves were transferred to containers for further development and then transferred to soil and grown in a growth cabinet at 27° C.

Production of Transgenic Cotton Expressing NaPI and StPotIA

To produce plants expressing both genes, pollen from a transgenic line expressing NaPI was used to pollinate a flower from a plant expressing StPotIA and the seed collected. One progeny plant (plant 3) was identified as expressing both genes by immunoblot analysis.

Leaves from plant 3 were used in a bioassay with *H. armigera* (FIG. 27). While expression of either NAPI or StPotIA in the leaves only resulted in a small inhibition of larval growth compared to the control, expression of both proteins had a synergistic effect on larval growth.

EXAMPLE 7

Baculovirus Expression of HpCh5

Addition of the Signal Peptide Sequence to HpCh5

While the HpF5 clone encoded the entire chymotrypsinogen sequence of HpCh5 with the activation domain it did not encode the signal peptide required for correct targeting of the protein to the endoplasmic reticulum (ER). For baculovirus expression, an ER signal sequence was added to the HpF5cDNA using two overlapping oligonucleotides corresponding to the 19 amino acids of the ER signal peptide from HpCh2A (FIG. 10). The ER signal sequence was added to the preactivation and mature domains of HpCh5 in a two-step PCR (Table 9).

TABLE 9

PCR amplification primers for addition of an ER signal sequence to HpCh5

| Primer | Sequence |
| --- | --- |
| FWBacRECH1 (5'-3') | TTG GCT TTC GCC GCG GTC GTC TCC GCG AGG AAC GGG TCC C [SEQ ID NO:19] |
| FWBacRECH2 (5'-3') | GGA TCC ATG AAA CTC TTG GCT GTG ACT CTA TTG GCT TTC G [SEQ ID NO:20] |
| RvRECH (3'-5') | G ATC AAC GGC GAG CTC TAA AAG CTT [SEQ ID NO:21] |

The first PCR used primers FwBacRECH1 and RvRECH with the HpF5 cDNA template to add the first half of the ER signal sequence. The second PCR used FwBacRECH2 together with RvRECH and the product of the first PCR reaction as template. At each step, the amplification products were purified after electrophoresis on 0.7% (w/v) agarose gels before they were used for subsequent PCRs.

Cloning of HpFS/ER into pFastBac Vector

The HpF5 cDNA with the ER signal sequence (HpF5/ER) was subcloned into the pCR (registered trademark)-2. 1 TOPO vector (Invitrogen) and was sequenced at the Micromon, DNA sequencing facility, Monash University, Victoria, Australia. Recombinants with the correct sequence were digested with EcoRI and gel purified before they were digested with BamHI and HindIII and ligated into the pFastBac vector (Invitrogen) and transformed into *E. coli* XL1 Blue cells.

Transposition of pFastBac/HpF5/ER Construct into *E. coil* DH10Bac Cells

*E. coli* XL1 Blue cells were screened for the presence of the HpF5/ER cDNA in the pFastBac vector (pFastBaclHpF5/ER) by PCR and restriction digest. Minipreps were performed on positive transformants. *E. coli* DH10Bac competent cells containing bacmid DNA and the helper plasmid required for transposition of HpF5/ER to the bacmid DNA were thawed on ice. Approximately 1 ng of pFastBac/HpF5/ER recombinant plasmid was added to the cells (150 μL) and after gently mixing the mixture was transferred to a pre-chilled GENE PULSER (registered trademark)/*E. COLI* (trademark) pulser cuvette. The cuvette was placed in the electroporation apparatus (BioRad) and a pulse of 1.7 Amps was applied. LB (1 mL) was then added and the sample was transferred to a 10 mL capped tube and allowed to recover on a shaking incubator (190 rpm) at 37° C. for 4 hours. A sample was withdrawn and serially diluted ($10^{-1}$, $10^{-2}$, and $10^{-3}$) using LB medium before 100 μL of each dilution was spread evenly onto LB agar plates containing 50 μg/mL kanamycin, 7 μg/mL gentiamicin, 10 μg/mL tetracycline, 100 μg/mL 5-bromo-4-chloro-3-indolyl-β-D-galactopyranoside (X-Gal) and 40 μg/mL IPTG prior to incubation for 48 hours at 37° C. A pFastBac vector with no insert was treated the same way and used as a control.

Isolation of Recombinant Bacmid DNA

Recombination between the pFastBac/HpF5/ER vector and the bacmid DNA was detected by the presence of white colonies as apposed to blue colonies, indicating a disruption in the lacZa gene. To confirm the recombination was stable, the colonies were restreaked on selective media and incubated for 24 hours. White colonies were used to inoculate 10 mL LB media containing 50 μg/mL kanamycin, 7 μg/mL gentiamicin and 10 µg/mL tetracycline for isolation of the recombinant bacmid DNA. The same procedure was performed with a blue colony (not recombinant) selected as a control. Cells were grown overnight at 37° C. with shaking at 190 rpm. Cultures were centrifuged at 14,000×g for 5 min. The supernatant was discarded and the pellet was resuspend in 0.3 ml of Solution I (15 mM Tris-HCl, pH 8.0, 10 mM EDTA, 100 µg/mL RNase A]. Solution II (0.2 N NaOH, 1% (w/v) SDS) was then added and gently mix and incubated at room temperature for 5 min. Potassium acetate (0.3 mL, 3 M, pH 5.5) was slowly added and the samples were placed on ice for 10 min before, they were centrifuged for 10 min at 14,000×g to remove the thick white precipitate. The supernatant was then transferred to a 1.5 mL microfuge tube containing 0.8 ml absolute isopropanol and was mixed by inversion. After 10 min on ice samples were centrifuged for 15 min at 14,000×g at room temperature. The supernatant was removed and pellet was washed twice with 0.5 mL of 70% (v/v) ethanol. The sample was then centrifuged for 5 min at 14,000×g at room temperature before the 70% (v/v) ethanol was removed and the DNA pellet was air dried. The DNA was then dissolved in 60 µL TE buffer (10 mM Tris-HCl, 1 mM EDTA, pH 8.0) and stored at −20° C. until needed. The bacmid was examined by electrophoresis on a 0.5% (w/v) agarose gel prepared in TAE (40 mM Tris-acetate, 1 mM EDTA, pH 8) buffer at 23 V for 12 hours with λ DNA/HindIII Fragment markers (MBI Fragments). The bacmid was also screened using PCR with M13 Forward and reverse primers.

Transfection of HIGH FIVE (trademark) Cells with Recombinant Bacmid DNA

Approximately 9×10⁵ HIGH FIVE (trademark) insect cells were placed into a 35-mm well in a 6-well plate (NUNCLON (trademark) Δ Surface) in 2 ml of EX-CELL (trademark) 405 media with 50 units/mL penicillin and 50 µg/mL streptomycin (JRH Biosciences). Cells were left at 27° C. for 1 hour to allow them to attach to the plate. Two solutions were prepared for each transfection each adding a different amount of bacmid miniprep (5, 10 or 20 µL); Solution A: mini-prep of bacmid DNA into 100 µL EX-CELL (trademark) 405 media without antibiotics, and Solution B: 6 µL of CELLFECTIN (registered trademark) Reagent (Gibco BRL) into 100 µL EX-CELL (trademark) 405 media without antibiotics. Solutions A and B were combined and incubated for 1 hour at room temperature followed by 0.8 mL of selection free media added. After the cells had attached to the plate, they were washed once with 2 mL media without antibiotics. The media was removed from cells and was replaced with the DNA containing solution. Cells were incubated for 5 hours in a 27° C. incubator before the transfection mixture was aspirated and replaced with 2 mL of media containing antibiotics. Cells were incubated further at 27° C. for up to 72 hours.

After 24, 48 and 72 hours, 2 mL of the supernatant was transferred to a 10 mL sterile capped tube and centrifuged for 5 min at 500×g. The virus-containing supernatant was transferred to a fresh tube and stored at 4° C., protected from light until required.

Infection of Insect Cells with Recombinant Baculovirus Particles

Two 10 mL cultures were set up for each transfection. Each culture was infected with 100 µl of harvested virus (~2×10⁷ pfu/mL). Infected cells were harvested at 24, 48, and 72 hours. These samples were later analyzed for protein expression by immunoblot analysis with the anti-HpCh5 antibody.

EXAMPLE 8

Baculovirius Expression of HPCH5

Primer Design for ER Signal Sequence

The original HpF5 cDNA clone did not encode an ER signal sequence. While the ER signal sequence was not required for bacterial expression it was essential for baculovirus expression. An ER signal sequence was thus constructed using the DNA sequence from chymotrypsin family 2A which is most closely related to the chymotrypsin family 5.

The sequence was added using PCR reactions with two primers encoding part of the ER signal sequence. The FwBacRECH1 primer had a silent mutation to remove the BamHI restriction digest site and encoded half the ER signal sequence. The FwBacRECH2 primer encoded the remainder of the ER signal sequence and introduced a BamHI restriction site (FIG. 28).

Amplification and Ligation of HpCh5 into the pFastBac Vector

PCR using primers the FwBacRECH1 and RvRECH and HpF5cDNA as the template yielded a product of ~900 bp. A second PCR using this PCR product together with FwBacRECH2 and RvRECH primers was performed to yield a product of ~930 bp that encoded the HpCh5 protein with an ER signal sequence. The amplified product was subcloned into pCR (registered trademark)-2.1 TOPO vector (Invitrogen) before transfection into TOP10 competent cells. Colonies were screened for the presence of insert using M13 forward and reverse primers. Restriction digests of the isolated plasmids with EcoRI then subsequently with BamHI and HindIII yielded a product of the expected size of ~930 bp.

The ~930 bp fragment was subsequently ligated into the pFastBac vector to create pFastBac/HpF5/ER. The presence of the HpF5 cDNA insert in the pFastBac vector was confirmed by restriction digests with BamHI and HindIII and PCR using FwBacRECH2 and RVRECH primers (Table 9). Plasmids containing the insert were sent to Micromon for DNA sequencing.

Analysis of Bacmid DNA

The transfection of the recombinant pFastBac vector into DH10Bac cells resulted in the transposition of the HpF5 insert into the bacmid DNA. Recombinant bacmid DNA was isolated from the transfected cells and was separated on a 0.5% (w/v) agarose gel.

The bacmid was checked for the HpF5 cDNA insert by PCR analysis with M13 forward and reverse primers. The expected ~3300 bp fragment was further analysed using the primers to HpF5/ER cDNA and M13 to ensure the insert was in the correct orientation. The positive bacmid DNA was subsequently used for the transfection of insect cells.

Virus Formation and Production of HpCh5 in the Baculovirus Expression System

Figure 29A:
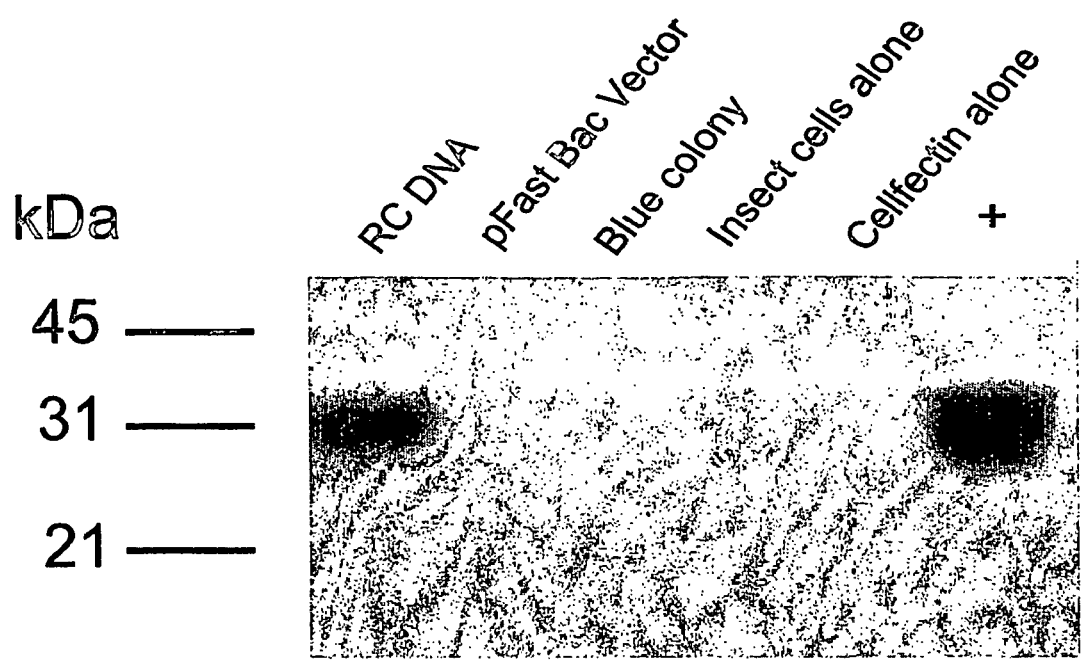
Figure 29B:
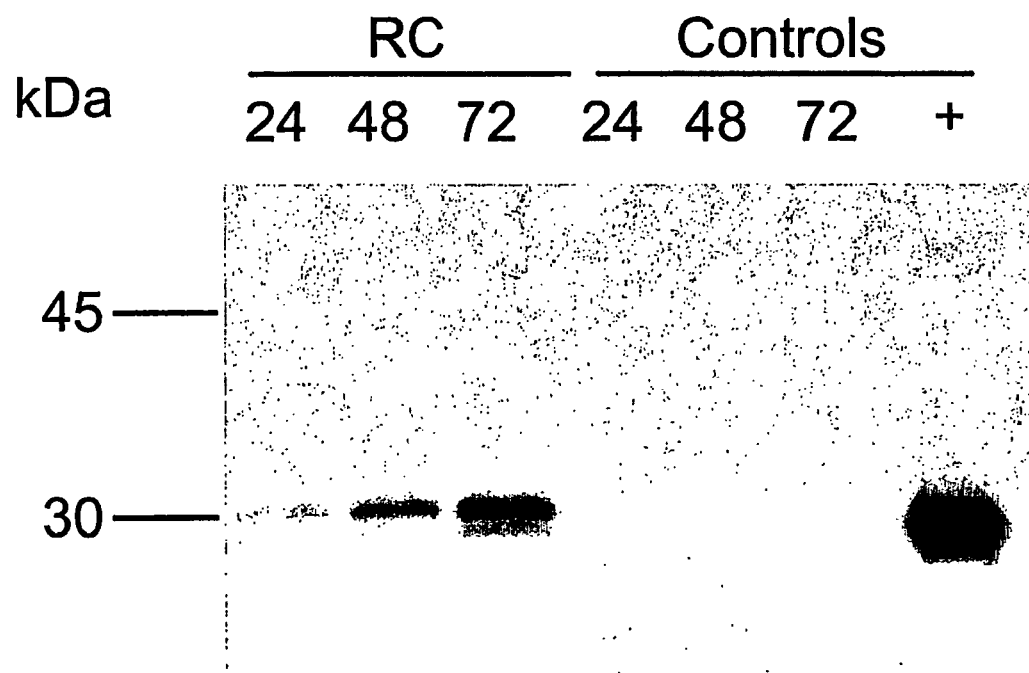

Three different concentrations of bacmid DNA were used to transfect the insect cells for production of baculovirus. After transfection, the cells were incubated at 27° C. for 72 hours before the culture medium containing the virus was collected. The medium was tested by immunoblot analysis with the α-HpCh5 antibodies for the production of HpCh5 protein, which indicated virus was being produced (FIG. 29A). Many controls were used to monitor the transfection. These included pFastBac vector alone, transfection of DNA from a blue colony, incubation of cells with CELLFECTIN (registered trademark) alone and non-transfected cells (FIG. 29A). The medium containing virus was used in a subsequent experiment to infect more insect cells on a larger scale and a time course was performed over a 72 hour period to monitor the regulation of HpCh5 expression (FIG. 29B).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The sequence listing attached is hereby incorporated by reference in this application. (See Mar. 12, 2007 sequence listing as filed.txt created on Mar. 12, 2007 that is 102,271 bytes),

BIBLIOGRAPHY

Altschul et al., *Nucl. Acids Res.* 25: 3389-3402, 1997
Antcheva et al., *Protein Sci.* 10: 2280-2290, 2001
Atkinson et al., *The Plant Cell* 5: 203-213, 1993
Ausubel et al., "Current Protocols in Molecular Biology" John Wiley & Sons Inc, 1994-1998, Chapter 15, 1998
Balandin et al., *Plant Mol. Biol.* 27: 1197-1204, 1995
Beuning and Christeller, *Plant Physiol* 102: 1061, 1993
Bevan, Nucl. Acids Research, 12: 8711-8721, 1984
Bonner and Laskey, *Eur. J Biochem.* 46: 83, 1974
Botos et al., *J. Mol. Biol.* 298: 895-901, 2000
Botos et al., *Journal of Molecular Biology* 298: 895-901, 2000
Bown, et al., *Insect Biochem. Molec. Biol.* 27: 625-638, 1997
Bradford, *Anal Biochem* 72: 248-254, 1976
Broadway and Duffey, *J. Insect Physiol.* 32: 673-680, 1986a
Broadway and Duffey, *J. Insect Physiol.* 32: 827-833, 1986b
Broadway and Villani, *Entomol. Expo. Appl.* 76: 303-312, 1995
Broadway, *Arch. Insect Biochem. Physiol.* 32(1): 39-53, 1996
Broadway, *J. Insect. Physiol.* 41: 107-116, 1995
Broadway, *J. Insect. Physiol.* 43(9): 855-874, 1997
Burgess et al., *Entomol. Exp. App.* 61: 123-130, 1991
Choi et al., *Biochim. et Biophys. Acta* 1492: 211-215, 2000
Christeller et al., *Insect Biochem. Molecul. Biol.* 22:-735-746, 1992
Cleveland et al., *Plant Mol. Biol.* 8: 199-207, 1987
Combet et al., *TIBS.* 25: 147-150, 2000
Cordero et al., In: General Meeting of the International Program on Rice Biotechnology of the Rockefeller Foundation, Malacca, Malaysia, 1997
Cripps et al., *J. Cell Biol.* 126: 689-699, 1994
De Leo et al., *Plant Physiol.* 118: 997-1004, 1998
Erickson et al., *Science* 249: 527-533, 1990
Fang et al., *Plant Cell* 1: 141-150, 1989
Gatehouse et al., In: *Plant Genetic Manipulation for Crop Protection, Biotech.* in Agriculture No. 7, Eds. Gatehouse, Hilder & Boulter, International U.K., pp. 155-181, 1992
Gatehouse et al., *J. Insect Physiol.* 45 (6), 545-558, 1999
Gatehouse, et al., *Insect Biochem. Molecul. Biol.* 27: 929-944, 1997
Graham et al., *J. Biol. Chem.,* 260: 6555-6560, 1985
Greenblatt et al., *J. Mol. Biol.* 205: 201, 1989
Greer, *Proteins* 7: 317-34, 1990
Hajdukiewicz et al., *Plant Mol. Biol.* 25: 989-994, 1994
Harsulkar, et al., *Plant Physiol.* 121: 497-506, 1999
Heath et al., *European Journal of Biochemistry* 230(1): 250-257, 1995
Heath et al, *J. Insect Physiol.* 43: 833-842, 1997
Hediger et al., *Insect Mol. Biol.* 10: 113-119, 2001
Hsu et al., *Plant Sci.* 143: 63-70, 1999
Johnston et al., *Insect Biochem.* 21: 389-397, 1991
Johnston et al., *Insect Biochem. Molec. Biol.* 25(3): 375-383, 1995
Jongsma et al., *Proc. Natl. Acad. Sci. USA* 92(17): 8041-8045, 1995a
Jose Cordero et al., *Plant J.* 6.: 141-150, 1994
Keil et al., *EMBO J.* 8: 1323-1330, 1989
Lee and Anstee, *Insect. Biochem. Molec. Biol.* 25(1): 49-61, 1995b
Lee and Anstee, *Insect. Biochem. Molec. Biol.* 25: 63-71, 1995a
Lee et al., *Nature Structural Biology* 6(6): 526-530, 1999
Legavre et al., In: Vth International Congress of Plant Molecular Biology, Singapore, 1997
Lidholm et al., *Genetics* 134: 859-868, 1993
Lindhorst et al., *Plant Mol, Biol.* 21: 985-992, 1993
Lozovskaya et al., *Genetics* 142: 173-177, 1996
Markwick et al., *J. Economic Entomology* 91 (6): 1265-76, 1998
Markwick et al., *J. Economic Entomology* 88(1): 33-39, 1995
Marmur and Doty, *J. Mol. Biol.* 5: 109, 1962
Mazumdar-Leighton and Broadway, *Insect Biochem. Mol. Biol.* 31: 645-657, 2001a
Mazumdar-Leighton and Broadway, *Insect Biochem. Mol. Biol.* 31:633-644, 2001 b
Miller et al., *Plant Cell* 11: 1499-1508, 1999
Miller et al., *Plant Mol. Biol.* 42: 329-333, 2000
Moura and Ryan, *Plant Physiol.* 126: 289-298, 2001
Nielson et al., *Biochemistry* 34: 14304-14311, 1995
Nielson et al., *J. Mol. Biol.* 242: 231-243, 1994
Patankar, et al., *Insect Biochem. & Mol. Biol.* 31: 453-464, 2001
Pathirana et al., *Plant J.* 12: 293-304, 1997
Paulillo, et al., *J. Econ. Entomol.* 93:892-896, 2000
Peloquin et al., *J. Cot. Sci.* 5: 114-120, 2001
Pesole, *Trends Genet,* 15: 378, 1999
Peterson et al., *Insect Biochem. Mol. Biol.* 25: 765-774, 1995
Pujade-Renaud et al., *Plant Physiol. Biochem.* 35: 85-93, 1997
Richardson and Cossins, *FEBS Letters,* 52: 161, 1975
Ryan, *Annu. Rev. Phytopathol.* 28: 425-449, 1990
Samac and Shah, *Plant Cell* 3: 1063-1072, 1991
Schoenbeck et al., *Molec. Plant-Microbe Interact,* 1999
Seemuller et al., *Hoppe-Seyler's Z. Physiol. Chem.* 358: 1105-1117, 1977
Stewart and Hsu, *Planta* 137: 113-117, 1977
Summerton and Weller, *Antisense and Nucleic Acid Drug Development* 7: 187-195, 1997
Taylor et al., *Plant Mol. Biol.* 23: 1005-1014, 1993
Teakle et al., *Journal of Invertebrate Pathology* 46: 166-173, 1985
Terra and Ferreira, *Comp. Biochem. Physiol.* 109: 1-62, 1994
Valiatis et al., *Insect Biochemistry and Molecular Biology* 29: 405-415, 1999
Volpicella et al., *Eur. J. Biochem.* 270: 10-19, 2003
Wells, *Methods Enzymol.* 202: 2699-2705, 1991
Wu et al., *Molecular Breeding* 3: 371-380, 1997
Xu and Qin, *J. Econ. Entomol.* 87: 334-338, 1994

The invention claimed is:

1. An antagonist that comprises an amino acid sequence having at least 90% amino acid sequence identity to the amino acid sequence set forth in SEQ ID NO:81 and that inhibits the proteolytic activity of the protein having the amino acid sequence set forth in SEQ ID NO:2.

2. The antagonist of claim 1 wherein said antagonist comprises an amino acid sequence having at least 95% amino acid sequence identity to the amino acid sequence set forth in SEQ ID NO:81.

3. The antagonist of claim 1 wherein said antagonist comprises the amino acid sequence set forth in SEQ ID NO:81.

4. A composition comprising an antagonist of claim 1.

5. A composition comprising the antagonist of claim 2.

6. A composition comprising the antagonist of claim 3.

7. An isolated nucleic acid molecule having a sequence encoding the antagonist amino acid sequence according to claim 1.

8. The isolated nucleic acid molecule of claim 7, wherein the antagonist comprises an amino acid sequence with at least 95% sequence identity to the amino acid sequence set forth in SEQ ID NO:81.

9. The isolated nucleic acid molecule of claim 7, wherein the antagonist comprises the amino acid sequence set forth in SEQ ID NO:81.

10. A vector comprising the antagonist-encoding nucleic acid sequence according to claim 7.

11. A vector comprising the antagonist-encoding nucleic acid sequence according to claim 8.

12. A vector comprising the antagonist-encoding nucleic acid sequence according to claim 9.

13. An isolated genetically modified cell comprising a nucleic acid molecule having a sequence encoding an amino acid sequence having at least 90% amino acid sequence identity to the amino acid sequence set forth in SEQ ID NO:81 and that inhibits the proteolytic activity of the protein having the amino acid sequence set forth in SEQ ID NO:2.

14. An isolated genetically modified cell comprising a nucleic acid molecule having a sequence encoding an amino acid sequence having at least 95% amino acid sequence identity to the amino acid sequence set forth in SEQ ID NO:81 and that inhibits the proteolytic activity of the protein having the amino acid sequence set forth in SEQ ID NO:2.

15. An isolated genetically modified cell comprising a nucleic acid molecule having a sequence encoding the amino acid sequence set forth in SEQ ID NO:81.

16. The isolated cell of claim 13 which is a genetically modified plant cell.

17. The isolated cell of claim 14 which is a genetically modified plant cell.

18. The isolated cell of claim 15 which is a genetically modified plant cell.

* * * * *